(12) United States Patent
Hough et al.

(10) Patent No.: US 9,080,135 B2
(45) Date of Patent: Jul. 14, 2015

(54) COMPOSITIONS WITH FREEZE THAW STABILITY

(75) Inventors: Lawrence Alan Hough, Philadelphia, PA (US); Wojciech Bzducha, Lyons (FR); Pascal Herve, West Windsor, NJ (US); Pierre Hennaux, New York, NY (US); Mary O'Rourke, Bensalem, PA (US); Ericka Park, Cherry Hill, NJ (US)

(73) Assignee: RHODIA OPERATIONS, Paris (FR)

( * ) Notice: Subject to any disclaimer, the term of this patent is extended or adjusted under 35 U.S.C. 154(b) by 199 days.

(21) Appl. No.: 13/026,686

(22) Filed: Feb. 14, 2011

(65) Prior Publication Data

US 2011/0223125 A1  Sep. 15, 2011

Related U.S. Application Data

(60) Provisional application No. 61/337,927, filed on Feb. 12, 2010, provisional application No. 61/428,628, filed on Dec. 30, 2010.

(51) Int. Cl.

| | |
|---|---|
| *A61K 8/92* | (2006.01) |
| *A61Q 19/10* | (2006.01) |
| *A61Q 5/12* | (2006.01) |
| *A61Q 5/02* | (2006.01) |
| *C09K 8/60* | (2006.01) |
| *C09K 8/80* | (2006.01) |
| *C11D 3/37* | (2006.01) |
| *A61K 8/81* | (2006.01) |
| *A61K 8/86* | (2006.01) |
| *A61Q 19/00* | (2006.01) |
| *C08F 220/30* | (2006.01) |
| *C11D 17/00* | (2006.01) |
| *C09K 8/68* | (2006.01) |
| *C09K 8/88* | (2006.01) |
| *C08F 283/06* | (2006.01) |
| *C08F 290/06* | (2006.01) |
| *C08F 220/28* | (2006.01) |

(52) U.S. Cl.
CPC ............ *C11D 3/3765* (2013.01); *A61K 8/8152* (2013.01); *A61K 8/86* (2013.01); *A61Q 19/00* (2013.01); *A61Q 19/10* (2013.01); *C08F 220/30* (2013.01); *C08F 283/065* (2013.01); *C08F 290/062* (2013.01); *C09K 8/68* (2013.01); *C09K 8/685* (2013.01); *C09K 8/88* (2013.01); *C09K 8/887* (2013.01); *C11D 3/37* (2013.01); *C11D 3/3707* (2013.01); *C11D 3/3773* (2013.01); *C11D 17/0026* (2013.01); *A61K 2800/52* (2013.01); *C08F 2220/288* (2013.01)

(58) Field of Classification Search
USPC ......................................................... 424/70
See application file for complete search history.

(56) References Cited

U.S. PATENT DOCUMENTS

| | | |
|---|---|---|
| 2,458,888 A | 1/1949 | Rehberg et al. |
| 3,035,004 A | 5/1962 | Glavis |
| 3,652,497 A | 3/1972 | Junas et al. |
| 3,937,283 A | 2/1976 | Blauer et al. |
| 4,138,381 A | 2/1979 | Chang et al. |
| 4,351,754 A | 9/1982 | Dupre |
| 4,384,096 A | 5/1983 | Sonnabend |
| 4,579,670 A | 4/1986 | Payne |
| 4,620,028 A | 10/1986 | Gorman et al. |
| 4,668,410 A | 5/1987 | Haas et al. |
| 4,734,099 A | 3/1988 | Cyprien |
| 4,830,769 A | 5/1989 | O'Lenick et al. |
| 4,892,916 A | 1/1990 | Hawe et al. |
| 5,104,643 A | 4/1992 | Grollier et al. |
| 5,292,843 A | 3/1994 | Jenkins et al. |
| 5,294,693 A | 3/1994 | Egraz et al. |
| 5,415,860 A | 5/1995 | Beucherie et al. |
| 5,551,516 A | 9/1996 | Norman et al. |
| 5,607,680 A | 3/1997 | Brissonnet et al. |

(Continued)

FOREIGN PATENT DOCUMENTS

| | | |
|---|---|---|
| CN | 1422147 A | 6/2003 |
| CN | 1606427 A | 4/2005 |

(Continued)

OTHER PUBLICATIONS

C.E. Rehberg, et al., "Preparation and Properties of Monomeric and Polymeric Acrylic Esters of Ether-Alcohols," Journal of Organic Chemisty, vol. 14, pp. 1094-1098, XP002594784.

(Continued)

*Primary Examiner* — Mina Haghighatian
*Assistant Examiner* — Luke Karpinski

(57) ABSTRACT

Composition including freeze thaw stability polymer such as a copolymer having a weight average molecular weight of at least about 30,000 grams per mole, a blend of a first polymer and a second polymer, a crosslinked alkali swellable acrylate copolymer, or at least one polymerizable reactive alkoxylated acrylate monomer. The copolymer has one or more first monomeric units and one or more second monomeric units. The one or more first monomeric units each independently including at least one bicycloheptyl-polyether, bicycloheptenyl-polyether or branched ($C_5$-$C_{50}$)alkyl-polyether group per monomeric unit. The bicycloheptyl-polyether or bicycloheptenyl-polyether group may optionally be substituted on one or more ring carbon atoms by one or two ($C_1$-$C_6$)alkyl groups per carbon atom. The one or more second monomeric units each independently including at least one pendant linear or branched ($C_5$-$C_{50}$)alkyl-polyether group per monomeric unit. The first and second monomeric units do not both have branched ($C_5$-$C_{50}$)alkyl-polyether group.

20 Claims, 2 Drawing Sheets

(56) References Cited

U.S. PATENT DOCUMENTS

| | | | |
|---|---|---|---|
| 5,674,823 | A | 10/1997 | Ricca et al. |
| 5,686,024 | A | 11/1997 | Dahanayake et al. |
| 5,853,710 | A | 12/1998 | Dehan et al. |
| 5,858,343 | A | 1/1999 | Szymczak |
| 5,874,495 | A | 2/1999 | Robinson et al. |
| 5,902,574 | A | 5/1999 | Stoner et al. |
| 5,902,778 | A | 5/1999 | Hartmann et al. |
| 6,150,312 | A | 11/2000 | Puvvada et al. |
| 6,162,877 | A | 12/2000 | Sau |
| 6,433,061 | B1 | 8/2002 | Marchant |
| 6,846,798 | B2 | 1/2005 | Joye et al. |
| 6,897,253 | B2 | 5/2005 | Schmucker-Castner et al. |
| 7,217,752 | B2 | 5/2007 | Schmucker-Castner et al. |
| 7,288,616 | B2 | 10/2007 | Tamareselvy et al. |
| 7,378,479 | B2 | 5/2008 | Tamareselvy et al. |
| 7,772,421 | B2 | 8/2010 | Yang et al. |
| 8,071,674 | B2 | 12/2011 | Yang et al. |
| 8,501,860 | B2 | 8/2013 | Yang et al. |
| 8,501,865 | B2 | 8/2013 | Yang et al. |
| 8,501,983 | B2 | 8/2013 | Yang et al. |
| 8,505,631 | B2 | 8/2013 | Yang et al. |
| 8,507,624 | B2 | 8/2013 | Yang et al. |
| 8,637,624 | B2 | 1/2014 | Yang et al. |
| 8,784,786 | B2 | 7/2014 | Hough et al. |
| 2003/0180246 | A1 | 9/2003 | Frantz et al. |
| 2003/0190302 | A1 | 10/2003 | Frantz et al. |
| 2004/0247549 | A1 | 12/2004 | Lu et al. |
| 2005/0002892 | A1 | 1/2005 | Khan et al. |
| 2005/0175568 | A1 | 8/2005 | Asari et al. |
| 2006/0040837 | A1 | 2/2006 | Frantz et al. |
| 2006/0135627 | A1 | 6/2006 | Frantz et al. |
| 2006/0135683 | A1 | 6/2006 | Adam |
| 2006/0270563 | A1* | 11/2006 | Yang et al. .................... 507/119 |
| 2008/0095733 | A1* | 4/2008 | Griffin et al. .............. 424/70.19 |
| 2011/0243873 | A1 | 10/2011 | Hough et al. |
| 2012/0116005 | A1 | 5/2012 | Yang et al. |
| 2012/0116040 | A1 | 5/2012 | Yang et al. |
| 2012/0121523 | A1 | 5/2012 | Yang et al. |
| 2012/0123149 | A1 | 5/2012 | Yang et al. |
| 2013/0129647 | A1 | 5/2013 | Yang et al. |
| 2014/0099276 | A1 | 4/2014 | Yang et al. |
| 2014/0301966 | A1 | 10/2014 | Hough et al. |

FOREIGN PATENT DOCUMENTS

| | | |
|---|---|---|
| CN | 101517060 A | 8/2009 |
| DE | 3822202 A1 | 1/1998 |
| EP | 226097 B1 | 5/1990 |
| EP | 705852 B1 | 12/1998 |
| EP | 1949888 A1 | 7/2008 |
| GB | 2176794 A | 1/1987 |
| WO | 98/41505 A1 | 9/1998 |

OTHER PUBLICATIONS

Jarchem Industries, Inc., Specialty Monomers, Acrylamides Methacrylates Acrylates others, brochure (2004).

Johansson (Specialty Chemicals Magazine, Nov. 2004: online at URL:<http://www.firp.ula.ve/archivos/material_web_4xx/04_SCM_Johansson.pdf>).

Jarchem, URL:<http://www.jarchem.com/monomers/acrylate_mono.htm>, 2003, retrieved from the Internet via URL:<http://web.archive.org> (WaybackMachine webpage) Aug. 13, 2012.

STN Search Results (Apr. 5, 2012) listed in Notice of References Cited of Office action of Apr. 12, 2012 for U.S. Appl. No. 13/373,162 to Yang et al, filed Nov. 7, 2011.

Office action of Apr. 12, 2012 for U.S. Appl. No. 13/373,162 to Yang et al, filed Nov. 7, 2011.

Office action of May 2, 2012 for U.S. Appl. No. 13/317,948 to Yang et al, filed Nov. 1, 2011.

Office Action of Feb. 27, 2013 from U.S. Appl. No. 12/931,903 to Hough et al, filed Feb. 14, 2011.

Notice of Allowance of Apr. 15, 2013 from U.S. Appl. No. 13/317,948 to Yang et al, filed Nov. 1, 2011.

Notice of Allowance of Apr. 19, 2013 from U.S. Appl. No. 13/373,162 to Yang et al, filed Nov. 7, 2011.

Notice of Allowance of Apr. 16, 2013 from U.S. Appl. No. 13/373,154 to Yang et al, filed Nov. 7, 2011.

Notice of Allowance of Apr. 15, 2013 from U.S. Appl. No. 13/373,170 to Yang et al, filed Nov. 7, 2011.

Notice of Allowance of May 14, 2013 from U.S. Appl. No. 13/728,434 to Yang et al, filed Dec. 27, 2012.

Hough, et al, Characterization of Multilamellar Vesicles for Cleansing Applications, Cosmetics & Toiletries, Nov. 1, 2008, URL : < http://www.cosmeticsandtoiletries.com/formulating/function/delivery/premium-characterization-of-multilamellar-vesicles-for-cleansing-applications-229140051.html >, retrieved from the Internet Jul. 26, 2014.

Notice of Allowance of Dec. 19, 2014 for U.S. Appl. No. 14/105,848 to Yang et al., filed Dec. 13, 2013.

Office Action of Oct. 8, 2014 from U.S. Appl. No. 14/308,845 to Hough et al., filed Jun. 19, 2014.

Office Action of Nov. 20, 2013 from U.S. Appl. No. 12/931,903 to Hough et al., filed Feb. 14, 2011.

Office Action of Aug. 12, 2013 from U.S. Appl. No. 12/931,903 to Hough et al., filed Feb. 14, 2011.

Chinese Office Action of Mar. 5, 2014 from CN Patent Application No. 201180018598.1 to Rhodia Operations.

Supplementary Partial European Search Report dated Feb. 2, 2015 for European Patent Application No. EP11742941.

* cited by examiner

FIG. 1
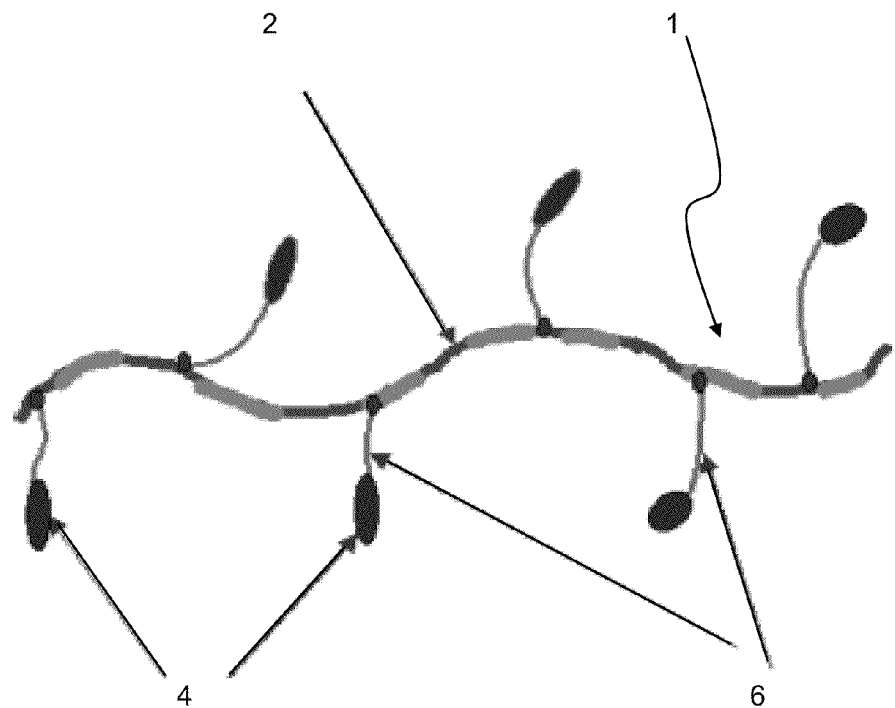
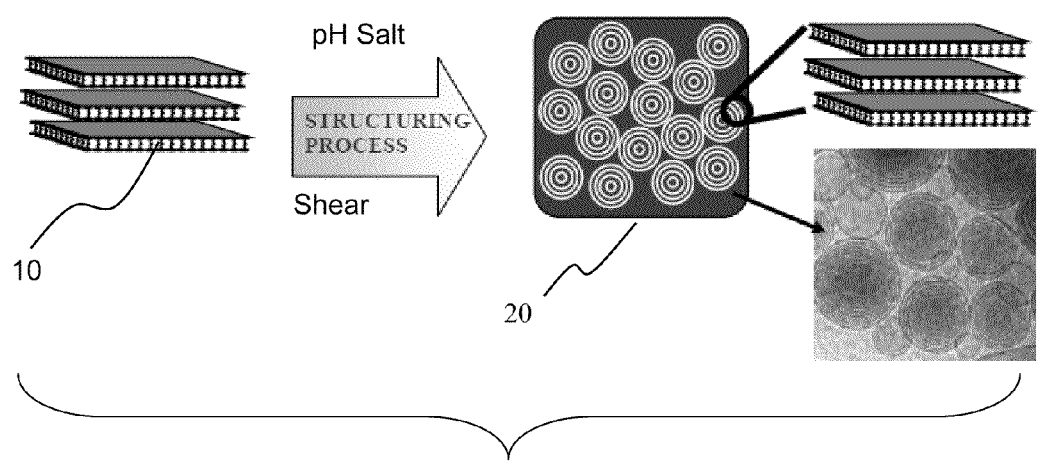
FIG. 2

COMPOSITIONS WITH FREEZE THAW STABILITY

CROSS REFERENCE TO RELATED APPLICATIONS

This claims the benefit of U.S. provisional patent application No. 61/337,927 filed Feb. 12, 2010 and U.S. provisional patent application No. 61/428,628 filed Dec. 30, 2010, both incorporated herein by reference.

FIELD OF THE INVENTION

This present invention relates to aqueous compositions with freeze-thaw stability. For example, an aqueous personal care formulation, which can be in the form of a hand or body soap (liquid or bar), lipstick, body wash, makeup remover, skin cleaner, hair conditioner, skin or hair moisturizer. In particular, the present invention employs yield bringing monomers combined with viscosity bringing monomers in hydrophobically modified alkali swellable emulsion (HASE) rheology modifier polymer for use in aqueous personal care formulations having freeze-thaw stability.

BACKGROUND

In personal care applications, consumers are increasingly demanding formulations that provide multiple benefits such as, but not limited to, unique sensory experience, enhanced moisturization, increased conditioning, improved delivery of active ingredients and compatibility. These molecules can provide many of the above benefits listed either by themselves or in certain cases can have synergistic effects with principal functioning agents resulting in increased efficacy or a reduction in the amount of the agent used. These molecules can provide these benefits either while in use and/or after rinsing which makes them unique and opens the possibility to be used in both "leave on" and "rinse off" products. Synthetic rheology modifier polymers can be employed to assist in achieving one or more of these properties.

Typical synthetic rheology modifier polymers are: alkali-soluble emulsion ("ASE") polymers, hydrophobically modified alkali-soluble emulsion ("HASE") polymers, hydrophobically modified ethoxylated urethane ("HEUR") polymers, and hydrophobically modified nonionic polyol ("HNP") polymers.

HASE and ASE polymers, see, for example those described in, U.S. Pat. No. 3,035,004, U.S. Pat. No. 5,292,843, U.S. Pat. No. 6,897,253, U.S. Pat. No. 7,288,616, U.S. Pat. No. 7,378,479, and US Patent Publication No. 2006/0270563, have each been widely used as rheology modifiers in aqueous systems. However, some HASE polymers have shown deficiencies with respect to thickening efficiency, such as undesirably high sensitivity to relatively small variations in pH, electrolyte concentration, and the amount of polymer used. The thickening efficiency of such polymers in aqueous media tends to be low at low polymer concentration, for example, less than about 1% by weight polymer, particularly at low pH, such as for example, pH of less than about 6, but tends to markedly increase at higher polymer concentrations and/or higher pH. This sensitivity can lead to undesirably large changes in rheological properties, such as very dramatically increased viscosity, with relatively small changes in pH or polymer concentration. The disproportionately large changes in properties can lead to difficulty in designing a composition that has and maintains a desired performance profile under anticipated conditions of use, as well as to difficulties in manufacturing and handling such compositions.

U.S. Pat. No. 7,217,752 to Schmucker-Castner et al discloses a stable, aqueous composition containing a substantially crosslinked alkali-swellable acrylate copolymer rheology modifier, a surfactant, an alkaline material, and various compounds therein, as for example substantially insoluble materials requiring suspension or stabilization, such as a silicone, an oily material, or a pearlescent material. Additionally, this invention also relates to the formation of a rheologically and phase stable cationic hair dye composition.

Cross-linked ASE polymers have also shown deficiencies with respect to thickening efficiency and thus may, particularly at low pH, require an undesirably large amount of polymer to provide the desired level of thickening, and, when used in an amount sufficient to provide the desired rheological properties, impart a cloudy, translucent, or opaque optical appearance to aqueous compositions. A cloudy, translucent, or opaque optical appearance may be undesirable in end uses in which aesthetic criteria are important such as, for example, in personal care formulations, such as shampoos and body washes. Furthermore, some HASE and ASE polymers typically exhibit a lower thickening efficiency and/or impart a cloudy, translucent or opaque optical appearance in the presence of salts and surfactants, which also limits the usefulness of such polymers in some aqueous systems, such as for example, personal care compositions.

A desirable property in a formulation is yield. Yield is the ability to suspend particles in the formulation. One way to enhance yield is by employing structured surfactants. Structured Surfactant Liquid exhibit a close packed network of Multi-Lamellar Vesicles (MLVs) which accounts for their unique properties such as high loading of oils and fragrances. They are used in the Personal Care market to make rinse-off formulations (e.g. body washes and shampoos).

U.S. Patent Application Publication No. US2003/0180246 A1 discloses structured surfactant compositions that comprise an anionic surfactant and an alkanolamide. U.S. Patent Application Publication No. US2003/0190302 A1 discloses structured surfactant compositions that comprise an anionic surfactant and a cationic surfactant. U.S. Patent Application Publication No. US2006/0135627-A1 discloses structured surfactant compositions that comprise an anionic surfactant and an amine oxide.

U.S. Patent Application Publication No. 2006/040837 A1 discloses an aqueous, low pH structured surfactant composition, contains, based on 100 parts by weight of the composition, from about 3 parts by weight to about 40 parts by weight of one or more anionic surfactants selected from anionic phosphate ester surfactants, anionic sulfonate surfactants, and anionic carboxylate surfactants, wherein the composition exhibits a pH of less than about 5, exhibits shear-thinning viscosity, and is capable of suspending water insoluble or partially water soluble components.

U.S. Pat. No. 6,150,312 discloses when there is sufficient surfactant to form micelles (i.e. the concentrations are above the critical micelle concentration or CMC), for example spherical, cylindrical (rod-like) or discoidal micelles may form. As the surfactant concentration increases, ordered phases such as lamellar phase, hexagonal phase or cubic phase may form. The lamellar phase, for example, consists of alternating surfactant bilayers and water layers. These layers may be planar and/or fold to form submicron spherical onion like structures called vesicles or liposomes or spherulites. The lamellar phase having an ordered structure. The hexagonal phase, on the other hand, consists of long cylindrical micelles arranged in a hexagonal lattice. In general, the microstructure of most personal care products consists of either spherical micelles, rod micelles, or a lamellar dispersion.

One problem with certain lamellar phase compositions is that they tend to lose their lamellar stability in colder temperatures (e.g., −18° C. to 7° C. (0 to 45° F.)). During a freeze thaw cycle some structured surfactant formulations phase separate when the bi-layers of the MLVs (multi-lamellar vesicles) become unstable either through changes in bilayer elasticity or solubility of the surfactants. Improved structured surfactant systems, for example, systems with improved freeze-thaw stability, are desired.

Personal care formulations are launched on a global scale, thus their resistance through Freeze-Thaw is an important parameter. The stability requirement for a personal care formulation depends on the geography in which it is to be bought and sold. Indeed, according to the country in which the formulation is to be used, it will have to resist to very different temperatures, humidity, etc. Formulations may need to travel by truck, train or ship across very different temperatures, from freezing to desert heat. Therefore an acceptable "shelf life" is determined for each composition. It represents the amount of time during which the formulation should remain stable across its normal storage and handling conditions. It is measured between the time the composition is produced and when it is used by the consumer. Generally, personal care formulations require a two year shelf life.

SUMMARY OF THE INVENTION

Unexpectedly, the applicants have now found certain polymers, can be used at small levels to enhance both initial viscosity and low temperature viscosity, thereby providing much more stable compositions.

In a first aspect, the present invention is directed to a freeze thaw stable composition with improved freeze thaw stability, comprising:
 a continuous phase comprising:
 a freeze thaw stability polymer selected from at least one member of the group consisting of:
  a polymer having a weight average molecular weight of greater than or equal to about 30,000 grams per mole,
  a blend of a first polymer and a second polymer,
  a crosslinked alkali swellable acrylate copolymer, and
  at least one polymerizable reactive alkoxylated acrylate monomer;
 A. said polymer having a weight average molecular weight of greater than or equal to about 30,000 grams per mole comprising:
  (a) one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom,
  (b) one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group, and
  (c) at least one polymerizable functional group per molecule of polymer;
 B. said blend of said first polymer comprising one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom at least one polymerizable functional group per molecule of first polymer, and said second polymer comprising one or more second monomeric units, each independently comprising at least one pendant linear or branched ($C_5$-$C_{50}$) alkyl-polyether group per monomeric unit, provided that the first and second monomeric units each have a weight average molecular weight of greater than or equal to about 30,000 grams per mole and cannot both comprise a branched ($C_5$-$C_{50}$)alkyl-polyether group, and at least one polymerizable functional group per molecule of second polymer;
 C. said crosslinked alkali swellable acrylate copolymer comprising from about 20% to about 80% by weight of at least one carboxylic acid monomer comprising acrylic acid, methacrylic acid, itaconic acid, fumaric acid, crotonic acid, aconitic acid, or maleic acid, or combinations thereof; from about 80% to about 15% by weight of at least one alpha, beta-ethylenically unsaturated monomer; and from about 0.01 to about 5% by weight of at least one polyunsaturated compound useful in forming a partially or substantially crosslinked three dimensional network,
 wherein the at least one alpha, beta-ethylenically unsaturated monomer has the formula: $CH_2$=CXY, wherein X is H and Y is —COOR, —$C_6H_4$R', —CN, —$CONH_2$, —Cl, —$NC_4H_6O$, $NH(CH_2)_3COOH$, —$NHCOCH_3$, —$CONHC(CH_3)_3$, —CO—$N(CH_3)_2$;
  or X is $CH_3$ and Y is —COOR, —$C_6H_4$R', —CN, or —CH=$CH_2$;
  or X is Cl and Y is Cl, wherein R is $C_1$-$C_{18}$ alkyl, or hydroxy $C_2$-$C_{18}$ alkyl, R' is H or $C_1$-$C_{18}$ alkyl; or
  has the formula: $CH_2$=CH(OCOR$_1$), wherein R$_1$ is $C_1$-$C_{18}$ alkyl; or
  has the formula: $CH_2$=$CH_2$ or $CH_2$=$CHCH_3$; and
 D. said at least one polymerizable reactive alkoxylated acrylate monomer having the structural formula selected from the group consisting of structural formula IA or structural formula IB:

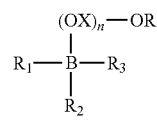

IA

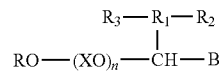

IB wherein B is a 5 or 6 membered cycloalkyl ring, or a single ring aromatic hydrocarbon having a 6 membered ring, R1, R2 and R3 are independently selected from the group consisting of structural formula IC, ID, IE and IF:

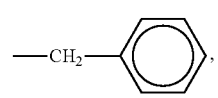

IC

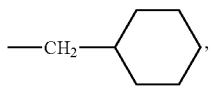
ID

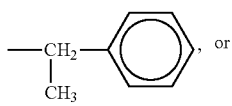
IE

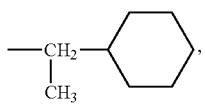
IF wherein, X is selected from the group consisting of $C_2H_4$, $C_3H_6$, and $C_4H_8$; wherein n is in the range of 1-100, wherein R is an ethylenically unsaturated group; and the composition further comprising:
water;
a surfactant; and
optionally an additive selected from at least one member of the group consisting of:
1) a water insoluble component suspendable at 25° C., which is insoluble in the aqueous phase of the composition at −10° C., and not suspendable after exposure to the temperature of −10° C. upon returning to 25° C. in a comparative composition the same as said freeze thaw stable composition but for an absence of the freeze thaw stability polymer,
2) a water soluble component suspendable or soluble in the aqueous phase of the composition at 25° C., which is insoluble in the aqueous phase at −10° C., and not suspendable or soluble in the composition after exposure to the temperature of −10° C. upon returning to 25° C. in a comparative composition the same as said freeze thaw stable composition but for an absence of the freeze thaw stability polymer,
3) at least a portion of the surfactant suspendable or soluble in the aqueous phase at 25° C., which is not suspendable or soluble in the composition after exposure to the temperature of −10° C. upon returning to 25° C. in a comparative composition the same as said freeze thaw stable composition but for an absence of the freeze thaw stability polymer, and
4) a water insoluble component suspendable in the continuous phase of the composition which does not phase separate or settle after three freeze thaw cycles, whereas in the absence of the freeze thaw stability polymer the water insoluble component is not suspendable in the continuous phase after three freeze thaw cycles; each freeze thaw cycle comprising exposing the composition to 12 hours at 25° C. and 12 hours at −10° C.

Typically, a formulation has a freeze thaw issue for 3 reasons.
1. The viscosity decreases at low temperature and is not sufficient to suspend insoluble additives
2. The surfactant is insoluble at low temperatures
3. The structured surfactant compositions lose the structure at low temperature.

The viscosity imparted by the polymer does not decrease at low temperature. This should be applicable to a variety of formulations. The viscosity does not decrease, thus, phase separation does not occur.

The invention is useful for anything that has bound water or a phase transition associated with temperature, e.g., personal care compositions such as rinse off, shampoo, body wash, conditioners, or a home care composition, for example, laundry detergent, cationic surfactant based fabric softener, or an oil field composition such as hydraulic fracturing fluid or enhanced oil recovery compositions.

The compositions of the present invention typically have an absence of latex particles. Also, the compositions of the present invention typically have an absence of paint binders. It is noted below described HASE polymers if a latex are not these avoided latex particles.

The polymer of the present invention is useful in, for example, personal care applications, such as shampoos, body wash, hand soap, lotions, creams, conditioners, shaving products, facial washes, neutralizing shampoos, personal wipes, and skin treatments.

The polymer of the present invention is useful in, for example, a cosmetic composition for removing makeup from the skin and/or eyes, and/or for the cleansing thereof, comprising a cosmetically acceptable vehicle or carrier comprising a fatty phase and an aqueous phase, and the polymer.

Typically, the water insoluble additive is selected from the group consisting of:
personal care benefit agents selected from the group consisting of oil, mica, exfoliation beads, emollients, moisturizers, pearlizing agent, a silicone hair conditioning agent, an antidandruff ingredient, a glycol emulsifier;
hydraulic fracturing proppant; and
home care additives selected from the group consisting of organic based degreasing agents and/or soil release agents, builders and fragrances.

Typically, the amount of the surfactant is from about 1% to about 80% by weight based upon the total weight of said stable composition, and wherein the amount of the copolymer is from about 0.1% to about 10% by weight based upon the total weight of the aqueous composition.

Typically, the hydrophobically modified alkali-soluble acrylate copolymer is a hydrophobically modified alkali-soluble emulsion ("HASE") polymer. Typically the at least one polymerizable functional group per molecule of the HASE polymer is provided by third monomeric units selected from one or more members of the group consisting of acrylic acid groups and methacrylic acid groups. Optionally the third monomeric units independently comprise at least one acid monomeric unit, each acid monomeric unit independently comprising a carboxylic acid-functional group, a sulfonic acid-functional group, a phosphonic acid-functional group, and a phosphoric acid-functional group. Typically, the acrylate copolymer further comprises at least one fourth monomeric unit independently comprising at least one member of the group consisting of an alkyl group, hydroxyalkyl group, alkoxyalkyl group, cycloalkyl group, aryl group, aralkyl group, or aryloxy group.

Typically, the compositions comprise selected hydrophobically modified alkali swellable emulsion (HASE) polymers comprising yield bringing monomers with viscosity bringing monomers to provide freeze thaw stability to surfactant systems, particularly to structured surfactant systems.

In one embodiment, the hydrophobically modified alkali swellable polymer is the product of copolymerization of a mixture of monomers, comprising:
(a) one or more first monomers, each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom, and
(b) one or more second monomers, each independently selected from monomers that comprise a reactive functional group and at least one pendant straight or branched $(C_5-C_{50})$alkyl-polyether group per molecule and that are copolymerizable with the first monomer, provided that the first and second monomers cannot both comprise a branched $(C_5-C_{50})$alkyl-polyether group;

(c) at least one third monomer providing at least one polymerizable functional group per molecule of polymer;

the polymer having a weight average molecular weight of greater than or equal to about 30,000 grams per mole.

Typically the present invention employs a blend of (a) a first polymer comprising one or more first monomeric units, each independently comprising at least one bicycloheptyl-polyether, bicycloheptenyl-polyether or branched $(C_5-C_{50})$alkyl-polyether group per monomeric unit, wherein the bicycloheptyl-polyether or bicycloheptenyl-polyether group may optionally be substituted on one or more ring carbon atoms by one or two $(C_1-C_6)$alkyl groups per carbon atom, having a weight average molecular weight of greater than or equal to about 30,000 grams per mole, and (b) a second polymer comprising one or more second monomeric units, each independently comprising at least one pendant linear or branched $(C_5-C_{50})$alkyl-polyether group per monomeric unit, provided that the first and second monomeric units cannot both comprise a branched $(C_5-C_{50})$alkyl-polyether group, having a weight average molecular weight of greater than or equal to about 30,000 grams per mole, wherein the first and second monomeric units each further comprise at least one polymerizable functional group per molecule of polymer, and the first and second monomeric units cannot both comprise a branched $(C_5-C_{50})$alkyl-polyether group.

In a preferred aspect, the present invention is directed to aqueous compositions comprising a structured surfactant composition and one or more HASE polymers according to the present invention. Preferably the structured surfactant composition comprises a non-ionic surfactant, a branched anionic and an amphoteric surfactant. Most preferably the structured surfactant composition comprises a non-ionic surfactant, a non-branched anionic and an amphoteric surfactant, wherein at most 10 wt. % of the total surfactant is branched surfactant, wherein the one or more HASE polymers according to the present invention gives the resulting composition improved freeze-thaw stability.

The preferred compositions of the present invention comprising HASE polymer have improved tolerance to salt content and surfactant content compared to typical HASE polymers in regard to thickening efficiency and/or optical clarity. Personal care compositions containing the polymer of the present invention typically exhibit good foam properties and good sensory properties and the polymer is easily rinsed with water from the skin or hair.

BRIEF DESCRIPTION OF THE DRAWINGS

FIG. 1 shows an idealized diagram of the structure of a preferred HASE polymer.

FIG. 2 shows a schematic of a process for forming a structured surfactant.

DETAILED DESCRIPTION OF THE INVENTION

Figure 3:
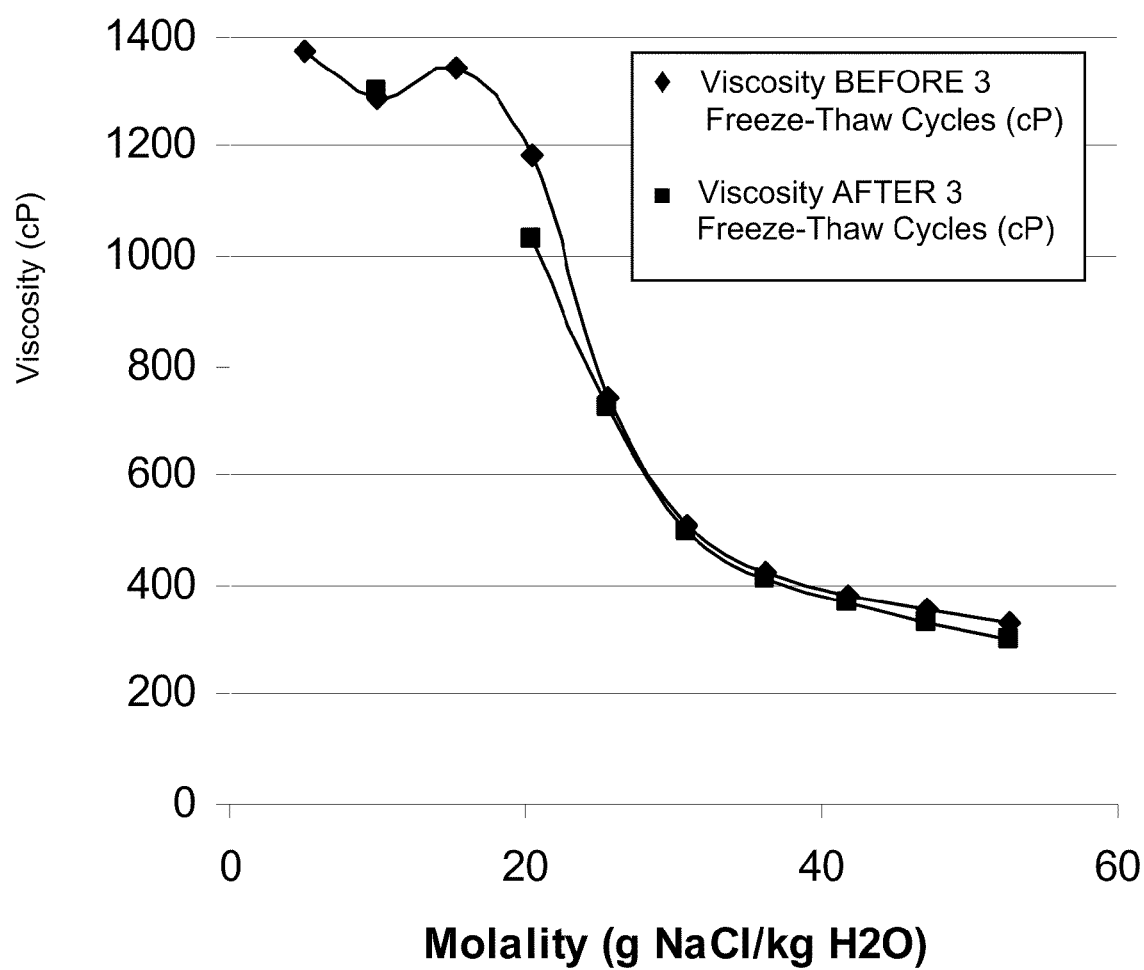
FIG. 3 shows a Salt Curve for 10% Surfactant Blend 1+1% Rhodia HASE Polymer A Formulations with varying NaCl levels.

Compositions for beauty and personal care include a wide variety of products, such as shampoos and formulations for hand and/or body wash, hair and skin conditioners, hand cream and makeup removal product. A variety of personal care compositions are described by U.S. Pat. No. 6,864,314, herein incorporated by reference in its entirety.

As used herein, the term "alkyl" means a monovalent straight or branched saturated hydrocarbon radical, more typically, a monovalent straight or branched saturated $(C_1-C_{40})$hydrocarbon radical, such as, for example, methyl, ethyl, n-propyl, isopropyl, n-butyl, isobutyl, tert-butyl, hexyl, octyl, hexadecyl, octadecyl, eicosyl, behenyl, tricontyl, and tertacontyl.

As used herein, the term "alkoxyl" means an oxy radical that is substituted with an alkyl group, such as for example, methoxyl, ethoxyl, propoxyl, isopropoxyl, or butoxyl, which may optionally be further substituted on one or more of the carbon atoms of the radical.

As used herein, the term "alkoxyalkyl" means an alkyl radical that is substituted with one or more alkoxy substituents, more typically a $(C_1-C_{22})$alkyloxy-$(C_1-C_6)$alkyl radical, such as methoxymethyl, and ethoxybutyl.

As used herein, the term "alkenyl" means an unsaturated straight or branched hydrocarbon radical, more typically an unsaturated straight, branched, $(C_2-C_{22})$ hydrocarbon radical, that contains one or more carbon-carbon double bonds, such as, for example, ethenyl, n-propenyl, iso-propenyl, As used herein, terms "aqueous medium" and "aqueous media" are used herein to refer to any liquid medium of which water is a major component. Thus, the term includes water per se as well as aqueous solutions and dispersions.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkoxyl, alkenyl, halo, haloalkyl, monocyclic aryl, or amino, such as, for example, phenyl, methylphenyl, methoxyphenyl, dimethylphenyl, trimethylphenyl, chlorophenyl, trichloromethylphenyl, triisobutyl phenyl, tristyrylphenyl, and aminophenyl.

As used herein, the term "aralkyl" means an alkyl group substituted with one or more aryl groups, more typically a $(C_1-C_{18})$alkyl substituted with one or more $(C_6-C_{14})$aryl substituents, such as, for example, phenylmethyl, phenylethyl, and triphenylmethyl.

As used herein, the term "aryloxy" means an oxy radical substituted with an aryl group, such as for example, phenyloxy, methylphenyl oxy, isopropylmethylphenyloxy.

The "bicyclo[d.e.f]" notation is used herein in reference to bicycloheptyl and bicycloheptenyl ring systems in accordance with the von Baeyer system for naming polycyclic compounds, wherein a bicyclic system is named by the prefix "bicyclo-" to indicate number of rings in the system, followed by a series of three arabic numbers, listed in descending numerical order, separated by full stops, and enclosed in square brackets, to indicate the respective number of skeletal atoms in each acyclic chain connecting the two common atoms (the "bridgehead atoms"), excluding the bridgehead atoms. A bridgehead atom is any skeletal atom of the ring system bonded to three or more skeletal atoms (excluding hydrogen). A bicyclic system (which comprises the main ring and main bridge only) is named by: the prefix bicyclo- (indicating the number of rings); numbers indicating the bridge lengths (i.e. number of skeletal atoms excluding the bridgehead atoms) separated by full stops and placed in square brackets. The three numbers are cited in decreasing order of size (e.g. [3.2.1]); the name of the hydrocarbon indicating the total number of skeletal atoms. For example, bicyclo[3.2.1] octane is the name for the structure of Formula I.

 I

As used herein, the terminology "($C_x$-$C_y$)" in reference to an organic group, wherein x and y are each integers, indicates that the group may contain from x carbon atoms to y carbon atoms per group.

As used herein, the term "cycloalkenyl" means an unsaturated hydrocarbon radical, typically an unsaturated ($C_5$-$C_{22}$) hydrocarbon radical, that contains one or more cyclic alkenyl rings and which may optionally be substituted on one or more carbon atoms of the ring with one or two ($C_1$-$C_6$)alkyl groups per carbon atom, such as cyclohexenyl, cycloheptenyl, and "bicycloalkenyl" means a cycloalkenyl ring system that comprises two condensed rings, such as bicycloheptenyl.

As used herein, the term "cycloalkyl" means a saturated hydrocarbon radical, more typically a saturated ($C_5$-$C_{22}$) hydrocarbon radical, that includes one or more cyclic alkyl rings, which may optionally be substituted on one or more carbon atoms of the ring with one or two ($C_1$-$C_6$)alkyl groups per carbon atom, such as, for example, cyclopentyl, cycloheptyl, cyclooctyl, and "bicyloalkyl" means a cycloalkyl ring system that comprises two condensed rings, such as bicycloheptyl.

As used herein, an indication that a composition is "free" of a specific material means the composition contains no measurable amount of that material.

As used herein, the term "heterocyclyl" means a saturated or unsaturated organic radical that comprises a ring or condensed ring system, typically comprising from 4 to 16 ring atoms per ring or ring system, wherein such ring atoms comprise carbon atoms and at least one heteroatom, such as for example, O, N, S, or P per ring or ring system, which may optionally be substituted on one or more of the ring atoms, such as, for example, thiophenyl, benzothiphenyl, thianthrenyl, pyranyl, benzofuranyl, xanthenyl, pyrrolidinyl, pyrrolyl, pyradinyl, pyrazinyl, pyrimadinyl, pyridazinyl, indolyl, quinonyl, carbazolyl, phenathrolinyl, thiazolyl, oxazolyl, phenoxazinyl, or phosphabenzenyl.

As used herein, the term "hydroxyalkyl" means an alkyl radical, more typically a ($C_1$-$C_{22}$)alkyl radical, that is substituted with one or more hydroxyl groups, such as for example, hydroxymethyl, hydroxyethyl, hydroxypropyl, and hydroxydecyl.

As used herein, the terminology "hydrophobic surface" means a surface that exhibits a tendency to repel water and to thus resist being wetted by water, as evidenced by a water contact angle of greater than or equal to 70°, more typically greater than or equal to 90°, and/or a surface free energy of less than or equal to about 40 dynes/cm.

As used herein, the terminology "hydrophilic surface" means a surface that exhibits an affinity for water and to thus be wettable by water, as evidenced by a water contact angle of less than 70°, more typically less than 60° and/or a surface energy of greater than about 40 dynes/cm, more typically greater than or equal to about 50 dynes/cm.

As used herein in reference to a hydrophobic surface, the term "hydrophilizing" means rendering such surface more hydrophilic and thus less hydrophobic, as indicated by a decreased water contact angle. One indication of increased hydrophilicity of a treated hydrophobic surface is a decreased water contact angle with a treated surface compared to the water contact angle with an untreated surface.

As used herein the term "(meth)acrylate" refers collectively and alternatively to the acrylate and methacrylate and the term "(meth)acrylamide" refers collectively and alternatively to the acrylamide and methacrylamide, so that, for example, "butyl(meth)acrylate" means butyl acrylate and/or butyl methacrylate.

As used herein, "molecular weight" in reference to a polymer or any portion thereof, means to the weight-average molecular weight ("$M_w$") of said polymer or portion, wherein $M_w$ of a polymer is a value measured by gel permeation chromatography, static light scattering, viscometry, or a number of other standard techniques and $M_w$ of a portion of a polymer is a value calculated according to known techniques from the amounts of monomers, polymers, initiators and/or transfer agents used to make the said portion.

As used herein, the indication that a radical may be "optionally substituted" or "optionally further substituted" means, in general, that is unless further limited, either explicitly or by the context of such reference, that such radical may be substituted with one or more inorganic or organic substituent groups, such as, for example, alkyl, alkenyl, aryl, aralkyl, alkaryl, a hetero atom, or heterocyclyl, or with one or more functional groups that are capable of coordinating to metal ions, such as hydroxyl, carbonyl, carboxyl, amino, imino, amido, phosphonic acid, sulphonic acid, or arsenate, or inorganic and organic esters thereof, such as, for example, sulphate or phosphate, or salts thereof.

As used herein, "parts by weight" or "pbw" in reference to a named compound refers to the amount of the named compound, exclusive, for example, of any associated solvent. In some instances, the trade name of the commercial source of the compound is also given, typically in parentheses. For example, a reference to "10 pbw cocoamidopropylbetaine ("CAPB", as Mirataine BET C-30)" means 10 pbw of the actual betaine compound, added in the form of a commercially available aqueous solution of the betaine compound having the trade name "Mirataine BET C-30", and exclusive of the water contained in the aqueous solution.

As used herein, an indication that a composition is "substantially free" of a specific material, means that the composition contains no more than an insubstantial amount of that material, and an "insubstantial amount" means an amount that does not measurably affect the desired properties of the composition.

As used herein, the term "surfactant" means a compound that reduces surface tension when dissolved in water.

As used herein in reference to a component of an aqueous composition, the terminology "water insoluble or partially water-soluble components" means that the component is present in the aqueous composition at a concentration above the solubility limit of the component so that, in the case of a water insoluble component, the component remains substantially non-dissolved in the aqueous composition and, in the case of a partially water-soluble component, at least a portion of such component remains undissolved in the aqueous composition. The water insoluble or partially water-soluble components may, for example, be in the form of solid particles, of continuous or discontinuous liquid phases, such as oil droplets, or of discontinuous gas phases, such as air bubbles.

As used herein, the term "opaque" means not completely transparent to light and ranges from a hazy translucent appearance through a turbid appearance to a uniform, saturated white appearance.

Crosslinked Alkali Swellable Acrylate Copolymer

The compositions of the present invention may employ as a freeze thaw prevention agent a crosslinked polyacrylate alkali swellable polymer. The crosslinked alkali swellable acrylate copolymer comprises from about 20% to about 80% by weight of at least one carboxylic acid monomer comprising acrylic acid, methacrylic acid, itaconic acid, fumaric acid, crotonic acid, aconitic acid, or maleic acid, or combinations thereof; from about 80% to about 15% by weight of at least one alpha, beta-ethylenically unsaturated monomer; and from about 0.01 to about 5% by weight of at least one polyunsaturated compound useful in forming a partially or substantially crosslinked three dimensional network, wherein the at least one alpha, beta-ethylenically unsaturated monomer has the formula: $CH_2=CXY$, wherein X is H and Y is —COOR, —$C_6H_4R'$, —CN, —$CONH_2$, —Cl, —$NC_4H_6O$, $NH(CH_2)_3COOH$, —$NHCOCH_3$, —$CONHC(CH_3)_3$, —CO—$N(CH_3)_2$;

or X is $CH_3$ and Y is —COOR, —$C_6H_4R'$, —CN, or —$CH=CH_2$;

or X is Cl and Y is Cl, wherein R is $C_1$-$C_{18}$ alkyl, or hydroxy $C_2$-$C_{18}$ alkyl, R' is H or $C_1$-$C_{18}$ alkyl; or has the formula: $CH_2=CH(OCOR_1)$, wherein $R_1$ is $C_1$-$C_{18}$ alkyl; or has the formula: $CH_2=CH_2$ or $CH_2=CHCH_3$.

Typically the crosslinked alkali swellable acrylate copolymer has a molecular weight of over 30,000 grams/mol, more typically 30,000 to 1,000,000 grams/mol or 30,000 to 500,000 grams/mol.

Typically, the crosslinked alkali swellable acrylate copolymer is derived from: a. about 35% to about 65% by weight of acrylic acid or methacrylic acid, or combinations thereof, b. about 65% to about 35% by weight of ethylacrylate, or methylacrylate, or combinations thereof, and c. about 0.03% to about 3% by weight of polyalkenyl ethers of sucrose or polyalcohols; or trimethylolpropane tri(meth)acrylate, glycidyl ethacrylate, N-methylolacrylamide, or combinations thereof. A preferred crosslinked alkali swellable acrylate copolymer is LUBRIZOL CARBOPOL AQUA SF1.

Acrylate Co-Polymer

A polymer may be derived from at least one co-monomer and at least one polymerizable reactive alkoxylated acrylate monomer having the structural formula IA or IB:

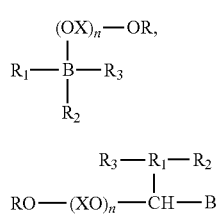

IA

IB wherein B is a 5 or 6 membered cycloalkyl ring, or a single ring aromatic hydrocarbon having a 6 membered ring, R1, R2 and R3 are independently selected from the group consisting of structural formula IC, ID, IE and IF:

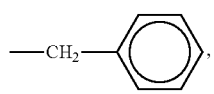

IC

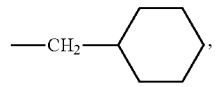

ID

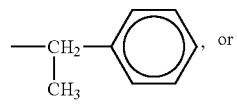

IE

, or

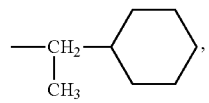

IF with the proviso that at most one of R1, R2 and R3 is —H, wherein, X is at least one member of the group consisting of $C_2H_4$, $C_3H_6$, and $C_4H_8$; n is 1-100, more typically, 4 to 40 or 8 to 25;

wherein R is an ethylenically unsaturated group.

Typically, R is selected from the group consisting of acrylate, or $C_1$-$C_6$ alkyl acrylate, e.g., methacrylate, allyl, vinyl, maleate, itaconate or fumarate, preferably R is acrylate or methacrylate.

Suitable polymerizable functional groups R include, for example, acrylo, methacrylo, acrylamido, methacrylamido, diallylamino, allyl ether, vinyl ether, α-alkenyl, maleimido, styrenyl, and α-alkyl styrenyl groups.

For example, suitable polymerizable functional groups R have the chemical structure: $RCH=C(R')COO$—, wherein if R is H, then R' is H, $C_1$-$C_4$ alkyl, or —$CH_2COOX$; if R is —C(O)OX, then R' is H or —$CH_2C(O)OX$; or if R is $CH_3$, then R' is H and X is H or $C_1$-$C_4$ alkyl.

For example, other suitable polymerizable functional groups R have the chemical structure: —HC=CYZ, wherein Y is H, $CH_3$, or Cl; Z is CN, Cl, —COOR', —$C_6H_4R'$, —COOR, or —HC=$CH_2$; R is $C_1$-$C_8$ alkyl or $C_2$-$C_8$ hydroxy alkyl; R' is H, Cl, Br, or $C_1$-$C_4$ alkyl, and R" is $C_1$-$C_8$ alkyl.

Preferably the monomer has the formula IBa:

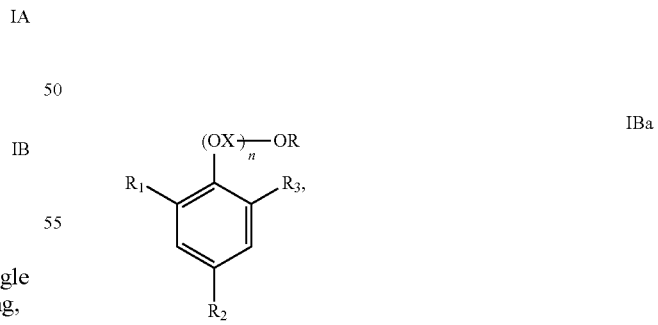

IBa wherein, R, R1, R2, R3, X and n are as defined for the structure of formula IA. If desired, the aromatic ring shown in structural formula IBa may be saturated. More preferably, for this embodiment the monomer is a polymerizable reactive alkoxylated tristyrylphenol having the structural formula ICa:

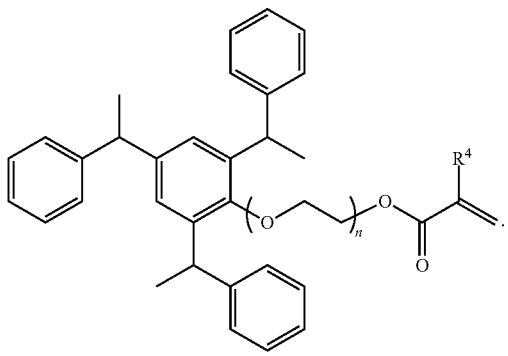

ICa wherein, n is 1-100, more typically, 4 to 40 or 8 to 25;

$R^4$ is a member of the group H, or C1-C6 alkyl, for example, CH3 or C2H5.

However, if desired, the ethylene oxide group shown in structural formula ICa may be replaced with the above discussed —(OX)— group of formula IA, and the —C(O)—CHR$^4$—CH$_2$ end group may be replaced by allyl, vinyl, maleate, itaconate or fumarate. Thus, the reactive polymerizable alkoxylated tristyrylphenol monomer typically has a tristyrylphenol portion, an alkylene oxide portion and a reactive substituted or unsubstituted acrylic end group for polymerization.

For example, a typical embodiment of monomeric unit of Formula IA is as shown in formula ICa, wherein the polymerizable reactive alkoxylated monomer comprises a polymerizable reactive ethoxylated tristyrylphenol having the above-mentioned structural formula ICa wherein, n is in the range of 1-100, and $R^4$ is selected from the group consisting of H and C1-C6 alkyl.

For example, a typical embodiment of monomeric unit derived from opening the C to C double bond of the ethylenically unsaturated group of the monomer of Formula IBa to form a polymerizable group is shown in formula Da.

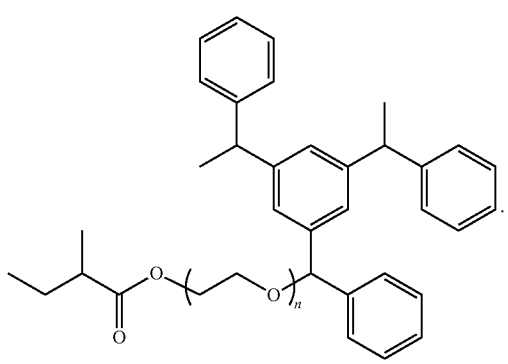

IDa wherein n ranges from 5 to 50.

When reactive polymerizable alkoxylated monomer is copolymerized into the backbone of the polymer, the polymer is made from a mixture wherein the reactive alkoxylated monomer is 1 to 10 parts per 100 parts by weight of monomers used to form the copolymer, more typically 2 to 8 parts per 100 parts by weight of monomers used to form the copolymer.

The resulting aqueous coating compositions of the invention acrylate co-polymer of formulas IA or IB include less than 2.0% by weight and preferably less than 1.0% by weight of anti-freeze agents based on the total weight of the aqueous composition. More preferably, the aqueous compositions are substantially free of anti-freeze agents.

Hydrophobically Modified Alkali-Soluble Polymer

The present invention includes compositions comprising a surface active agent and a Hydrophobically modified Alkali-Soluble polymer comprising yield bringing monomers with viscosity bringing monomers to provide freeze thaw stability to surfactant systems, particularly to structured surfactant systems. Typically the hydrophobically modified alkali-soluble polymer is a hydrophobically modified alkali-soluble emulsion (HASE) polymer.

In a first aspect, this HASE polymer comprises a chain of monomeric units. The polymer is a macromolecule having a relatively high molecular mass that comprises chains of multiple repetitions of the monomeric units, which are derived, actually or conceptually, from molecules of relatively low molecular mass and are connected to form a linear, branched, or network structure. The polymer typically has a linear or branched structure, more typically single strand linear or branched structure. In one embodiment, a polymer having a predominantly single strand linear or branched structure is lightly crosslinked to form a polymer network having a low density of crosslinks. As used herein the term "single strand" in regard to a polymer means monomeric units of the polymer are connected such that adjacent monomeric units are joined to each other through two atoms, one on each of the adjacent monomeric units.

Although this polymer is described as a HASE polymer it is not necessary to make a polymer of this structure by emulsion polymerization. The polymer may also be made by solution polymerization and comes within the invention whether made by emulsion polymerization or solution polymerization.

The polymer may typically be regarded as having a "backbone", or main polymer chain, from which all branches and substituent groups of the polymer may be regarded as being pendant. Where two or more chains of the polymer could equally be considered to be the main chain of the polymer, that chain is selected as the main chain which leads to the simplest representation of the polymer molecule. The monomeric units of the polymer may be arranged in random, alternating, tapered, or block sequence along the polymer chain.

The hydrophobically modified alkali-soluble acrylate copolymer typically has a weight average molecular weight of greater than or equal to about 30,000 grams per mole and comprises:

(a) one or more first monomeric units, each independently comprising at least one bicycloheptyl-polyether, bicycloheptenyl-polyether or branched ($C_5$-$C_{50}$)alkyl-polyether group per monomeric unit, wherein the bicycloheptyl-polyether or bicycloheptenyl-polyether group may optionally be substituted on one or more ring carbon atoms by one or two ($C_1$-$C_6$)alkyl groups per carbon atom, (b) one or more second monomeric units, each independently comprising at least one pendant linear or branched ($C_5$-$C_{50}$)alkyl-polyether group per monomeric unit, provided that the first and second monomeric units cannot both comprise a branched ($C_5$-$C_{50}$)alkyl-polyether group, and (c) at least one polymerizable functional group per molecule of polymer.

In one embodiment, the polymer comprises:
(a) one or more first monomeric units, each independently comprising at least one at least one bicycloheptyl-polyether or bicycloheptenyl-polyether group per monomeric unit, and
(b) one or more second monomeric units, each independently comprising at least one pendant linear or branched ($C_5$-$C_{50}$)alkyl-polyether group per monomeric unit, and
(c) at least one polymerizable functional group per molecule of polymer, the polymer having a weight average molecular weight of greater than or equal to about 30,000 grams per mole, typically the polymer has a weight average molecular weight of greater than or equal to about 30,000 to 1,000,000 grams per mole or 30,000 to 500,000 grams per mole or 50,000 to 500,000 grams per mole.

In one embodiment, the polymer of the present invention comprises:
(a) one or more first monomeric units, each independently comprising at least one branched ($C_5$-$C_{50}$)alkyl-polyether group per monomeric unit, and
(b) one or more second monomeric units, each independently comprising at least one pendant linear ($C_5$-$C_{50}$)alkyl-polyether group per monomeric unit, and
(c) at least one polymerizable functional group per molecule of polymer,
the polymer having a weight average molecular weight of greater than or equal to about 30,000 grams per mole.

Typically the first and second specialty hydrophobic macro monomeric units (a) (b) are attached to the backbone comprising the at least one polymerizable functional group per molecule of polymer.

FIG. 1 shows an idealized diagram of the structure of this HASE polymer 1 having a polyelectrolyte backbone 2, hydrophobic groups 4 and PEO spacers 6.

Typically the at least one polymerizable functional group comprises third acid monomeric units, each independently comprising a carboxylic acid-functional substituent group, for example, Methacrylic Acid (MAA). Typically third acid monomeric units, each independently comprise at least one acid group per monomeric unit, for example, a sulfonic acid group, a phosphonic acid group, a phosphoric acid group, or a carboxylic acid-functional substituent group, for example, Methacrylic Acid (MAA).

The HASE polymer may also comprise fourth non-ionic monomeric units, each independently comprising a nonionic substituent group, for example Ethyl Acrylate (EA). A monomeric unit of Ethylene Oxide (EO) and/or Propylene Oxide (PO) typically connects the hydrophobic macro groups to the backbone as side chains. The MAA hydrophilic segments provide solubility. The slightly insoluble EA segments enhance the thickening performance by promoting hydrophobic aggregations. The hydrophobic macro monomers are specialty monomers responsible for intra-/intermolecular associations. The poly(ethylene oxide) chain, usually 5-100 ethylene oxide units (typically 6-10 EO groups) and 0-5 propylene oxide units favor the intermolecular aggregation.

First Monomeric Unit for HASE Polymer

In one embodiment, the first monomeric units each independently comprise, per monomeric unit, at least one branched ($C_5$-$C_{50}$)alkyl or bicycloheptyl-polyether or bicycloheptenyl-polyether group according to structure (A.I):

(A.I).

In one embodiment, $R^{11}$ is bicyclo[d.e.f]heptyl or bicyclo[d.e.f]heptenyl, wherein d is 2, 3, or 4, e is 1 or 2, f is 0 or 1, and the sum of d+e+f=5, and wherein the bicyclo[d.e.f]heptyl or bicyclo[d.e.f]heptenyl may, optionally, be substituted on one or more of the ring carbon atoms by one or more ($C_1$-$C_6$) alkyl groups, $R^{12}$ is absent or is a bivalent linking group, $R^{13}$ is bivalent polyether group, and $R^{14}$ is absent or is a bivalent linking group.

Suitable bicycloheptyl- and bicycloheptenyl-moieties may be derived from, for example, terpenic compounds having core (non-substituted) 7 carbon atom bicyclic ring systems according to structures (A.II)-(A.V.b):

(A.II) [2.2.1]

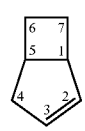

(A.III) [3.2.0]

(A.IV.a) [3.1.1]

(A.IV) [3.1.1]

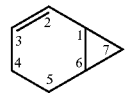

(A.V) [4.1.0]

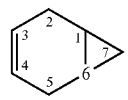

(A.V.b) [4.1.0]

In one embodiment, $R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more ($C_1$-$C_6$)alkyl groups.

More typically, $R^{11}$ is:

a bicyclo[2.2.1]heptyl or bicyclo[2.2.1]heptenyl group bonded to $R^2$, if present, or to $R^3$, if $R^2$ is not present, via its carbon atom at the 2-position or 3-position and is typically substituted on its carbon atom at the 7 position by one or two ($C_1$-$C_6$)alkyl radicals, more typically by two methyl radicals, or a bicyclo[3.1.1]heptyl or bicyclo[3.1.1]heptenyl group bonded to $R^2$, if present, or to $R^3$, if $R^2$ is not present, via its carbon atom at the 2-position or 3-position and is typically substituted on its carbon atom at the 6-position or 7-position by one or two ($C_1$-$C_6$)alkyl radicals, more typically by two methyl radicals.

In one embodiment, $R^{11}$ is branched ($C_5$-$C_{50}$) alkyl group, more typically a branched alkyl group according to structure (a.VI):

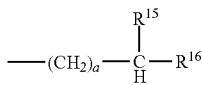
(A.VI)

wherein:
$R^{15}$ and $R^{16}$ are each independently ($C_1$-$C_{48}$)alkyl, and
a is an integer of from 0 to 40,
provided that $R^{11}$, that is, $R^{15}$, $R^{16}$ and the —$(CH_2)_a$— radical taken together, comprises a total of from about 5 to about 50, more typically about 12 to about 50, carbon atoms;
$R^{12}$ is absent or is a bivalent linking group,
$R^{13}$ is bivalent polyether group, and
$R^{14}$ is absent or is a bivalent linking group.

More typically, $R^{12}$ is O, a bivalent hydrocarbon group, even more typically a methylene group or chain of from 2 to 6 methylene units, or a bivalent alkyleneoxyl group, such as ethyleneoxy. In one embodiment, $R^{12}$ is according to structure (A.VII):

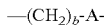
(A.VII)

wherein A is O or absent, and b is an integer of from 1 to 6.

More typically, $R^{13}$ is a bivalent polyether group comprising a linear chain of from 2 to 100 units, each of which may independently be ($C_2$-$C_4$)oxyalkylene, more typically, ($C_2$-$C_3$)oxyalkylene. In one embodiment, $R^{13}$ is a bivalent polyether group comprising a chain of from 2 to 100 polymerized oxyethylene units and oxypropylene units, which may be arranged alternately, randomly, or in blocks. In one embodiment, $R^{13}$ is a bivalent polyether group comprising a block of polyoxyethylene units and a block of oxypropylene units, more typically, a block of polyoxyethylene units and a block of oxypropylene units, wherein the block of oxypropylene units is disposed between and links the block of oxyethylene units and the $R^{12}$ substituent, if present, or the $R^{11}$ substituent, if $R^{12}$ is not present.

In one embodiment, $R^{13}$ is according to structure (A.VIII):

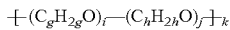
(A.VIII)

wherein:
g and h are independently integers of from 2 to 5, more typically 2 or 3,
each i is independently an integer of from 1 to about 80, more typically from 1 to about 50,
each j is independently an integer of from 0 to about 80, more typically from 1 to about 50,
k is an integer of from 1 to about 50, provided that the product obtained by multiplying the integer k times the sum of i+j is from 2 to about 100.

If i≠0, j≠0, and g≠h, the respective —($C_pH_{2p}O$)— and (—$C_qH_{2q}O$)— oxylakylene units may be arranged randomly, in blocks, or in alternating order.

In one embodiment,
g=2,
h=3,
i is an integer of from 1 to 50, more typically 10 to 40, and even more typically from 15 to 30,
j is an integer of from 1 to 30, more typically from 2 to 20, and even more typically from about 2 to about 10, and
k=1.

In one embodiment, $R^{14}$ is O, —$(CH_2)_n$—O—, or is according to structure (A.IX):

(A.IX)

wherein:
n is an integer of from 1 to 6,
A is O or $NR^{17}$, and
$R^{17}$ is H or ($C_1$-$C_4$)alkyl.

The first monomeric units may be made by known synthetic techniques, such as, for example, by grafting of one or more groups according to structure (I) onto a polymer backbone, such as a hydrocarbon polymer backbone, a polyester polymer backbone, or a polysaccharide polymer backbone, or by copolymerization, with, for example, the second monomer and third monomer described below, of at least one first monomer selected from monomers that comprise a reactive functional group and at least one group according to structure (I) per molecule.

In one embodiment, the first monomeric units are derived from at least one first monomer selected from monomers that comprise a reactive functional group and at least one group according to structure (I) per molecule.

In one embodiment, the reactive functional group of the first monomer is an ethylenically unsaturated group and the first monomer selected from ethylenically unsaturated monomers that comprise at least one site of ethylenic unsaturation, more typically, an α-, β-unsaturated carbonyl moiety, and least one group according to structure (I) per molecule.

In one embodiment, the first monomer comprises one or more compounds according to structure (A.X):

$$R^{18}\text{-}R^{14}\text{-}R^{13}\text{-}R^{12}\text{-}R^{11} \quad (A.X)$$

wherein:
$R^{11}$, $R^{12}$, $R^{13}$, and $R^{14}$ are each as described above, and
$R^{18}$ is a moiety having a site of ethylenic unsaturation.

In one embodiment, the compound according to structure (A.X) is an α-, β-unsaturated carbonyl compound.

In one embodiment, $R^{18}$ is according to structure (A.XI):

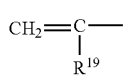
(A.XI)

wherein $R^{19}$ is H or ($C_1$-$C_4$)alkyl.

In one embodiment, the first monomer selected from monomers according to structure (A.XII):

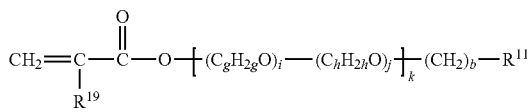
(A.XII)

wherein:
$R^{11}$ is bicyclo[d.e.f]heptyl or bicyclo[d.e.f]heptenyl wherein d is 2, 3, or 4, e is 1 or 2, f is 0 or 1, and the sum of d+e+f=5, and which may, optionally, be substituted on one or more of the ring carbon atoms by one or more ($C_1$-$C_6$)alkyl groups, and
$R^{19}$, b, g, h, i, j, and k are each as defined above.

In one embodiment, the first monomer comprises one or more compounds according to structure (A.XIII):

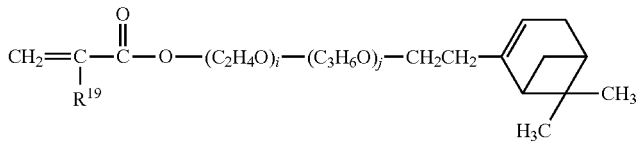

(A.XIII)

wherein i, j, and $R^{19}$ are each as described above, and, more typically, i is an integer of from 10 to 40, and even more typically from 15 to about 30, or from about 20 to about 30, and j is an integer of from 1 to 20, and even more typically from about 2 to about 10.

In another embodiment, the first monomer comprises one or more compounds according to structure (A.XIV):

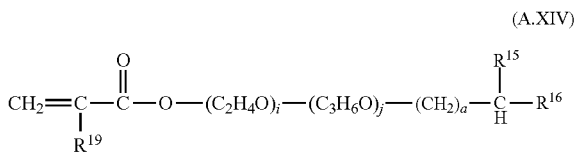

(A.XIV)

wherein a, i, j, and $R^{15}$, $R^{16}$, and $R^{19}$ are each as described above.

Suitable monomer may be made by known synthetic methods. For example, a bicycloheptenyl intermediate compound (A.XV), known as "Nopol":

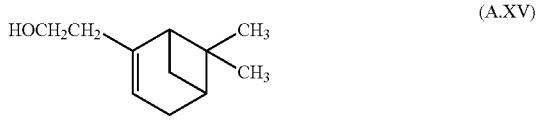

(A.XV)

is made by reacting β-pinene with formaldehyde, and a bicycloheptyl intermediate compound (XVI), known as "Arbanol":

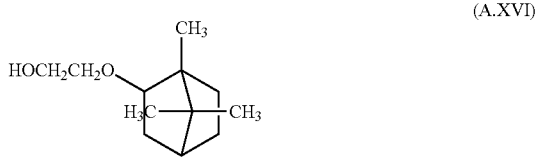

(A.XVI)

is made by isomerization of α-pinene to camphene and ethoxyhydroxylation of the camphene.

The bicycloheptyl- or bicycloheptenyl-intermediate may then be alkoxylated by reacting the bicycloheptyl- or bicycloheptenyl intermediate with one or more alkylene oxide compounds, such as ethylene oxide or propylene oxide, to form a bicycloheptyl-, or bicycloheptenyl-polyether intermediate. The alkoxylation may be conducted according to well known methods, typically at a temperature in the range of about 100° to about 250° C. and at a pressure in the range of from about 1 to about 4 bars, in the presence of a catalyst, such as a strong base, an aliphatic amine, or a Lewis acid, and an inert gas, such as nitrogen or argon.

The bicycloheptyl-, or bicycloheptenyl-polyether monomer may then be formed from the bicycloheptyl- or bicycloheptenyl-polyether intermediate by addition of a moiety containing an ethylenically unsaturated group to the bicycloheptyl- or bicycloheptenyl-polyether intermediate, by, for example, esterification, under suitable reaction conditions, of the bicycloheptyl- or bicycloheptenyl-polyether intermediate with, for example, methacrylic anhydride.

Alternatively, a monomer comprising a ethylenically unsaturated group, such as for example, a polyethylene glycol monomethacrylate, which may optionally be further alkoxylated, may be reacted with the bicycloheptyl- or bicycloheptenyl-intermediate to form the bicycloheptyl-, or bicycloheptenyl-polyether monomer.

Second Monomeric Unit for HASE Polymer

In one embodiment, the second monomeric units each independently comprise, per monomeric unit, at least one group according to structure (A.XVII):

(A.XVII)

wherein:

$R^{21}$ is linear or branched $(C_5-C_{50})$alkyl, hydroxyalkyl, alkoxyalkyl, aryl, or aryalkyl, $R^{22}$ is a bivalent polyether group, $R^{23}$ is absent or is a bivalent linking group.

In one embodiment, $R^{21}$ is linear or branched $(C_5-C_{40})$ alkyl, more typically linear or branched $(C_{10}-C_{40})$alkyl, even more typically, linear or branched $(C_{16}-C_{40})$alkyl, and still more typically linear or branched $(C_{16}-C_{30})$alkyl. In one embodiment, $R^{21}$ is tridecyl, tetradecyl, pentadecyl, hexadecyl, heptadecyl, octadecyl, nonadecyl, eicosyl, heneicosyl, behenyl, tricosyl, tetracosyl, pentacosyl, hexacosyl, heptacosyl, octacosyl, nonacosyl, triacontyl, dotriacontyl, tritriacontyl, tetratriacontyl, pentatriacontyl, hexatriacontyl, heptatriacontyl, octatriacontyl, nonatriacontyl, or tetracontyl, more typically, hexadecyl, heptadecyl, octadecyl, nonadecyl, eicosyl, or behenyl.

In embodiment $R^{21}$ is hydroxyalkyl, such as, for example, hydroxyhexadecyl, hydroxyoctadecyl, or hydroxyeicosyl, or alkoxyalkyl, such as for example, methoxyhexadecyl, methoxyoctadecyl, or methoxyeicosyl.

In embodiment $R^{21}$ is aryl, such as, for example, phenyl, methylphenyl, methoxyphenyl, dibutylphenyl, triisobutylphenyl, or tristyrylphenyl, or aralkyl, such as phenylmethyl, phenylethyl, or triphenylmethyl.

In one embodiment, the second monomeric units each independently comprise at least one group according to structure (A.XVII) above wherein $R^{21}$ is a linear $(C_5-C_{50})$alkyl group.

In one embodiment, the second monomeric units each independently comprise at least one group according to structure (A.XVII) above wherein $R^{21}$ is a branched $(C_5-C_{50})$alkyl group, more typically a branched $(C_5-C_{50})$alkyl group according to structure (A.VI) above.

In one embodiment, the second monomeric units comprise a mixture of second monomeric units that each independently comprise at least one group according to structure (XVII) above wherein $R^{21}$ is a linear ($C_5$-$C_{50}$)alkyl group and second monomeric units that each independently comprise at least one group according to structure (XVII) above wherein $R^{21}$ is a branched ($C_5$-$C_{50}$)alkyl group, more typically a branched ($C_5$-$C_{50}$)alkyl group according to structure (A.VI) above.

In one embodiment, $R^{22}$ is a bivalent polyether group comprising a linear chain of from 2 to 100 units, each of which may independently be ($C_2$-$C_4$)oxyalkylene, more typically, ($C_2$-$C_3$)oxyalkylene. In one embodiment, $R^{22}$ is a bivalent polyether group comprising a chain of from 2 to 100 polymerized oxyethylene units.

In one embodiment, $R^{22}$ is according to structure (A.XVIII):

   (A.XVIII)

wherein:

p and q are independently integers of from 2 to 5, more typically 2 or 3, each r is independently an integer of from 1 to about 80, more typically from 1 to about 50, each s is independently an integer of from 0 to about 80, more typically from 0 to about 50, t is an integer of from 1 to about 50, provided that the product obtained by multiplying the integer t times the sum of r+s is from 2 to about 100.

If r≠0, s≠0, and p≠q, the respective —($C_pH_{2p}O$)— and —($C_qH_{2q}O$)— oxylakylene units may be arranged randomly, in blocks, or in alternating order.

In one embodiment, p=2, q=3, r is an integer of from 1 to 50, more typically 5 to 45, and even more typically from 10 to about 40, s is an integer of from 1 to 30, more typically from 2 to 20, and even more typically from about 2 to about 10, and t=1

In another embodiment, p=2, r is an integer of from 1 to 50, more typically 5 to 45, and even more typically from 10 to about 40, s is 0, and t=1.

In one embodiment, $R^{23}$ is O, —($CH_2$)$_n$—O— wherein n is an integer of from 1 to 6, or is according to structure (IX) above, wherein A is O or $NR^{17}$, and $R^{17}$ is H or ($C_1$-$C_4$)alkyl.

The second monomeric units may be made by known synthetic techniques, such as, for example, by grafting of one or more groups according to structure XVII onto a polymer backbone, such as a hydrocarbon polymer backbone, a polyester polymer backbone, or a polysaccharide polymer backbone, or by copolymerization, with, for example, the above-described first monomer and the third monomer described below, of at least one second monomer selected from monomers that comprise a reactive functional group and at least one group according to structure (XVII) per molecule and that are copolymerizable with the first monomer.

In one embodiment, the second monomeric units are derived from at least one second monomer that comprises a reactive functional group and at least one group according to structure (XVII) per molecule and that are copolymerizable with the first monomer.

In one embodiment, the reactive group of the second monomer is an ethylenically unsaturated group and the second monomer is an ethylenically unsaturated monomer comprises at least one site of ethylenic unsaturation, more typically, an α-, β-unsaturated carbonyl moiety, and at least one group according to structure (XVII) per molecule and that are copolymerizable with the first monomer.

In one embodiment, the second monomer comprises one or more compounds according to structure (A.XIX):

   (A.XIX)

wherein:

$R^{21}$, $R^{22}$, and $R^{23}$ are each as described above, and $R^{24}$ is a moiety having a site of ethylenic unsaturation.

In one embodiment, the compound according to structure (XIX) is an α-, β-unsaturated carbonyl compound. In one embodiment, $R^{23}$ is according to structure (A.XI) above.

In one embodiment, the second monomer comprises one or more compounds according to structure (A.XX):

wherein $R^{21}$ is linear or branched ($C_5$-$C_{50}$)alkyl, hydroxyalkyl, alkoxyalkyl, aryl, or aralkyl, $R^{25}$ is methyl or ethyl, and p, q, r, s, and t are each as described above.

In one embodiment, the second monomer comprises one or more compounds according to structure (A.XX) wherein $R^{21}$ is linear ($C_{16}$-$C_{22}$)alkyl.

In one embodiment, the second monomer comprises one or more compounds according to structure (A.XX) wherein $R^{21}$ is a branched ($C_5$-$C_{50}$)alkyl group, more typically a branched ($C_5$-$C_{50}$)alkyl group according to structure (A.VI) above.

In one embodiment, the second monomer comprises one or more compounds according to structure (A.XX) wherein p=2, s=0, and t=1.

In one embodiment, the second monomer comprises one or more compounds according to structure (A.XX) wherein $R^{21}$ is linear ($C_{16}$-$C_{22}$)alkyl, $R^{24}$ is methyl or ethyl, p=2, s=0, and t=1.

Suitable ethylenically unsaturated second monomers include:

alkyl-polyether (meth)acrylates that comprise at least one linear or branched ($C_5$-$C_{40}$)alkyl-polyether group per molecule, such as hexyl polyalkoxylated (meth)acrylates, tridecyl polyalkoxylated (meth)acrylates, myristyl polyalkoxylated (meth)acrylates, cetyl polyalkoxylated (meth)acrylates, stearyl polyalkoxylated (methyl)acrylates, eicosyl polyalkoxylated (meth)acrylates, behenyl polyalkoxylated (meth)acrylates, melissyl polyalkoxylated (meth)acrylates, tristyrylphenoxyl polyalkoxylated (meth)acrylates, and mixtures thereof, alkyl-polyether (meth)acrylamides that comprise at least one ($C_5$-$C_{40}$)alkyl-polyether substituent group per molecule, such as hexyl polyalkoxylated (meth)acrylamides, tridecyl polyalkoxylated (meth) acrylamides, myristyl polyalkoxylated (meth) acrylamides, cetyl polyalkoxylated (meth)acrylamides, stearyl polyalkoxylated (methyl)acrylamides, eicosyl polyalkoxylated (meth) acrylamides, behenyl polyalkoxylated (meth) acrylamides, melissyl polyalkoxylated (meth) acrylamides and mixtures thereof.

alkyl-polyether vinyl esters, alkyl-polyether vinyl ethers, or alkyl-polyether vinyl amides that comprise at least one ($C_5$-$C_{40}$)alkyl-polyether substituent group per molecule such as vinyl stearate polyalkoxylate, myristyl polyalkoxylated vinyl ether, and mixtures thereof, as well as mixtures of any of the above alkyl-polyether acrylates, alkyl-polyether methacrylates, alkyl-polyether acrylamides, alkyl-polyether methacrylamides, alkyl-polyether vinyl esters, alkyl-polyether vinyl ethers, and/or alkyl-polyether vinyl amides.

In one embodiment, the second monomer comprises one or more alkyl-polyalkoxylated (meth)acrylates that comprise one linear or branched ($C_5$-$C_{40}$)alkyl-polyethoxylated group, more typically ($C_{10}$-$C_{22}$)alkyl-polyethoxylated group per molecule, such as decyl-polyethoxylated (meth)acrylates, tridecyl-polyethoxylated (meth)acrylates, myristyl-polyethoxylated (meth)acrylates, cetyl-polyethoxylated (meth)acrylates, stearyl-polyethoxylated (methyl)acrylates, eicosyl-polyethoxylated (meth)acrylates, behenyl-polyethoxylated (meth)acrylates, even more typically decyl-polyethoxylated methacrylates, tridecyl-polyethoxylated methacrylates, myristyl-polyethoxylated methacrylates, cetyl-polyethoxylated methacrylates, stearyl-polyethoxylated methylacrylates, eicosyl-polyethoxylated methacrylates, behenyl-polyethoxylated methacrylates, and mixtures thereof.

Third Monomeric Unit for HASE Polymer

In one embodiment, the polymer of the present invention further comprises third monomeric units, each independently comprising at least one acid group per monomeric unit.

In one embodiment, the third monomeric units each independently comprise, per monomeric unit, at least one group according to structure (A.XXI):

$$—R^{32}\text{-}R^{31} \quad \text{(A.XXI)}$$

wherein
$R^{31}$ is a moiety that comprises at least one carboxylic acid, sulfonic acid, or phosphoric acid group, and
$R^{32}$ is absent or is a bivalent linking group.

In one embodiment, $R^{32}$ is O, —$(CH_2)_n$—O—, or is according to structure (A.IX) above, wherein n is an integer of from 1 to 6, A is O or $NR^{17}$, and $R^{17}$ is H or ($C_1$-$C_4$)alkyl.

In one embodiment, the third monomeric units each independently comprise one or two carboxy groups per monomeric unit and may, if the third monomeric unit comprises a single carboxy group, further comprise an ester group according to —$CH_2COOR^{33}$, wherein $R^{33}$ is alkyl, more typically, ($C_1$-$C_6$)alkyl.

The third monomeric units may be made by known synthetic techniques, such as, for example, by grafting of one or more groups according to structure (A.XXI) onto a polymer backbone, such as a hydrocarbon polymer backbone, a polyester polymer backbone, or a polysaccharide polymer backbone, or by polymerization, with, for example, the above described first and second monomers, of at least one third monomer selected from monomers that comprise a reactive functional group and at least one group according to structure (A.XXI) per molecule, and that are copolymerizable with the first and second monomers.

In one embodiment, the third monomeric units are derived from at least one third monomer that comprises a reactive functional group and at least group according to structure (A.XXI) per molecule and is copolymerizable with the first and second monomers.

In one embodiment, the reactive functional group of the third monomer is an ethylenically unsaturated group and the third monomer is an ethylenically unsaturated monomer that comprises at least one site of ethylenic unsaturation, more typically, an α-, β-unsaturated carbonyl moiety, and at least one group according to structure (A.XXI) per molecule and is copolymerizable with the first and second monomers.

In one embodiment the third monomer comprises one or more ethylenically unsaturated monocarboxylic acid monomers according to structure (XXII):

$$R^{34}\text{-}R^{32}\text{-}R^{31} \quad \text{(A.XXII)}$$

wherein:
$R^{31}$ and $R^{32}$ are each as described above, and
$R^{34}$ is a moiety having a site of ethylenic unsaturation.

In one embodiment, the compound according to structure (A.XXII) is an α-, β-unsaturated carbonyl compound. In one embodiment, $R^{34}$ is according to structure (XI) above.

Suitable third monomers include, for example, ethylenically unsaturated carboxylic acid monomers, such as acrylic acid and methacrylic acid, ethylenically unsaturated dicarboxylic acid monomers, such ac maleic acid and fumaric acid, ethylenically unsaturated alkyl monoesters of dicarboxylic acid monomers, such as butyl methyl maleate, ethylenically unsaturated sulphonic acid monomers, such as vinyl sulfonic acid 2-acrylamido-2-methylpropane sulfonic acid, and styrene sulfonic acid, and ethylenically unsaturated phosphonic acid monomers, such as vinyl phosphonic acid and allyl phosphonic acid, salts of any thereof, and mixtures of any thereof. Alternatively, corresponding ethylenically unsaturated anhydride or acid chloride monomers, such as maleic anhydride, may be used and subsequently hydrolyzed to give a pendant moiety having two acid groups.

In one embodiment, the polymer of the present invention comprises third monomeric units derived from one or more third monomers selected from acrylic acid, methacrylic acid, and mixtures thereof. Methacrylic acid having the following formula A.XXIIa:

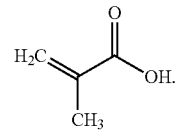

A.XXIIa

Fourth Monomeric Unit for HASE Polymer

In one embodiment, the polymer of the present invention further comprises one or more fourth monomeric units that differ from the first, second and third monomeric units.

In one embodiment, the fourth monomeric units each independently comprise, per monomeric unit, at least one group according to structure (XXIII):

$$—R^{42}\text{-}R^{41} \quad \text{(A.XXIII)}$$

wherein
$R^{41}$ is alkyl, hydroxyalkyl, alkoxyalkyl, cycloalkyl, aryl, aralkyl, or aryloxy, and
$R^{42}$ is absent or is a bivalent linking group.

In one embodiment, $R^{41}$ is ($C_1$-$C_{22}$)alkyl, ($C_1$-$C_{22}$)hydroxyalkyl, ($C_2$-$C_{22}$)alkoxyalkyl, ($C_6$-$C_{24}$)cycloalkyl, ($C_6$-$C_{40}$)aryl, or ($C_7$-$C_{40}$)aralkyl, more typically ($C_2$-$C_{12}$)alkyl.

In one embodiment, $R^{41}$ is ($C_1$-$C_{22}$)alkyl, more typically, ($C_1$-$C_{12}$)alkyl.

In one embodiment, $R^{42}$ is O, —$(CH_2)_n$—O—, wherein n is an integer of from 1 to 6, or is according to structure (IX) above, wherein A is O or $NR^{17}$, and $R^{17}$ is H or ($C_1$-$C_4$)alkyl.

The fourth monomeric units may be made by known synthetic techniques, such as, for example, by grafting of one or more groups according to structure (XXIII) onto a polymer backbone, such as a hydrocarbon polymer backbone, a polyester polymer backbone, or a polysaccharide polymer backbone, or by polymerization, with, for example, the above described first second, and third monomers, of at least one fourth monomer selected from monomers that comprise a reactive functional group and at least one group according to structure (A.XXIII) per molecule and that are copolymerizable with the first, second, and third monomers. Alternatively, the fourth monomeric units may simply be non-grafted portions of a polymer backbone, other portions of which have been grafted with groups according to structures (A.I), (A.XVII), and (A.XXI).

In one embodiment, the fourth monomeric units are derived from a fourth monomer that comprises a reactive functional group and a group according to structure (A.XXIII), and is copolymerizable with the first, second and third monomers.

In one embodiment, the reactive functional group of the fourth monomer is an ethylenically unsaturated group and the fourth monomer is an ethylenically unsaturated monomer comprising at least one site of ethylenic unsaturation, more typically, an α-, β-unsaturated carbonyl moiety and at least one group according to structure (A.XXIII) per molecule.

In one embodiment, the fourth monomer comprises one or more compounds according to structure (A.XXIV):

$$R^{43}\text{-}R^{42}\text{-}R^{41} \qquad \text{(A.XXIV)}$$

wherein:
$R^{41}$ and $R^{42}$ are each as described above, and
$R^{43}$ is a moiety having a site of ethylenic unsaturation.

In one embodiment, the compound according to structure (A.XXIV) is an α-, β-unsaturated carbonyl compound. In one embodiment, $R^{43}$ is according to structure (A.XI) above.

Suitable fourth monomers include unsaturated monomers at least one group according to structure XXIII per molecule, including (meth)acrylic esters such as: methyl(meth)acrylate, ethyl(meth)acrylate, butyl (meth)acrylate, isobutyl(meth)acrylate, cyclohexyl(meth)acrylate, 2-ethylhexyl (meth)acrylate, isodecyl(meth)acrylate, lauryl(meth)acrylate isobornyl (meth)acrylate, benzyl(meth)acrylate, hydroxyethyl(meth)acrylate, hydroxypropyl(meth)acrylate, methoxyethyl(meth)acrylate, ethoxyethyl (meth)acrylate, phenoxyethyl(meth)acrylate, tetrahydrofurfuryl(meth)acrylate, glycidyl(meth)acrylate, dimethylaminoethyl(meth)acrylate, diethylaminoethyl (meth)acrylate, tert-butylaminoethyl (meth)acrylate, and acetoxyethyl (meth)acrylate, (meth) acrylamides such as, (meth)acrylamide, N-methylol (meth) acrylamide, N-butoxyethyl(meth)acrylamide, N,N-dimethyl (meth)acrylamide, N-isopropyl(meth)acrylamide, N-tert-butyl (meth)acrylamide, N-tert-octyl(meth)acrylamide, and diacetone (meth)acrylamide, vinyl esters such as vinyl acetate, vinyl propionate, vinyl 2-ethylhexanoate, N-vinylamides such as: N-vinylpyrrolidione, N-vinylcaprolactam, N-vinylformamide, and N-vinylacetamide, and vinyl ethers such as, methyl vinyl ether, ethyl vinyl ether, butyl vinyl ether, and hydroxybutyl vinyl ether, and ethylenically unsaturated aryl compounds, such as styrene.

In one embodiment, the HASE polymer of the present invention is crosslinked. A crosslinked polymer can be made by, for example, reacting a mixture of first, second, and third monomers that also includes at least one fourth monomer having more than one reactive functional group, such as for example, more than one site of ethylenic unsaturation per molecule, that are copolymerizable with the other monomers of mixture In one embodiment, the fourth monomer comprises least one monomeric compound having more than one (meth)acrylic group per molecule, such as, for example, allyl methacrylate, ethylene glycol dimethacrylate, butylene glycol dimethacrylate, diallyl pentaerythritol, methylenebisacrylamide, pentaerythritol di-, tri- and tetra-acrylates, divinyl benzene, polyethylene glycol diacrylates, bisphenol A diacrylates, butanediol dimethacrylate, 2,2-dimethylpropanediol dimethacrylate, ethylene glycol dimethacrylate, phenylene diacrylate, or a mixture thereof. Ethyl acrylate having the formula A.XXIVa:

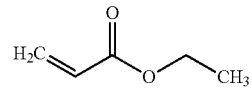

A.XXIVa

Ethylene glycol dimethyl acrylate having the following formula A.XXIVb.

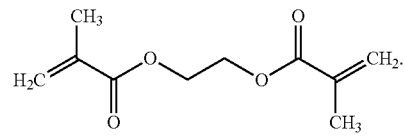

A.XXIVb

In one embodiment, the polymer of the present invention comprises fourth monomeric units derived from one or more $(C_1\text{-}C_{22})$alkyl (meth)acrylic esters, more typically $(C_1\text{-}C_{12})$ alkyl(meth)acrylic esters, such as ethyl acrylate, butyl methacrylate, or ethylhexyl acrylate.

Particular Monomeric Unit Combinations for HASE Polymer

In one embodiment, the polymer of the present invention comprises:
(a) one or more first monomeric units,
(b) one or more second monomeric units,
(c) one or more third monomeric units, and
(d) one or more fourth monomeric units,
each as described above.

In one embodiment of the polymer of the present invention:
(a) the first monomeric units each independently comprise at least one bicycloheptyl-polyether, bicycloheptenyl-polyether or branched $(C_5\text{-}C_{50})$alkyl-polyether group per monomeric unit, wherein the bicycloheptyl-polyether or bicycloheptenyl-polyether group may, optionally, be substituted on one or more ring carbon atoms by one or two $(C_1\text{-}C_6)$alkyl groups per carbon atom,
(b) the second monomeric units each independently comprise at least one pendant linear or branched $(C_5\text{-}C_{50})$alkyl-polyether group per monomeric unit, provided that the first and second monomeric units cannot both comprise a branched $(C_5\text{-}C_{50})$alkyl-polyether group,
(c) the third monomeric units each independently comprise at least one carboxylic acid, sulfonic acid, or phosphoric acid group per molecule, and
(d) the fourth monomeric units each independently comprise at least one alkyl, hydroxyalkyl, alkoxyalkyl, cycloalkyl, aryl, aralkyl, or aryloxy group per monomeric unit.

In one embodiment:
(a) the first monomeric units each independently comprise at least one bicycloheptyl-polyether or bicycloheptenyl-polyether group, which may, optionally, be substituted on one or more ring carbon atoms by one or two $(C_1\text{-}C_6)$alkyl groups per carbon atom, per monomeric unit,
(b) the second monomeric units, each independently comprise at least one pendant linear or branched $(C_5\text{-}C_{50})$alkyl-polyether group per monomeric unit,
(c) the third monomeric units each independently comprise at least one carboxylic acid, sulfonic acid, or phosphoric acid, more typically carboxylic acid, group per molecule, and (d) the fourth monomeric units each independently comprise at least one alkyl, more typically ($C_1$-$C_{22}$)alkyl, group per monomeric unit.

In one embodiment, the polymer of the present invention comprises, based on 100 monomeric units,
(a) from about 0.01, more typically from about 0.05, and more typically from about 0.10 of the first monomeric units, to about 10, more typically to about 5, and even more typically to about 2, of the first monomeric units,
(b) from about 0.01, more typically from about 0.05, and even more typically from about 0.10 of the second monomeric units, to about 10, more typically to about 5, and even more typically to about 2, of the second monomeric units, and
(c) from about 25, more typically from about 30, and even more typically from about 35 of the third monomeric units, to about 70, more typically to about 65, and even more typically to about 60, of the third monomeric units,
(d) from about 30, more typically from about 40, and even more typically from about 45 of the fourth monomeric units, to about 75, more typically to about 70, and even more typically to about 65 of the fourth monomeric units.

In one embodiment, the polymer of the present invention comprises, based on 100 pbw of the polymer,
(a) from about 0.1, more typically from about 0.5, and even more typically from about 1.0 pbw of the first monomeric units, to about 20, more typically to about 15, and even more typically to about 10, pbw of the first monomeric units,
(b) from about 0.1, more typically from about 0.5, and even more typically from about 1.0, pbw of the second monomeric units, to about 20, more typically to about 15, and even more typically to about 10, pbw of the second monomeric units, and
(c) from about 20, more typically from about 25, and even more typically from about 30, pbw of the third monomeric units, to about 60, more typically to about 55, and even more typically to about 60, pbw of the third monomeric units, and
(d) from about 25, more typically from about 35, and even more typically from about 40, pbw of the fourth monomeric units, to about 70, more typically to about 65, and even more typically to about 60, pbw of the fourth monomeric units.

In one embodiment, the polymer of the present invention comprises from about 0.4 to about 5, more typically from about 0.6 to about 4, and even more typically from about 0.8 to about 2 of the first monomeric units per each of the second monomeric units.

Particular Monomer Mixtures for HASE Polymer

In one embodiment, the polymer is the product of copolymerization of a mixture of monomers, comprising:
one or more first monomers,
one or more second monomers,
one or more third monomers, and
one or more fourth monomers,
each as described above.

In particular for this embodiment, the polymer is the product of copolymerization of a mixture of monomers, comprising:
(a) the one or more first monomers are each independently selected from monomers that comprise a reactive functional group and at least one bicycloheptyl-polyether, bicycloheptenyl-polyether, or branched ($C_5$-$C_{50}$)alkyl-polyether group per molecule, wherein the bicycloheptyl-polyether or bicycloheptenyl-polyether group may optionally be substituted on one or more ring carbon atoms by one or two ($C_1$-$C_6$)alkyl groups per carbon atom, (b) the one or more second monomers are each independently selected from monomers that comprise a reactive functional group and at least one pendant straight or branched ($C_5$-$C_{50}$)alkyl-polyether group per molecule and that are copolymerizable with the first monomer, provided that the first and second monomer cannot both comprise a branched ($C_5$-$C_{50}$)alkyl-polyether group,
(c) the one or more third monomers are each independently selected from monomers that comprise a reactive functional group and at least one carboxylic acid, sulfonic acid, or phosphoric acid group per molecule and that are copolymerizable with the first and second monomers, and
(d) the one or more fourth monomers are each independently selected from monomers that comprise a reactive functional group and at least one alkyl, hydroxyalkyl, alkoxyalkyl, cycloalkyl, aryl, aralkyl, or aryloxy group per monomeric unit and that are copolymerizable with the first, second and third monomers.

In one embodiment:
(a) the one or more first monomers are each independently selected from monomers that comprise a reactive functional group, more typically an ethylenically unsaturated group, and at least one bicycloheptyl-polyether or bicycloheptenyl-polyether group, which may optionally be substituted on one or more ring carbon atoms by one or two ($C_1$-$C_6$)alkyl groups per carbon atom per molecule, per molecule,
(b) the one or more second monomers are each independently selected from monomers that comprise a reactive functional group, more typically an ethylenically unsaturated group, and at least one pendant straight or branched ($C_5$-$C_{50}$)alkyl-polyether group per molecule and that are copolymerizable with the first monomer,
(c) the one or more third monomers are each independently selected from monomers that comprise a reactive functional group, more typically an ethylenically unsaturated group, and at least one carboxylic acid, sulfonic acid, or phosphoric acid, more typically, carboxylic acid, group per molecule and that are that are copolymerizable with the first and second monomers, and
(d) the one or more fourth monomers are each independently selected from monomers that comprise a reactive functional group, more typically an ethylenically unsaturated group, and at least one alkyl, more typically ($C_1$-$C_{22}$)alkyl, group per molecule unit and that are copolymerizable with the first, second and third monomers.

In one embodiment, the polymer of the present invention is the product of polymerization of a mixture of monomers comprising, based on the molar amount of the monomers:
(a) from about 0.01 mole %, more typically from about 0.05 mole %, and even more typically from about 0.10 mole % of the one or more first monomers, to about 10 mole %, more typically to about 5 mole %, and even more typically to about 2 mole % of the one or more first monomers,
(b) from about 0.01 mole %, more typically from about 0.05%, and even more typically from about 0.10 mole %, to about 10 mole %, more typically to about 5 mole %, and even more typically to about 2 mole %, of the one or more second monomers,
(c) from about 25 mole %, more typically from about 30 mole %, and even more typically from about 35 mole % of the third monomers to about 70 mole %, more typically to about 65 mole % and even more typically to about 60 mole % of the one or more third monomers, and
(d) from about 30, more typically from about 40, and even more typically from about 45, mol % of the fourth monomers, to about 75, more typically to about 70, and even more typically to about 65, mol % of the one or more fourth monomers.

In one embodiment, the polymer of the present invention is the product of polymerization of a mixture of monomers comprising, based on the 100 pbw of the total amount of the monomers:
(a) from about 0.1, more typically from about 0.5, and even more typically from about 1.0 pbw of the first monomers, to about 20, more typically to about 15, and even more typically to about 10, pbw of the one or more first monomers,
(b) from about 0.1, more typically from about 0.5, and even more typically from about 1.0, pbw of the second monomers, to about 20, more typically to about 15, and even more typically to about 10, pbw of the one or more second monomers, and
(c) from about 20, more typically from about 25, and even more typically from about 30, pbw of the third monomers, to about 60, more typically to about 55, and even more typically to about 50, pbw of the one or more third monomers, and
(d) from about 25, more typically from about 35, and even more typically from about 40, pbw of the third monomers, to about 70, more typically to about 65, and even more typically to about 60, pbw of the one or more fourth monomers.

In one embodiment, the polymer comprises the product of polymerization of a mixture of monomers comprising, based on the molar amount of monomers, from about 0.4 to about 5, more typically, from about 0.6 to about 4, and even more typically from about 0.8 to about 2 moles of the one or more first monomers per each mole of the one or more second monomers.

The polymer of the present invention can be conveniently prepared from the above-described monomers by known aqueous emulsion polymerization techniques using free-radical producing initiators, typically in an amount from 0.01 percent to 3 percent, based on the weight of the monomers.

In one embodiment, the polymerization is conducted at a pH of about 5.0 or less. Polymerization at an acid pH of about 5.0 or less permits direct preparation of an aqueous colloidal dispersion having relatively high solids content without the problem of excessive viscosity.

In one embodiment, the polymerization is conducted in the presence of one or more free-radical producing initiators selected from peroxygen compounds. Useful peroxygen compounds include inorganic persulfate compounds such as ammonium persulfate, potassium persulfate, sodium persulfate, peroxides such as hydrogen peroxide, organic hydroperoxides, for example, cumene hydroperoxide, and t-butyl hydroperoxide, organic peroxides, for example, benzoyl peroxide, acetyl peroxide, lauroyl peroxide, peracetic acid, and perbenzoic acid (sometimes activated by a water-soluble reducing agent such as ferrous compound or sodium bisulfite), and other free-radical producing materials or techniques such as 2,2'-azobisisobutyronitrile and high energy radiation sources.

In one embodiment, the polymerization is conducted in the presence of one or more emulsifiers. Useful emulsifiers include anionic surfactants, nonionic surfactants, amphoteric surfactants, and zwitterionic surfactants. In one embodiment, the emulsion polymerization is conducted in the presence of one or more anionic surfactants. Examples of anionic emulsifiers are the alkali metal alkyl aryl sulfonates, the alkali metal alkyl sulfates and the sulfonated alkyl esters. Specific examples of these well-known emulsifiers are sodium dodecyl benzene sulfonate, sodium dodecyl butylnaphthalene sulfonate, sodium lauryl sulfate, disodium dodecyl diphenyl ether disulfonate, disodium n-octadecyl sulfosuccinamate and sodium dioctyl sulfosuccinate. Known nonionic emulsifiers include, for example, fatty alcohols, alkoxylated fatty alcohols, and alkylpolyglucosides.

The emulsion polymerization may, optionally, be conducted in the presence, in an amount up to about 10 parts per 100 parts of polymerizable monomers, of one or more chain transfer agents. Representative chain transfer agents are carbon tetrachloride, bromoform, bromotrichloromethane, and long-chain alkyl mercaptans and thioesters, such as n-dodecyl mercaptan, t-dodecyl mercaptan, octyl mercaptan, tetradecyl mercaptan, hexadecyl mercaptan, butyl thioglycolate, isooctyl thioglycolate, and dodecyl thioglycolate.

Optionally, other ingredients well known in the emulsion polymerization art may be included, such as chelating agents, buffering agents, inorganic salts and pH adjusting agents.

In one embodiment, the polymerization is carried out at a temperature between about 60° C. and 90° C., but higher or lower temperatures may be used. The polymerization can be conducted batchwise, stepwise, or continuously with batch and/or continuous addition of the monomers, in a conventional manner.

The monomers can be copolymerized in such proportions, and the resulting emulsion polymers can be physically blended, to give products with the desired balance of properties for specific applications. For example, for analogous polymers of a given molecular weight, increasing the amount of first monomer tends to increase the yield strength exhibited by the polymer, increasing the relative amount of second monomer tends to increase the viscosity of the polymer. One or more fourth monomers may be added to adjust the properties of the polymer. For example, the addition of styrene as a fourth monomer tends to increase to a higher pH the adjustment required to dissolve the emulsion in an aqueous coating composition.

These polymeric products prepared by emulsion polymerization at an acid pH are in the form of stable aqueous colloidal dispersions containing the polymer dispersed as discrete particles having average particle diameters of about 400 to about 3000 Å and preferably about 600 to about 1750 Å, as measured by light scattering. Dispersions containing polymer particles smaller than about 400 Å are difficult to stabilize, while particles larger than about 3000 Å reduce the ease of dispersion in the aqueous products to be thickened.

In one embodiment, the polymer composition is in the form of an aqueous polymer dispersion, typically having a solids content including the polymer and any surfactants that may be present and based on the total weight of the polymer dispersion, of up to about 60 wt % and, more typically about 20 to about 50 wt %.

Alternatively, these polymers for use in the present invention can be made using known solution polymerization techniques, wherein the reactant monomers and initiator are dissolved in an appropriate solvent such as toluene, xylene, tetrahydrofuran, or mixtures thereof. Polymerization can be accomplished in the time and at the temperature necessary, e.g., 60° C. to 80° C. and about 2 to 24 hours. The polymer product can be isolated through normal separation techniques, including solvent stripping.

In one embodiment, these polymers for use in the present invention exhibit a weight average molecular weight, as determined by gel permeation chromatography and light scattering of a solution of the polymer in tetrahydrofuran and compared to a polystyrene standard, of greater than or equal to 30,000 grams per mole ("g/mole"). In one embodiment, the polymer of the present invention exhibits a weight average molecular weight of from 30,000 g/mole, more typically from about 100,000 g/mole, and even more typically from about 150,000 g/mole, to about 1,500,000 g/mole, more typically to about 1,000,000 g/mole, and even more typically to about 800,000 g/mole.

In one embodiment, these polymers for use in the present invention are in the form of an aqueous colloidal polymer dispersion. When the polymer composition is in the form of an aqueous colloidal polymer dispersion, the composition is maintained at a pH of about 5 or less to maintain stability. More typically, the aqueous colloidal polymer dispersion composition has a pH of about 2 to about 3. When thickening of the composition is desired, the pH of the composition can be increased to a value above about 5 by addition of a base to solubilize the polymer.

These HASE polymers and polymer compositions for use in the present invention are pH-responsive. At the lower pH levels at which the emulsion polymerization takes place, i.e., pH levels of 5 or less, the composition is relatively thin or non-viscous. When the pH of the polymer dispersion is neutralized or adjusted by addition of a base to a pH of about 5.5 or more, preferably about 6 to about 11, the composition thickens substantially. The composition turns from semi-opaque or opaque to translucent or transparent as viscosity increases. Viscosity increases as polymer dissolves partially or completely in the aqueous phase of the composition. Neutralization can occur in situ when the emulsion polymer is blended with the base and added to the aqueous phase. Or, if desired for a given application, neutralization can be carried out when blending with an aqueous product. Useful bases include, but are not limited to, ammonia, an amine, sodium hydroxide, potassium carbonate or the like.

For example, the HASE polymer having a polymer backbone of MAA and EA is pH-sensitive. Typically the copolymer is a latex at pH=2.3. When neutralized with a suitable base to a pH above about 5.5, the carboxyl groups on the methacrylic acid ionize to carboxylate ions. The charge on the polymer induces a conformational change, and the white latex becomes water-soluble, thus increasing the hydrodynamic volume of the polymer. When the HASE polymers swell, the pendant hydrophobic groups are free to build associations with one another and with other hydrophobes available in the formulation, such as surfactants, particulates, emulsion droplets and dyes. This phenomenon creates a network structure that results in a significant viscosity build.

Polymer Blends

In a second aspect, the present invention is directed to a blend of
(a) a first polymer comprising one or more first monomeric units, each independently comprising at least one bicycloheptyl-polyether, bicycloheptenyl-polyether or branched $(C_5\text{-}C_{50})$alkyl-polyether group per monomeric unit, wherein the bicycloheptyl-polyether or bicycloheptenyl-polyether group may optionally be substituted on one or more ring carbon atoms by one or two $(C_1\text{-}C_6)$alkyl groups per carbon atom, having a weight average molecular weight of greater than or equal to about 30,000 grams per mole, and
(b) a second polymer comprising one or more second monomeric units, each independently comprising at least one pendant linear or branched $(C_5\text{-}C_{50})$alkyl-polyether group per monomeric unit, provided that the first and second monomeric units cannot both comprise a branched $(C_5\text{-}C_{50})$alkyl-polyether group, having a weight average molecular weight of greater than or equal to about 30,000 grams per mole, wherein the first and second polymers each further comprise at least one polymerizable functional group per molecule of polymer, and
the first and second monomeric units cannot both comprise a branched $(C_5\text{-}C_{50})$alkyl-polyether group.

The first monomeric units and second monomeric units for the blend of polymers may be further defined as described above for the copolymer containing both the first monomeric units and second monomeric units. Furthermore, the first polymer may contain the above-described first monomeric units, third monomeric units and fourth monomeric units. The second polymer may contain the above-described second monomeric units, third monomeric units and fourth monomeric units.

For example, a blend could include:

A. a first polymer which comprises, based on 100 pbw of the polymer,
(a) from about 0.1, more typically from about 0.5, and even more typically from about 1.0 pbw of the first monomeric units, to about 20, more typically to about 15, and even more typically to about 10, pbw of the first monomeric units,
(c) from about 20, more typically from about 25, and even more typically from about 30, pbw of the third monomeric units, to about 60, more typically to about 55, and even more typically to about 60, pbw of the third monomeric units, and
(d) from about 25, more typically from about 35, and even more typically from about 40, pbw of the fourth monomeric units, to about 70, more typically to about 65, and even more typically to about 60, pbw of the fourth monomeric units; and B. a second polymer which comprises, based on 100 pbw of the polymer,
(a) from about 0.1, more typically from about 0.5, and even more typically from about 1.0 pbw of the first monomeric units, to about 20, more typically to about 15, and even more typically to about 10, pbw of the first monomeric units,
(b) from about 0.1, more typically from about 0.5, and even more typically from about 1.0, pbw of the second monomeric units, to about 20, more typically to about 15, and even more typically to about 10, pbw of the second monomeric units, and
(c) from about 20, more typically from about 25, and even more typically from about 30, pbw of the third monomeric units, to about 60, more typically to about 55, and even more typically to about 60, pbw of the third monomeric units, and
(d) from about 25, more typically from about 35, and even more typically from about 40, pbw of the fourth monomeric units, to about 70, more typically to about 65, and even more typically to about 60, pbw of the fourth monomeric units.

Liquid Carrier

In one embodiment, the composition of the present invention comprises the selected polymer and a liquid carrier.

In one embodiment, the liquid carrier is an aqueous carrier comprising water and the treatment solution is in the form of a solution, emulsion, or dispersion of the material and additives. In one embodiment, the liquid carrier comprises water and a water miscible organic liquid. Suitable water miscible organic liquids include saturated or unsaturated monohydric alcohols and polyhydric alcohols, such as, for example, methanol, ethanol, isopropanol, cetyl alcohol, benzyl alcohol, oleyl alcohol, 2-butoxyethanol, and ethylene glycol, as well as alkylether diols, such as, for example, ethylene glycol monoethyl ether, propylene glycol monoethyl ether and diethylene glycol monomethyl ether.

As used herein, terms "aqueous medium" and "aqueous media" are used herein to refer to any liquid medium of which water is a major component. Thus, the term includes water per se as well as aqueous solutions and dispersions.

Embodiments of Compositions and Uses

The present invention is suitable in the preparation of hydraulic fracturing fluids, enhanced oil recovery, personal care (cosmetics, toiletries, health and beauty aids, cosmeceuticals) and topical health care products, including without limitation, hair care products, such as shampoos (including combination shampoos, such as "two-in-one" conditioning shampoos), post-shampoo rinses, setting and style maintenance agents including setting aids, such as gels and sprays, grooming aids, such as pomades, conditioners, perms, relaxers, hair smoothing products, and the like, skin care products (facial, body, hands, scalp and feet), such as creams, lotions, conditioners, and cleansing products, anti-acne products, anti-aging products (exfoliant, keratolytic, anticellulite, antiwrinkle, and the like), skin protectants such as sunscreens, sunblock, barrier creams, oils, silicones, and the like, skin color products (whiteners, lighteners, sunless tanning accelerators, and the like), hair colorants (hair dyes, hair color rinses, highlighters, bleaches and the like), pigmented skin colorants (face and body makeups, foundation creams, mascara, rouge, lip products, and the like), bath and shower products (body cleansers, body wash, shower gel, liquid soap, soap bars, syndet bars, conditioning liquid bath oil, bubble bath, bath powders, and the like), nail care products (polishes, polish removers, strengtheners, lengtheners, hardeners, cuticle removers, softeners, and the like), and any aqueous acidic to basic composition to which an effective amount of the associative polymer can be incorporated for achieving a beneficial or desirable, physical or chemical, effect therein during storage and/or usage.

Personal Care Compositions

In one embodiment, the present invention is directed to a personal care composition comprising water, one or more surfactants, a polymer of the present invention, and one or more personal care benefit agents, wherein at least one personal care benefit agent comprises a water insoluble additive (for example, oil, mica, exfoliation beads, emollients, moisturizers).

In one embodiment, the personal care composition comprises, based on 100 parts by weight ("pbw") of the personal care composition, from about 10 to about 90 pbw, more typically from about 40 to about 85 pbw, water, from about 1 to about 50 pbw of one or more surfactants, and from about 0.05 to about 10 pbw, more typically from about 0.1 to about 5 pbw, of the polymer of the present invention.

The compositions of the invention are especially useful in areas requiring thickening at neutral pHs, such as in personal care compositions comprising at least one personal care benefit agent, wherein at least one of the personal care benefit agents comprises a water insoluble additive (for example, oil, mica, exfoliation beads, emollients, moisturizers).

In one embodiment, the aqueous composition comprising the polymer of the present invention exhibits viscoelastic properties at neutral to alkaline pH values, typically at pH values greater than or equal to about 5, more typically greater than or equal to about 5.5, even more typically of from about 6 to about 9.

In one embodiment, an aqueous composition comprising the polymer of the present invention exhibits non-Newtonian "shear thinning" viscosity, that is, a viscosity that, within a given range of shear stress, decreases with increasing shear stress.

In one embodiment, an aqueous composition comprising the polymer of the present invention (describe relevant conditions, e.g., concentration, pH, etc.) exhibits a "yield strength", that is, a minimum shear stress required to initiate flow of the composition, and exhibits shear thinning behavior over some range of shear stress above the yield strength, such as for example, a yield strength of greater than 0 Pa, more typically of from about 0.1 Pa and even more typically from about 1 Pa to about 10 Pa, and even more typically about 6 Pa, and even more typically about 2 Pa. In one embodiment, the polymer of the present invention is not cross-linked and provides a yield strength of greater than 0 Pa, in the absence of any cross-linking of the polymer.

The polymeric thickeners of this invention are advantageous for use with the water-based compositions according to the foregoing description and with compositions containing those materials. Mixtures or combinations of two or more thickeners may be used, if desired.

The polymer compositions of the present invention may be added to aqueous product systems at a wide range of amounts depending on the desired system properties and end use applications. The polymer may typically be added at any stage or at multiple stages of the preparation of an aqueous product composition, such as, by addition to water before addition of other ingredients, by addition to the composition among other added ingredients, or by addition after addition of any other ingredients, as the final ingredient in a series of additions and/or as a post-addition to the composition, such as, for example, as a post-addition to adjust the rheological properties of the composition.

In an embodiment the composition is for cleaning hair or skin and comprises:
the polymer,
at least one detersive surfactant, and
at least one member of the group consisting of oil, mica, exfoliation beads, emollients, moisturizers, pearlizing agent, a silicone hair conditioning agent, an antidandruff ingredient, a glycol emulsifier provided that a 10% aqueous solution of said composition has a pH from about 4 to about 12.

Surfactants

Suitable surfactants for including in personal care compositions of the present invention (as well as compositions for other uses of the present invention) include anionic surfactants, cationic surfactants, amphoteric surfactants, zwitterionic surfactants, nonionic surfactants, and mixtures thereof.

Anionic Surfactant

Suitable anionic surfactants include, for example, alkylbenzene sulfonates, alpha olefin sulfonates, paraffin sulfonates, alkyl ester sulfonates, alkyl sulfates, alkyl alkoxy sulfates, alkyl sulfonates, alkyl alkoxy carboxylates, alkyl alkoxylated sulfates, monoalkyl phosphates, and dialkyl phosphates, alkyl lactylates, isethionate taurate surfactants, sarcosinate surfactants and salts thereof, as well as mixtures of such compounds, wherein the cationic counterion of an anionic surfactant in salt form is typically selected from sodium, potassium, lithium, calcium, magnesium, ammonium, $(C_1-C_6)$alkyl ammonium cations.

Suitable anionic surfactants include, for example, one or more branched and/or linear organosulfate surfactants. In one embodiment, the anionic surfactant comprises one or more anionic organosulfate surfactants according to structure (1):

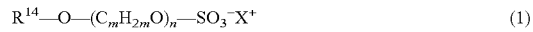

$$R^{14}-O-(C_mH_{2m}O)_n-SO_3^-X^+ \qquad (1)$$

wherein $R^{14}$ is $(C_8-C_{18})$alkyl or $(C_8-C_{18})$alkenyl, more typically $(C_{10}-C14)$alkyl, m is 2, 3, or 4, n is an integer of from 1 to about 7, more typically from 1 to 8, even more typically from 1 to 6, $X^+$ is a cation.

In one embodiment, $R^{14}$ is a branched $(C_8-C_{18})$alkyl group or a $(C_8-C_{18})$alkenyl group, more typically a branched $(C_{10}-C_{16})$alkyl group, such as tridecyl. Suitable branched alkyl groups include methyldecyl groups, methylundecyl groups, methyldodecyl groups, ethyldecyl groups, ethylundecyl groups, and ethyldodecyl groups, such as for example, 1-methyldecyl, 1-methylundecyl, 1-methyldodecyl, 1-ethyldecyl, 1-ethylundecyl, and 1-ethyldodecyl.

In one embodiment, m is 2 or 3, more typically 2.

In one embodiment, n is 1, 2, 3, or 4. As used herein, modifying an alkyl or alkenyl group with the suffix "eth" generally indicates the addition of one or more ethylene oxide units, for example, trideceth refers to an ethoxylated tridecyl group, and the suffix "-n", wherein n is an integer, indicates the number of such ethylene oxide units per group, for example "trideceth-3" indicates an ethoxylated tridecyl group with 3 ethylene oxide units per tridecyl group.

Typical branched anionic surfactants include, for example, sodium trideceth sulfate, sodium tridecyl sulfate, ammonium trideceth sulfate, and ammonium tridecyl sulfate, magnesium trideceth sulfates, monoethanolamine trideceth sulfate, diethanolamine trideceth sulfates, and triethanolamine trideceth sulfate.

In one embodiment, the anionic organosulfate surfactant comprises one or more branched alkylether sulfate selected from sodium trideceth-1 sulfate, potassium trideceth-1 sulfate, and ammonium trideceth-1 sulfate, sodium trideceth-2 sulfate, potassium trideceth-2 sulfate, and ammonium trideceth-2 sulfate, sodium trideceth-3 sulfate, potassium trideceth-3 sulfate, and ammonium trideceth-3 sulfate, sodium trideceth-4 sulfate, potassium trideceth-4 sulfate, and ammonium trideceth-4 sulfate.

Typical linear anionic surfactants include, for example, one or more linear C10-C22 alkyl, ammonium or alkali metal ether sulfates, for example, ammonium lauryl sulfate, ammonium laureth sulfate, triethanolamine laureth sulfate, monoethanolamine lauryl sulfate, monoethanolamine laureth sulfate, diethanolamine lauryl sulfate, diethanolamine laureth sulfate, magnesium laureth sulfate, lauric monoglyceride sodium sulfate, sodium lauryl sulfate, sodium laureth sulfate, potassium lauryl sulfate, and potassium laureth sulfate.

In one embodiment, the anionic surfactant comprises disodium laureth sulfosuccinate, sodium monoalkyl phosphate, sodium dialkyl phosphate, ammonium cocoyl sulfate, sodium cocoyl sulfate, potassium cocoyl sulfate, monoethanolamine cocoyl sulfate, sodium trideceyl benzene sulfonate, and sodium dodecyl benzene sulfonate, sodium oleth sulfate, potassium oleth sulfate, magnesium oleth sulfate, ammonium oleth sulfate, monoethanolamine oleth sulfate, diethanolamine oleth sulfate, triethanolamine oleth sulfate, or a mixture thereof.

In one embodiment, the anionic surfactant comprises one or more anionic surfactant selected from isethionate surfactant compounds, taurate surfactant compounds, and sarcosinate surfactant compounds, according to structure (2):

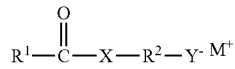
(2)

wherein:

$R^1$ is alkyl, alkenyl, aryl, or aralkyl, $R^2$ is alkylene, which may optionally be substituted on one or more of such methylene units with alkyl, alkoxyl, alkenyl, aryl, aralkyl, alkaryl, or heterocyclyl, and which may optionally be interrupted at one or more positions by an oxygen atom, X is O or $NR^3$, $NR^3$ is H or alkyl, $Y^-$ is $SO_3^-$ or $CO_2^-$, and $M^+$ is a cation.

In one embodiment, $R^2$ is methylene, or dimethylene.

In one embodiment, $R^2$ is alkyleneoxyalkylene or alkylene poly(oxyalkylene) comprising from 2 to about 50 oxyalkylene units, more typically methylenepoly(oxyethylene), dimethylenepoly(oxyethylene), methylenepoly(oxypropylene), or dimethylenepoly(oxypropylene).

In one embodiment, $M^+$ is sodium, potassium, lithium, calcium, magnesium, ammonium cation, or an ammonium cation, such as, for example, an isopropylammonium, monoethanolammonium, diethanolammonium, or triethanolammonium cation. More typically, M+ is a sodium cation.

Suitable isethionate surfactants are esters of isethionic acid and salts thereof. In one embodiment, the second anionic surfactant comprises one or more isethionate surfactant compounds according to structure (3):

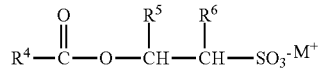
(3)

wherein:

$R^4$ is alkyl, alkenyl, aryl, or aralkyl, typically $(C_8-C_{22})$ alkyl, $R^5$ and $R^6$ are each independently H or C1-4 alkyl, and $M^+$ is a cation, e.g., sodium, potassium, or ammonium cation.

Suitable isethionate surfactant compounds according to structure (2) include, for example, sodium lauroyl isethionate, sodium lauroyl isethionate, sodium myristoyl isethionate, sodium cocoyl isethionate, sodium oleoyl isethionate, and ammonium oleoyl isethionate.

Suitable taurate surfactants are amides of methyl taurine and salts thereof. In one embodiment, the second anionic surfactant comprises one or more taurate surfactant compounds according to structure (4):

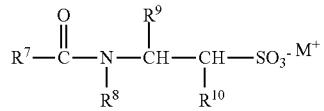
(4)

wherein:

$R^7$ is alkyl, alkenyl, aryl, or aralkyl $R^8$ is H or C1-4 alkyl, $R^9$ and $R^{19}$ are each independently H or C1-4 alkyl, and M+ is a cation, e.g., sodium, potassium, or ammonium cation.

Suitable taurate surfactant compounds according to structure (3) include, for example, sodium methyl lauroyl taurate, sodium methyl myristoyl taurate, potassium methyl myristoyl taurate, sodium methyl cocoyl taurate, sodium methyl oleoyl taurate, calcium methyl lauroyl taurate, potassium methyl lauroyl taurate, and ammonium methyl lauroyl taurate.

Suitable sarcosinate surfactants are amides of sarcosine and salts thereof. In one embodiment, the first anionic surfactant comprises one or more sarcosinate surfactant compounds according to structure (5):

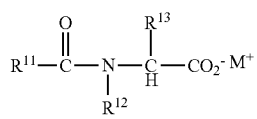

(5)

wherein:

wherein $R^{11}$ is $(C_8-C_{22})$alkyl, $R^{12}$ and $R^{13}$ are each independently H or $(C_1-C_4)$alkyl, more typically H or methyl, and M+ is a sodium, potassium or ammonium cation.

Suitable sarcosinate surfactant compounds according to structure (4) include, for example, sodium lauroyl sarcosinate, sodium myristoyl sarcosinate, potassium myristoyl sarcosinate, sodium cocoyl sarcosinate, sodium oleoyl sarcosinate, triethanolamine lauroyl sarcosinate, and ammonium oleoyl sarcosinate.

The cationic counterion of any anionic surfactant in salt form is typically a sodium cation but may alternatively be a potassium, lithium, calcium, magnesium, ammonium cation, or an alkyl ammonium anion having up to 6 aliphatic carbon atoms, such as anisopropylammonium, monoethanolammonium, diethanolammonium, or triethanolammonium cation. Ammonium and ethanolammonium salts are generally more soluble than the sodium salts. Mixtures of the above cations are suitable as well.

Cationic Surfactant

Cationic surfactants are generally known and include for example, mono-cationic surfactants according to formula (B.XXV):

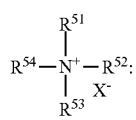

(B.XXV)

wherein:

$R^{51}$, $R^{52}$, $R^{53}$, and $R^{54}$ are each independently H or an organic group, provided that at least one of $R^{51}$, $R^{52}$, $R^{53}$, and $R^{54}$ is not hydrogen, and X⁻ is an anion, typically a chloride, bromide, methosulfate, ethosulfate, lactate, saccharinate, acetate or phosphate anion.

If one to three of $R^{51}$, $R^{52}$, $R^{53}$, and $R^{54}$ of the compound of structure XXV are each H, then the compound according to structure XXV is an amine salt. Suitable amine slat type cationic surfactants include polyethoxylated (2) oleyl/stearyl amine, ethoxylated tallow amine, cocoalkylamine, oleylamine, and tallow alkyl amine.

If $R^{51}$, $R^{52}$, $R^{53}$, and $R^{54}$ of the compound of structure B.XXV are each independently an organic group, then the compound of structure B.XXV is a quaternary ammonium compound. In one embodiment, $R^{51}$, $R^{52}$, $R^{53}$, and $R^{54}$ are each independent $(C_8-C_{24})$ branched or linear hydrocarbon groups which may comprise additional functionality such as, for example, fatty acids or derivatives thereof, including esters of fatty acids and fatty acids with alkoxylated groups, alkyl amido groups, aromatic rings, heterocyclic rings, phosphate groups, epoxy groups, and hydroxyl groups. The nitrogen atom may also be part of a heterocyclic or aromatic ring system, e.g., cataphyll morpholinium ethosulfate or steapyrium chloride.

Examples of suitable quaternary ammonium compounds of the monoalkyl amine derivative type include: cetyl trimethyl ammonium bromide (also known as CETAB or cetrimonium bromide), cetyl trimethyl ammonium chloride (also known as cetrimonium chloride), myristyl trimethyl ammonium bromide (also known as myrtrimonium bromide or Quaternium-13), stearyl dimethyl benzyl ammonium chloride (also known as stearalkonium chloride), oleyl dimethyl benzyl ammonium chloride, (also known as olealkonium chloride), lauryl/myristryl trimethyl ammonium methosulfate (also known as cocotrimonium methosulfate), cetyl dimethyl (2)hydroxyethyl ammonium dihydrogen phosphate (also known as hydroxyethyl cetyldimonium phosphate), cocotrimonium chloride, distearyldimonium chloride, wheat germ-amidopropalkonium chloride, stearyl octyldimonium methosulfate, isostearaminopropalkonium chloride, dihydroxypropyl PEG-5 linoleaminium chloride, PEG-2 stearmonium chloride, Quaternium 18, Quaternium 80, Quaternium 82, Quaternium 84, behentrimonium chloride, dicetyl dimonium chloride, behentrimonium methosulfate, tallow trimonium chloride and behenamidopropyl ethyl dimonium ethosulfate. Mixtures may also be used in the present invention.

Quaternary ammonium compounds of the dialkyl amine derivative type include, for example, distearyldimonium chloride, dicetyl dimonium chloride, stearyl octyldimonium methosulfate, dihydrogenated palmoylethyl hydroxyethylmonium methosulfate, dipalmitoylethyl hydroxyethylmonium methosulfate, dioleoylethyl hydroxyethylmonium methosulfate, hydroxypropyl bisstearyldimonium chloride, and mixtures thereof.

Quaternary ammonium compounds of the imidazoline derivative type include, for example, isostearyl benzylimidonium chloride, cocoyl benzyl hydroxyethyl imidazolinium chloride, cocoyl hydroxyethylimidazolinium PG-chloride phosphate, Quaternium 32, and stearyl hydroxyethylimidonium chloride, and mixtures thereof.

Typical cationic surfactants comprise dialkyl derivatives such as dicetyl dimonium chloride and distearyldimonium chloride, branched and/or unsaturated cationic surfactants such as isostearylaminopropalkonium chloride or olealkonium chloride, long chain cationic surfactants such as stearalkonium chloride and behentrimonium chloride, as well as mixtures thereof.

Suitable anionic counterions for the cationic surfactant include, for example, chloride, bromide, methosulfate, ethosulfate, lactate, saccharinate, acetate and phosphate anions.

Amphoteric Surfactant

Amphoteric surfactants are generally known. Suitable amphoteric surfactants include the alkali metal, alkaline earth metal, ammonium or substituted ammonium salts of alkyl amphodipropionates, alkyl amphodiacetates, alkyl amphoglycinates, and alkyl amphopropionates, alkyl amphocarboxy glycinates and alkyl amphocarboxypropionates, as well as alkyl iminopropionates, alkyl iminodipropionates, and alkyl amphopropylsulfonates. Typical amphoteric surfactants are fatty acid amides.

Examples of such amphoteric surfactants include cocoamphoacetate, cocoamphopropionate, cocoamphodiacetate, lauroamphoacetate, lauroamphodiacetate, lauroamphodipropionate, lauroamphodiacetate, cocoamphopropylsulfonate, caproamphodiacetate, caproamphoacetate, caproamphodipropionate, and stearoamphoacetate. Specific examples of suitable amphoteric surfactant include sodium lauroamphoacetate, sodium lauroamphopropionate, disodium lauroamphodiacetate, sodium cocoamphoacetate, disodium cocoamphodiacetate, or a mixture thereof.

Typical suitable amphoteric surfactants include the alkali metal, alkaline earth metal, ammonium or substituted ammonium salts of alkyl amphodipropionates, alkyl amphodiacetates, alkyl amphoglycinates and alkyl amphopropionates, alkyl amphocarboxy glycinates and alkyl amphocarboxypropionates, wherein alkyl represents an alkyl group having 6 to 20 carbon atoms. Other typical amphoteric surfactants include alkyl iminopropionates, alkyl iminodipropionates and alkyl amphopropylsulfonates having between 12 and 18 carbon atoms; alkyl betaines and amidopropyl betaines and alkyl sultaines and alkylamidopropylhydroxy sultaines wherein alkyl represents an alkyl group having 6 to 20 carbon atoms.

The term "amphoteric surfactant" as utilized herein encompasses one or more amphoteric surfactants such as mixtures of amphoteric surfactants Particularly useful amphoteric surfactants include both mono and dicarboxylates such as those of the formulae B.I and B.II:

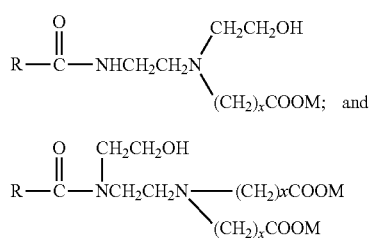

wherein R is an alkyl group of 6-20 carbon atoms, x is 1 or 2 and M is hydrogen or sodium. Mixtures of the above structures are particularly preferred.

A preferred amphoteric surfactant for use is cocoamphoacetate. It can be present from 0% to 10% based on the total weight of the concentrate. Preferably, cocoamphoacetate will comprise from about 1% to about 7% and most preferably from about 2% to about 4% of the concentrate.

In one embodiment, the amphoteric/zwitterionic surfactant comprises derivatives of aliphatic secondary and tertiary amines in which the aliphatic radical is straight chain or branched and wherein one of the aliphatic substituents contains from about 8 to about 18 carbon atoms and one contains an anionic water-solubilizing group, as well as mixtures thereof.

In one embodiment, the aqueous surfactant and/or personal care composition of the present invention are each substantially free of amphoteric surfactants.

Zwitterionic Surfactant

Zwitterionic surfactants are generally known and include betaine surfactants and sultaine surfactants, such as for example decyl dimethyl betaine, undecyl dimethyl betaine, dodecyl dimethyl betaine, tridecyl dimethyl betaine, tetradecyl dimethyl betaine, coco dimethyl betaine, hexadecyl dimethyl betaine, heptadecyl dimethyl betaine, octadecyl dimethyl betaine, dodecylamidopropyl dimethyl betaine, cocoamidopropyl dimethyl betaine, oleylamidopropyl betaine, lauryl dihydroxypropyl glycinate, lauryl di(hydroxypoly(ethoxy)) glycinate, lauryl bis-(2-hydroxy-ethyl)carboxy methyl betaine, stearyl bis-(2-hydroxy-propyl)carboxymethyl betaine, cocodimethyl sulfopropyl betaine, stearyldimethyl sulfopropyl betaine, lauryl dimethyl sulfoethyl betaine, lauryl bis-(2-hydroxy-ethyl)sulfopropyl betaine, and mixtures thereof.

Suitable betaine surfactants also include cocodimethyl carboxymethyl betaine, lauryl dimethyl carboxymethyl betaine, lauryl dimethyl alpha-carboxy-ethyl betaine, cetyl dimethyl carboxymethyl betaine, oleyl dimethyl gamma-carboxypropyl betaine, and lauryl bis-(2-hydroxy-propyl)alpha-carboxyethyl betaine, amidopropyl betaines.

Suitable zwitterionic alkyl sultaine surfactants include alkylamidopropylhydroxy sultaines and fatty amine surfactants.

In one embodiment, the aqueous surfactant and/or personal care composition of the present invention are each substantially free of zwitterionic surfactants.

Non-Ionic Surfactant

Nonionic surfactants are generally known and include, for example, alkanolamides, which may optionally be alkoxylated, amine oxides, fatty alcohols, which may optionally be alkoxylated, alkoxylated alkyl phenols, fatty acids, fatty acid esters, and alkylglucosides, such as cocamide DEA, cocamide MIPA, PEG-5 cocamide MEA, lauramide DEA, lauramine oxide, cocamine oxide, stearamine oxide, stearamidopropylamine oxide, palmitamidopropylamine oxide, decylamine oxide, stearyl alcohol, sorbitan monolaurate, polysorbates, ethoxylated lauryl alcohols, polyethylene glycol distearates, dodecylglucoside, octadecylpolyglucosides, and mixtures thereof.

Examples of useful nonionic surfactants can additionally include condensates of ethylene oxide with a hydrophobic moiety which has an average hydrophilic lipophilic balance (HLB) between about 8 to about 16, and more preferably, between about 10 and about 12.5. These surfactants include the condensation products of primary or secondary aliphatic alcohols having from about 8 to about 24 carbon atoms, in either straight or branched chain configuration, with from about 2 to about 40, and preferably between about 2 and about 9 moles of ethylene oxide per mole of alcohol.

In a preferred embodiment the aliphatic alcohol comprises between about 9 and about 18 carbon atoms and is ethoxylated with between about 3 and about 12 moles of ethylene oxide per mole of aliphatic alcohol. Especially preferred are the about 12 to about 15 carbon primary alcohol ethoxylates containing about 5 to about 9 moles of ethylene oxide per mole of alcohol. One such material is commercially sold under the trade name NEODOL 25-9 by Shell Chemical Company. Other commercial nonionic surfactants include NEODOL 25-6.5 and NEODOL 25-7 sold by Shell Chemical Company.

Other suitable nonionic surfactants include the condensation products of about 6 to about 12 carbon atom alkyl phenols with about 3 to about 30, and preferably between about 5 and 14 moles of ethylene oxide. Examples of such surfactants are sold under the trade names IGEPAL CO 530, IGEPAL CO 630, IGEPAL C0720 and IGEPAL CO 730 by Rhodia, Inc. Still other suitable nonionic surfactants are described in U.S. Pat. No. 3,976,586. To the extent necessary, this patent is expressly incorporated by reference.

Most preferred for use are mixed linear alcohol ethoxylates such as Laureth-7 sold as RHODASURF L-790 by Rhodia, Inc.

In one embodiment, the nonionic surfactant comprises one or more of alkanolamides, amine oxides, fatty alcohols, alkoxylated fatty alcohols, fatty acids, and fatty acid esters.

Suitable alkanolamides include aliphatic acid alkanolamides, such as cocamide DEA, cocamide MIPA, cocamide MEA, PEG-5 cocamide MEA, lauramide DEA, and lauramide MEA, as well as alkoxylated alkanolamides, and mixtures thereof. MIPA is monoisopropanolamide; PEG is polyethylene glycol; MEA is monoethanol amine; and DEA is diethanol amine.

Suitable amine oxides comprise, saturated or unsaturated branched or straight chain ($C_{10}$-$C_{24}$) alkyl dimethyl oxides or ($C_{10}$-$C_{24}$) alkyl amidopropyl amine oxides, such as for example, lauramine oxide, cocamine oxide, stearamine oxide, stearamidopropylamine oxide, palmitamidopropylamine oxide, decylamine oxide as well as mixtures thereof.

Suitable fatty alcohols include, for example, saturated or unsaturated branched or straight chain ($C_{10}$-$C_{24}$) alcohols, more typically saturated or unsaturated branched or straight chain ($C_{10}$-$C_{24}$) alcohols, such as for example, decyl alcohol, lauryl alcohol, myristyl alcohol, cetyl alcohol, stearyl alcohol, oleyl alcohol, linoleyl alcohol, linolenyl alcohol and tridecyl alcohol, and mixtures thereof.

Suitable alkoxylated fatty alcohols include alkoxylated, typically ethoxylated, derivatives of saturated or unsaturated branched or straight chain ($C_{10}$-$C_{24}$) alcohols, more typically saturated or unsaturated branched or straight chain ($C_{10}$-$C_{24}$) alcohols, which may include, on average, from 1 to 22 alkoxyl units per molecule of alkoxylated alcohol, such as, for example, ethoxylated lauryl alcohol having an average of 5 ethylene oxide units per molecule. Mixtures of these alkoylated alcohols may be used.

Suitable fatty acids include saturated or unsaturated ($C_{10}$-$C_{24}$) carboxylic acids, more typically saturated or unsaturated ($C_{10}$-$C_{24}$) carboxylic acids, such as, for example, lauric acid, oleic acid, stearic acid, myristic acid, cetearic acid, isostearic acid, linoleic acid, linolenic acid, ricinoleic acid, elaidic acid, arichidonic acid, myristoleic acid, and palmitoleic acid, as well as neutralized versions thereof.

Suitable fatty acid esters include esters of saturated or unsaturated ($C_{10}$-$C_{24}$) carboxylic acids, more typically saturated or unsaturated ($C_{10}$-$C_{24}$) carboxylic acids, for example, propylene glycol isostearate, propylene glycol oleate, glyceryl isostearate, and glyceryl oleate, and mixtures thereof.

In one embodiment, the aqueous surfactant and/or personal care composition of the present invention are each substantially free of alkanolamides, amine oxides, fatty alcohols, alkoxylated fatty alcohols, fatty acids, and/or fatty acid esters.

In one embodiment, the non-ionic surfactant is selected from non-ionic surfactants other than alkanolamides, amine oxides, fatty alcohols, alkoxylated fatty alcohols, fatty acids, and fatty acid esters. Suitable non-ionic surfactants other than alkanolamides, amine oxides, fatty alcohols, alkoxylated fatty alcohols, fatty acids, and fatty acid esters include, for example, compounds produced by the condensation of alkylene oxide groups with an organic hydrophobic compound, which may be aliphatic, or alkyl aromatic in nature. Typical nonionic surfactants consist of polyethylene, polypropylene, and polybutylene oxide condensates of alkyl phenols, and alkylpolyglycosides, and mixtures thereof.

Structured Surfactant Compositions

Compositions of the present invention for personal care or other uses may include structured surfactants. Surfactants in the structured surfactant compositions exist in the form of lamellar phases that are planar and/or in the form of multi-lamellar vesicles (MLVs). Commonly, the surfactant phase is present as MLVs, i.e., lamellar droplets, dispersed in the aqueous phase. MLVs consist of an onion-like configuration of concentric bi-layers of surfactant molecules, between which is trapped water or electrolyte solution. Exclusively planar lamellar surfactant phases or exclusively MLV (multi-lamellar vesicle) surfactant phases or the combination of both forms can co-exist in the same composition. Structured surfactant compositions are typically pumpable, non-Newtonian compositions that have the capacity physically to suspend water insoluble particles by virtue of the presence of these lamellar surfactant phases.

One embodiment of a structured surfactant comprises a branched anionic surfactant, a non-ionic surfactant, and an amphoteric surfactant, for example sodium trideceth sulfate, cocamide MEA and sodium lauroamphoacetate, respectively, and typically an electrolyte.

Sodium trideceth sulfate is a branched anionic surfactant shown in Formula B.XXV. There is a branching present in the carbon chain. Since it is not always at the same position, it is not shown.

$$CH_3(CH_2)_{12}(OCH_2CH_2)_nOSO_3Na \qquad \text{B.XXV.}$$

Cocamide MEA is a non-ionic surfactant and shown in Formula B.XXVI.

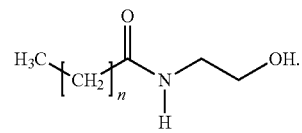

B.XXVI

Sodium Lauroamphoacetate is an amphoteric surfactant and shown in Formula B.XXVII.

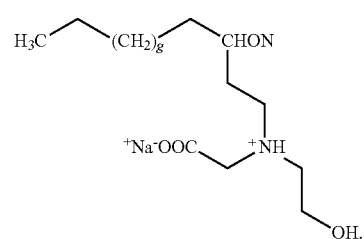

B.XXVII

Another embodiment of a structured surfactant comprises a non-branched anionic surfactant, a non-ionic surfactant, and an amphoteric surfactant, for example sodium lauryl sulfate, cocamide MIPA and sodium lauroamphoacetate, respectively, and typically an electrolyte. A typical advantage of the present invention is that it permits reducing the amount of branched anionic surfactant and/or replacing the branched anionic surfactant with linear anionic surfactant (non-branched anionic surfactant).

Sodium lauryl sulfate (SLS) is an anionic surfactant shown in Formula B.XXVIII.

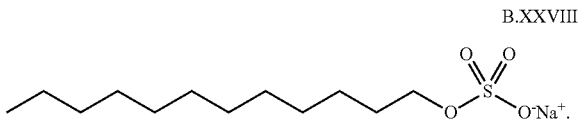

B.XXVIII

Cocamide MIPA is a non-ionic surfactant and is shown in Formula B.XXIV.

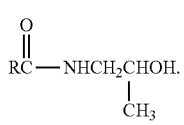

B.XXIV

Sodium lauroamphoacetate is shown above.

The following process is used to obtain long lasting metastable multilamellar vesicles (MLVs) consisting of concentric shells of lamellar surfactant bilayers. The MLVs (i.e. SSL formulations) are obtained through a simple process:

The blend is diluted in water to the desired active concentration;
The electrolyte level is adjusted by adding between 0.5% to 5% w/w NaCl;
The pH is adjusted to 5-5.5 with the addition of a 50% Citric Acid solution;
The resulting mixture is sheared (e.g. mixed at 150 RPM).

In general, the structured surfactant composition is made by combining and mixing the components in water, and optionally adjusting the pH and/or adding a preservative to the mixture.

FIG. 2 shows a schematic of a process for forming a structured surfactant. In the process a lamellar phase or micellar phase 10 is subjected to shear in a structuring process to form multilamellar vesicles (structured surfactant) liquid 20.

Some embodiments of the composition of the present invention comprises, alone, or, more typically, interspersed with an aqueous phase, an ordered surfactant phase, typically a lamellar surfactant phase, more typically a MLV (multi-lamellar vesicle) surfactant phase. Due to the presence of the lamellar surfactant phase, the composition of the present invention exhibits, on visual inspection, an opaque appearance. The composition of the present invention exhibits an opaque appearance in the absence, as well as in the presence, of water insoluble components, such as oils. In one embodiment, the structured surfactant compound of the present invention ranges from a turbid appearance to a uniform, saturated white appearance.

Due to the presence of the lamellar surfactant phase, the composition of the present invention exhibits a yield strength of greater than 0 Pascals at room temperature. As used herein, "yield strength" refers to the magnitude of the applied force required to induce the composition to flow. In one embodiment, the composition exhibits a yield strength of greater than 0.1 Pascals ("Pa"), more typically from about 1 to about 100 Pa, and even more typically from about 1 to about 10 Pa, as determined by measurements using a controlled stress/strain rheometer at two or more shear rates. The presence or absence of a non-zero yield strength may also be reliably determined on a qualitative basis by visual observation of the flow characteristics of the composition and the resistance of the composition to deformation caused by, for example, movement of a hand-held spatula a sample of the composition.

In one embodiment, the composition of the present invention is capable of suspending water insoluble or partially water-soluble components. As used herein, characterization of an aqueous composition as "capable of suspending", or as being "able of suspend" water insoluble or partially water-soluble components means that the composition substantially resists flotation of such components in the composition or sinking of such components in such composition so such components appear to be neutrally buoyant in such composition and remain at least substantially suspended in such composition under the anticipated processing, storage, and use conditions for such aqueous composition. The ability to suspend water insoluble or partially water-soluble components is one manifestation of the non-zero yield strength of the present invention, that is, the resistance of the structured surfactant composition of the present invention to deformation at low stresses is sufficient to balance the gravitational forces acting on water insoluble or partially water-soluble components, so that the components remain suspended in the structured surfactant composition.

In one embodiment, the presence of the ordered surfactant phase in the composition of the present invention is demonstrated by showing the combined water, surfactant, and electrolyte components of the composition, in the absence of water soluble components, exhibit an opaque visual appearance and exhibit a yield strength of greater than 0 Pascals.

As discussed above, the ordered phase, alone or more usually interspersed with an aqueous phase, provides a rheology sufficient, when the system is at rest, to immobilize any suspended particles but, upon application of a shearing force, is sufficiently low to allow the system to be pumped like a normal liquid. Such systems may display very low apparent viscosities when stirred, pumped or poured and yet be capable of maintaining particles, sometimes of millimeter or larger size, in suspension.

In one embodiment, the aqueous structured surfactant composition of the present invention exhibits shear-thinning viscosity. As used herein in reference to viscosity, the terminology "shear-thinning" means such viscosity decreases with an increase in shear rate. Shear-thinning may be characterized as a "non-Newtonian" behavior, in that it differs from that of a classical Newtonian fluid, for example, water, in which viscosity is not dependent on shear rate.

The structured surfactant composition can also be subjected to high shear mixing. As used herein, the term "high shear mixing" refers to mixing under high shear conditions, typically at a shear rate of greater than or equal to about 1,000 $sec^{-1}$, more typically greater than or equal to about 3,500 $sec^{-1}$. The structured surfactant composition may be subjected to a high shear mixing in known mixing equipment, such as, for example, a high shear mixer.

Viscosity is measured by known viscometric methods, such as for example, using a rotational viscometer, such as a Brookfield™ rotational viscometer, equipped with an appropriate spindle, at a rotation speed of from about 0.1 revolutions per minute ("rpm") to about 60 rpm.

In one embodiment, the aqueous structured surfactant and/or personal care composition of the present invention each have less than a 40% loss (more likely less than 30% and most likely less than 20% loss) in initial viscosity after 3 freeze thaw cycles. For example, a typical initial viscosity is 1000 or 5000 centipoise or more as measured by a Brookfield viscometer with an RV4 spindle at 50 or 100 RPM. Each freeze thaw cycle comprises maintaining the sample for 12 hours at 25° C. and then 12 hours at −10° C. The addition of the polymer ensures the viscosity drops by less than 40%, more likely less than 30%, most likely less than 20%. The initial viscosity and the freeze thaw viscosity as measured by a Brookfield viscometer with an RV4 spindle at 50 or 100 RPM.

The composition of the present invention is capable of suspending water-insoluble particles or partially water-soluble components, such as vegetable oils, hydrocarbon oils, silicone oils, solid particles, abrasives, and similar articles. The composition provides a means to include otherwise difficult to incorporate components in surfactant mixtures resulting in cosmetic preparations with multi-functional benefits including, in some cases, cleansing, moisturizing, improved skin feel, exfoliation/abrasion, novel appearance, or a combination of these benefits.

The ability of a composition to suspend water insoluble or partially water-soluble components is typically evaluated by mixing the composition with sufficient vigor to entrap air bubbles in the composition and then visually observing whether the air bubbles remain entrapped in the composition for a defined period of time, such as for example, 12 to 24 hours, under defined environmental conditions, such as for example, room temperature. In one embodiment, the composition of the present invention is capable of suspending air bubbles for at least 1 week, and more typically for at least 3 months. A composition capable of suspending air bubbles for at least 12 hours at room temperature is deemed to be generally capable of suspending water insoluble or partially water-soluble components in the composition under generally anticipated processing, storage, and use conditions for such composition. For components other than air, the result of the air suspension test should be confirmed by conducting an analogous suspension test using the component of interest. More rigorous testing may be appropriate for unusually rigorous processing, storage and/or use conditions.

In one embodiment, the ability to suspend water insoluble or partially water-soluble components is evaluated under more rigorous conditions. In particular, the mixed samples are visually evaluated after subjecting the samples to one or more freeze/thaw cycles, wherein each freeze/thaw cycle consists of 12 hours at −10° C. and 12 hours at 25° C. In one embodiment, composition of the present invention including the polymer remains capable of suspending air bubbles after one freeze/thaw cycle, more typically after 3 freeze/thaw cycles.

In one embodiment, the aqueous structured surfactant and/or personal care compositions of the present invention each comprise, based on 100 parts by weight of the composition:
(a) 0.5 to 40 parts by weight of total composition of at least one anionic surfactant,
(b) at least one surfactant selected from the group consisting of amphoteric surfactants, zwitterionic surfactants, non-ionic surfactants, and cationic surfactants,
wherein the total amount of surfactants (a) and (b) is from about 10 to about 40 parts by weight, and
(c) from greater than 0 to about 30 parts by weight of electrolyte in an amount effective, in combination with components (a) and (b), to provide a structured surfactant composition that comprises a surfactant phase having an ordered structure, and
(d) up to about 3 parts by weight of a freeze thaw agent selected from the aforementioned polymers and mixtures thereof.

In one embodiment, the total amount of surfactants, for the aqueous structured surfactant and/or personal care compositions of the present invention, consists essentially of the anionic surfactant, and the one or more surfactants selected from amphoteric surfactants, zwitterionic surfactants, and mixtures thereof.

In one embodiment, the total amount of surfactants, for the aqueous structured surfactant and/or personal care compositions of the present invention, consists of the anionic surfactant and the one or more surfactants selected from amphoteric surfactants, zwitterionic surfactants, and mixtures thereof.

In another embodiment, the aqueous structured surfactant and/or personal care compositions of the present invention each comprise, based on 100 pbw of the composition:
from greater than 0.5 to 40 parts by weight of the at least one anionic surfactant, and
(b) from greater than 0 to about 25 parts, typically 1 to 25 parts, by weight of surfactant selected from the group consisting of amphoteric surfactants, zwitterionic surfactants, non-ionic surfactants, and cationic surfactants, and
(c) from greater than 0 to about 30 parts, typically 1 to 30 parts, by weight of electrolyte, in an amount effective to, in combination with components (a) and (b), provide a structured surfactant composition having an opaque visual appearance and exhibiting a yield strength of greater than 0 Pascals, and
(d) 0.1 to 5 parts by weight, preferably 0.2 to 3 parts by weight, of a freeze thaw agent selected from the aforementioned polymers and mixtures thereof.

In one embodiment the personal care composition comprises based on 100 parts by weight of the composition:
(a) from about 2 to about 40 parts by weight of the at least one anionic surfactant,
(b) 0.2 to about 15 parts by weight of the at least one surfactant selected from the group consisting of amphoteric surfactants and zwitterionic surfactants,
(c) from 0 to about 6 parts, typically 1 to 6 parts, by weight of the electrolyte, and
(d) 0.1 to 5 parts by weight, preferably 0.2 to 3 parts by weight, of a freeze thaw agent selected from the aforementioned polymers and mixtures thereof.

In one embodiment the personal care composition comprises based on 100 parts by weight of the composition:
(a) from about 2 to about 40 parts by weight of at least one anionic surfactant,
(b) 0.2 to about 15 parts by weight of one or more surfactants selected from amphoteric surfactants, zwitterionic surfactants, and mixtures thereof, and
(c) from 0 to about 6 parts by weight of electrolyte in an amount effective to, in combination with components (a) and (b), provide a structured surfactant composition having an opaque visual appearance and exhibiting a yield strength of greater than 0 Pascals,
(d) 0.1 to 5 parts by weight, preferably 0.2 to 3 parts by weight, of a freeze thaw agent selected from the aforementioned polymers and mixtures thereof, and
(e) optionally from about 1 parts by weight to about 40 parts by weight, of a benefit agent selected from skin conditioning oils and mixtures thereof.

In one embodiment, the aqueous structured surfactant and/or personal care composition of the present invention each comprise, based on 100 pbw of the composition, from about 10 to about 90 pbw, more typically from about 20 to about 80 pbw, water, and 0.1 to 5 parts by weight, preferably 0.2 to 3 parts by weight, of a freeze thaw agent selected from the aforementioned polymers and mixtures thereof.

In one embodiment, the total amount of surfactants the aqueous structured surfactant and/or personal care compositions of the present invention consists essentially of the at least one anionic surfactant. In one embodiment, the total amount of surfactants the aqueous structured surfactant and/or personal care compositions of the present invention consists of the at least one anionic surfactant.

In one embodiment, the aqueous structured surfactant and/or personal care composition of the present invention each exhibit a pH of from about 2.8 to about 12, more typically from about 4 to about 10.0, and even more typically from about 4.5 to about 8; or 4.5 to 6.5.

Specific Structured Surfactants

In one embodiment, total amount of all surfactants, including all anionic surfactants, amphoteric/zwitterionic surfactants, non-ionic surfactants, and cationic surfactant, contained in the aqueous structured surfactant composition and/or personal care composition of the present invention is from about 10 pbw to about 40 pbw, more typically from about 15 pbw to about 35 pbw, and even more typically from about 12.5 pbw to about 30 pbw or about 15 pbw to about 30 pbw, based on 100 parts by weight of the aqueous structured surfactant and/or personal care composition.

(a) Anionic Surfactant

Suitable anionic surfactants are described above in the section entitled "Anionic Surfactants".

In one embodiment, the aqueous structured surfactant and/or personal care composition of the present invention each comprise, based on 100 pbw of the composition, from about 0.5 to about 40 pbw, more typically from about 1 pbw to about 30 pbw, and even more typically from about 5 pbw to about 30 pbw, of the at least one anionic surfactant.

In one embodiment, the amount of anionic surfactant contained in the structured surfactant and/or personal care composition of the present invention is from 1 to 75 wt %, more typically from about 5 to about 30 wt %, of the total amount of surfactant contained in the structured surfactant and/or personal care composition of the present invention.

(b) Amphoterics/Zwitterionics

Suitable amphoteric surfactants are described above in the section entitled "Amphoteric Surfactants". Suitable zwitterionic surfactants are described above in the section entitled "Zwitterionic Surfactants".

In one embodiment, the aqueous structured surfactant and/or personal care composition of the present invention each comprise, based on 100 pbw of the composition, from about 0.1 to about 25 pbw, more typically, from about 0.5 to about 15 pbw, of one or more amphoteric surfactants and/or zwitterionic surfactants ("amphoteric/zwitterionic surfactants").

In one embodiment, the amount of one or more amphoteric/zwitterionic surfactants contained in the structured surfactant and/or personal care composition of the present invention is from 0 to less than 100 wt %, more typically from 0 to about 80 wt %, even more typically from about 20 to about 70 wt %, and still more typically from about 30 to about 60 wt %, of the total amount of surfactant contained in the structured surfactant and/or personal care composition of the present invention.

In one embodiment, the amount of one or more amphoteric/zwitterionic surfactants contained in the structured surfactant and/or personal care composition of the present invention is from 0 to less than about 50 wt %, more typically from about 5 to about 45 wt %, of the total amount of surfactant contained in the structured surfactant and/or personal care composition of the present invention.

In one embodiment, the amount of one or more amphoteric/zwitterionic surfactants contained in the structured surfactant and/or personal care composition of the present invention is from 50 to less than 100 wt %, more typically from about 55 to about 95 wt %, of the total amount of surfactant contained in the structured surfactant and/or personal care composition of the present invention.

In one embodiment, the aqueous structured surfactant and/or personal care composition of the present invention are each substantially free of amphoteric/zwitterionic surfactants. In one embodiment, the aqueous structured surfactant and/or personal care composition of the present invention are each free of amphoteric/zwitterionic surfactants.

(c) Nonionics

Suitable non-ionic surfactants are described above in the section entitled "Non-ionic Surfactants".

In one embodiment, the aqueous structured surfactant and/or personal care composition of the present invention each comprise, based on 100 pbw of the composition, from about 0.1 to about 25 pbw, more typically, from about 0.5 to about 10 pbw, of one or more non-ionic surfactants.

In one embodiment, the amount of one or more nonionic surfactants contained in the structured surfactant and/or personal care composition of the present invention is from 0 to less than 100 wt %, more typically from 0 to about 80 wt %, even more typically form about 20 to about 70 wt %, and still more typically from about 30 to about 60 wt %, of the total amount of surfactant contained in the structured surfactant and/or personal care composition of the present invention.

In one embodiment, the amount of one or more nonionic surfactants contained in the structured surfactant and/or personal care composition of the present invention is from 0 to less than about 50 wt %, more typically from about 5 to about 45 wt %, of the total amount of surfactant contained in the structured surfactant and/or personal care composition of the present invention.

In one embodiment, the amount of one or more nonionic surfactants contained in the structured surfactant and/or personal care composition of the present invention is from 50 to less than 100 wt %, more typically from about 55 to about 95 wt %, of the total amount of surfactant contained in the structured surfactant and/or personal care composition of the present invention.

In one embodiment, the aqueous structured surfactant and/or personal care composition of the present invention are each substantially free of nonionic surfactants. In one embodiment, the aqueous structured surfactant and/or personal care composition of the present invention are each free of nonionic surfactants.

(d) Cationics

Suitable cationic surfactants are described above in the section entitled "Cationic Surfactants".

In one embodiment, the aqueous structured surfactant and/or personal care composition of the present invention each comprise, based on 100 pbw of the composition, from about 0.1 to about 25 pbw, more typically, from about 0.5 to about 10 pbw, of one or more cationic surfactants.

In one embodiment, the amount of one or more cationic surfactants contained in the structured surfactant and/or personal care composition of the present invention is from 0 to 10 wt %, more typically from about 0 to about 5 wt %, and even more typically from about 0 to about 3 wt % of the total amount of surfactant contained in the structured surfactant and/or personal care composition of the present invention.

In one embodiment, the aqueous structured surfactant and/or personal care composition of the present invention are each substantially free of cationic surfactants. In one embodiment, the aqueous structured surfactant and/or personal care composition of the present invention are each free of cationic surfactants.

Electrolytes

In one embodiment, the personal care composition further comprises, based on 100 pbw of the composition, from greater than 0 to about 30 pbw, more typically from about 0.1 to about 20 pbw, still more typically from about 0.25 to about 10 pbw, still more typically from about 0.5 pbw to about 6 pbw, still more typically from about 0.5 pbw to about 5 pbw, of one or more non-surfactant electrolytes.

Suitable non-surfactant electrolytes include, for example, alkali metal, alkaline earth, ammonium and substituted ammonium salts of inorganic acids, including, for example, one or more of calcium bromide, calcium chloride, calcium carbonate, potassium chloride, sodium chloride, potassium iodide, sodium bromide, magnesium chloride, sodium sulfate, calcium nitrate, ammonium bromide, ammonium sulfate, and ammonium nitrate.

Suitable electrolytes include salts of multivalent anions, such as one or more of potassium pyrophosphate, potassium tripolyphosphate, and sodium or potassium citrate, salts of multivalent cations such as zinc halides, barium chloride and calcium nitrate, salts of monovalent cations with monovalent anions, including alkali metal or ammonium halides, alkali metal or ammonium nitrates, and polyelectrolytes, such as uncapped polyacrylates, polymaleates, or polycarboxylates, lignin sulfonates, or naphthalene sulfonate formaldehyde copolymers.

Electrolyte may be added as a separate component or in combination with other components of the composition of the present invention.

Preservatives, pH Modifiers, and Sugars

The structured surfactant personal care composition of the present invention may optionally further comprise one or more preservatives, such as benzyl alcohol, methyl paraben, propyl paraben, or imidazolidinyl urea, and DMDM hydantoin, and may optionally further comprise one or more pH adjusting agents, such as citric acid, succinic acid, phosphoric acid, sodium hydroxide, or sodium carbonate.

The composition may optionally further comprise, based on 100 pbw weight of the composition up to about 10 pbw of other components, such as, sugars and rheology modifiers.

Suitable sugars include monosaccharides and polysaccharides, such as, for example, glucose or guar gum. For example, cationic polysaccharides, non-ionic polysaccharides, amphoteric polysaccharides, zwitterionic polysaccharides, hydrophobically substituted, or anionic polysaccharides may be employed. A substituted (or modified or derivitized) polysaccharide is typically a polysaccharide to which a functional group is added or grafted onto the polysaccharide. For example, a hydrophobically substituted polysaccharide is one to which a hydrophobic chain is added onto the polysaccharide, for example a hydrophobic chain could be C3-4 linear or branched alkyl chain.

Pearlescent Additives

Pearlescent additives, also known as pearlizing agents, are often added to beauty and personal care products such as hair and skin care products to provide a pearly appearance to the products. Chemicals which are tiny (micron size) needles or platelets often exhibit this pearly appearance. Materials which exhibit this effect are ethylene glycol mono- and distearate, TiO$_2$ coated mica, bismuth oxychloride, and natural mother of pearl. Many organic materials exhibit this pearlescence provided they can be produced in an appropriate needle or platelet shape. Ethylene glycol distearate (EGDS) or ethylene glycol monostearate (EGMS) are the most commonly utilized pearlizing agents.

A stable, mild free flowing cold pearlizing concentrate is typically prepared using i) a pearlizing agent, preferably a glycol stearate; ii) a nonionic surfactant; iii) an amphoteric surfactant emulsifier and stabilizer; iv) a glycol emulsifier; and v) water; to obviate the use of cocodiethanolamide and provide excellent compatibility with any ionic surfactant. The pearlizing agent comprises from about 5% to about 40%, preferably from about 10% to about 30% and most preferably from about 15% to about 25%, by weight based on the total weight of the concentrate.

The pearlizing agent can be selected from the group consisting of hydroxyl stearate, polyethylene glycol mono- and di-stearates, ethylene glycol mono- and distearates, stearic monoethanolamide, and mixtures thereof. The preferred agents are polyethylene glycol mono- and distearates, and ethylene glycol mono- and di-stearates. The most preferred pearlizing agents for use are: ethylene glycol mono- and di-stearates.

Benefit Agents

In one embodiment, the personal care composition further comprises one or more personal care benefit agents. At least one personal care benefit agent comprises a water insoluble additive (oil, mica, exfoliation beads, emollients, moisturizers, pearlizing agent, a silicone hair conditioning agent, an antidandruff ingredient, a glycol emulsifier). The composition of the present invention is designed to suspend this water insoluble additive such that it remains suspended after a freeze-thaw test.

Suitable benefit agents include materials that provide a personal care benefit, such as moisturizing, conditioning, or a sensory benefit, to the user of the personal care composition, such as, for example, emollients, conditioners, moisturizers, polymers, vitamins, abrasives, UV absorbers, antimicrobial agents, anti-dandruff agents, fragrances, and/or appearance modifying additives, such as, for example, colored particles or reflective particles, which may be in the form of a solid, liquid, or gas and may be insoluble or are only partly soluble in the personal care composition. Mixtures of the benefit agents may be used.

In one embodiment, the benefit agent comprises an oil useful as an emollient, or conditioner for the skin or hair. Suitable oils, include for example, vegetable oils, such as arachis oil, castor oil, cocoa butter, coconut oil, corn oil, cotton seed oil, olive oil, palm kernel oil, rapeseed oil, safflower seed oil, sesame seed oil, and soybean oil, esters of ($C_{12}$-$C_{22}$) carboxylic acids, such as butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate, animal fats, such as lanoliin, mink oil, and tallow, hydrocarbon oils, such as mineral oils and petrolatum, and silicone oils, such as polydimethylsiloxanes, polydiethylsiloxanes, polymethylphenylsiloxanes, alkoxylated polyorganosiloxanes, amino-substituted polyorganosiloxanes, amido-substituted polyorganosiloxanes, and mixtures thereof.

In one embodiment, the benefit agent comprises a moisturizer. Suitable moisturizers include, for example, glycerin and hyaluronic acid.

In one embodiment, the benefit agent comprises a cationic polymer and/or an amphoteric polymer. Suitable cationic polymers include synthetic polymers that comprise monomeric units derived from one or more amine- and/or quaternary ammonium-substituted monomers and natural polymers that have been derivatized to include amine- and/or quaternary ammonium-containing pendant groups, each typically having a cationic charge density of from about 0.1 to 4 meq/g. Suitable cationic polymers include, for example: copolymers of 1-vinyl-2-pyrrolidine and 1-vinyl-3-methyl-imidazolium salts (such as Polyquaternium-16), copolymers of 1-vinyl-2-pyrrolidine and dimethylaminoethyl methacrylate (such as Polyquaternium-11), cationic diallyl quaternary ammonium-containing polymers including, for example, dimethyldiallyammonium chloride homopolymers and copolymers of acrylamide and dimethyldiallylammonium chloride (such as Polyquaternium 6 and Polyquaternium 7), cationic polyacrylamides, cationic polysaccharide polymers, such as, for example, cationic cellulose derivatives, cationic starch derivatives, and cationic guar gum derivatives, such as salts of hydroxyethyl cellulose reacted with trimethyl ammonium substituted epoxide (such as Polyquaternium 10), polymeric quaternary ammonium salts of hydroxyethyl cellulose reacted with lauryl dimethyl ammonium-substituted epoxide (such as Polyquaternium 24) and guar hydroxypropyltrimonium chloride, and cationic protein derivatives, such as cocodimonium hydroxypropyl hydrolyzed wheat protein. Suitable amphoteric polymers are polymers that contain both anionic groups, such as phosphate, phosphonate, sulphate, sulphonate or carboxylic acid groups, and cationic groups, such as tertiary amino groups or quaternary ammonium groups, on the same polymer molecule. Suitable amphoteric polymers include, for example, amphoteric acrylic copolymers, such as octylacrylamide/acrylate/butylaminoethyl methacrylate copolymers, and amphoteric polysaccharide compounds obtained by grafting and polymerization of cationic pendant groups, e.g., dimethyldiallylammonium chloride groups, onto anionic polysaccharide, for example, a sodium carboxymethyl-cellulose, backbone. Aqueous compositions containing the polymer of the present invention, one or more surfactants and/or non-surfactants salts, and a cationic polymer and/or amphoteric polymer exhibit an enhanced thickening efficiency compared to analogous compositions that lack the cationic polymer and/or amphoteric polymer.

In one embodiment, the benefit agent comprises an anti-dandruff agent. Suitable anti-dandruff agents include, for example, particulate, crystalline anti-dandruff agents, such as sulfur, selenium disulfide, and heavy metal salts of pyridinethione, such as zinc pyrithione, as well as soluble anti-dandruff agents, such as ketoconazole.

In one embodiment, the benefit agent comprises a UV radiation absorber. Suitable UV radiation absorbers include, for example, sodium benzotriazolyl butylphenol sulfonate.

The personal care composition according to the present invention may optionally further comprise, based on 100 pbw of the personal care composition and independently for each such ingredient, up to about 50 pbw, typically from 0.5 pbw to about 20 pbw, of other ingredients in addition to the one or more benefit agents, including, for example, preservatives such as benzyl alcohol, methyl paraben, propyl paraben and imidazolidinyl urea, pH adjusting agents such as citric acid, succinic acid, phosphoric acid, sodium hydroxide, sodium carbonate, dyes, and sequestering agents such as disodium ethylenediamine tetra-acetate. Other examples of ingredients commonly used in personal care compositions, which are suitable for use in the compositions of the present invention, are known and are described in, for example, in *Cosmetic Ingredient Handbook*, Eighth Edition, 2000.

In one embodiment of the personal care composition, the polymer of the present invention is an effective thickener, in other words the polymer increases the viscosity of the personal care composition, that is responsive, but not overly sensitive, to salt content and/or surfactant content, particularly at a pH of greater than or equal to 6.5. More specifically, the viscosity of an aqueous composition comprising the polymer of the present invention typically increases with increasing surfactant content and/or non-surfactant salt content in a predictable and proportional manner and does not typically undergo undesirably large changes in viscosity in response to relatively small changes in the amount of surfactants and/or non-surfactant salts.

In one embodiment of the personal care composition, the polymer of the present invention imparts a yield strength to the composition greater than 0 Pa, more typically of from about 0.01 Pa, and even more typically from about 0.1 to about 10 Pa, and even more typically about 4 Pa, and even more typically about 2 Pa. A non-zero yield strength is useful for suspending water insoluble particles in the personal care composition. As previously mentioned, the polymer of the present invention typically provides a yield strength of greater than 0 Pa even in the absence of any cross-linking of the polymer.

In one embodiment of the personal care composition wherein the personal care composition has a pH of greater than or equal to 5.5, the polymer of the present invention provides thickening properties and imparts a non-zero yield strength in the presence of surfactant without imparting an optically turbid appearance to the composition, thus allowing formulation of optically clear compositions having a non-zero yield strength.

In one embodiment of the personal care composition, typically wherein the personal care composition has a pH of greater than or equal to about 6.5, the polymer of the present invention provides thickening properties and imparts a non-zero yield strength in the presence of surfactants and/or non-surfactant salts and imparts to the composition clear, transparent visual appearance, for example, a transmittance at 600 nm of greater than 95%.

In one embodiment of the personal care composition, typically wherein the personal care composition has a pH of less than about 6.5, the polymer of the present invention provides thickening properties and imparts a non-zero yield strength in the presence of surfactants and/or non-surfactant salts, and imparts an opaque visual appearance to the composition. Also, a higher yield strength can typically be obtained with given polymer content at a pH of less than 6, compared to a composition having a pH of greater than or equal to 6.5.

The composition according to the invention can be provided in any form and can be used in multiple ways.

Thus, it can be in the form of a viscoelastic or viscous medium to be deposited as such, in particular by applying, directly on the surfaces to be cleaned or rinsed, or
on a sponge or another substrate (woven or nonwoven article made of cellulose, for example) before being applied to the surface of skin or hair to be treated.

It can be in the form of:
a viscoelastic or viscous medium to be diluted in water (optionally with the addition of another solvent) before being applied to body;
a viscoelastic or viscous medium held in a water-soluble bag.
a foam,
an aerosol.

In one embodiment of the personal care composition the polymer of the present invention provides high foam volume. In an embodiment of the personal care composition that comprises a cationic polymer, the polymer of the present invention provides high foam volume and reduces drainage, resulting in a wet, creamy, shiny, white foam.

In one embodiment of the personal care composition the polymer of the present invention provides good sensory properties, such as, for example a smooth, velvety feel and a lack of tacky feeling on the skin.

In one embodiment of the personal care composition, the polymer of the present invention is easily rinsed from the skin with water, leaving minimal or no perceptible polymer residue on the skin.

The composition forming the subject matter of the invention can comprise, depending on its application, from 0.1 to 10% of its weight of at least one of the selected freeze thaw stability polymers, for example, HASE polymers.

The pH of the composition or the pH of use of the composition according to the invention can vary, depending on the applications and the specific body part to be treated. The pH of the compositions is not critical and can be in the range of from about 2 to about 12, preferably from about 4 to about 10 and most preferably from about 5 to about 8. The pH can be adjusted using a buffer such as, but not limited to, citric acid.

Additional Components

Non-essential optional components can be utilized in concentrates of the present invention as a convenient means of incorporation into beauty and personal care products. Such conventional optional ingredients are well known to those skilled in the art, e.g., preservatives such as benzyl alcohol, methyl paraben, propyl paraben and imidazolidinyl urea; thickeners and viscosity modifiers such as block polymers of ethylene oxide and propylene oxide, e.g. ANTAROX F-88 (Rhodia, Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; natural oils and petroleum derivatives, dyes; and sequestering agents such as disodium ethylenediamine tetra-acetate. Such agents generally are used individually at levels of from 0% to about 15%, preferably from 0.01% to about 5.0% by weight of the concentrate.

The pH of the compositions is not critical and can be in the range of from about 2 to about 12, preferably from about 4 to about 10 and most preferably from about 4.5 to about 8. The pH can be adjusted using a buffer such as, but not limited to, citric acid.

Body Wash

In one embodiment, the personal care composition is a body wash that comprises, based on 100 pbw of the composition, from about 0.1 to about 5 pbw, more typically from about 0.5 to about 3 pbw, from of the polymer of the present invention, from about 1 to about 35 pbw, more typically from about 1 to about 25 pbw of one or more surfactants, more typically of a mixture of one or more anionic surfactants with one or more zwitterionic or amphoteric surfactants, nonionic surfactants, and optionally, one or more non-surfactant salts.

Hand Soap

The present invention may also be included in a liquid hand soap. Such a soap composition includes (a) water; (b) a primary hand soap composition; (c) a biocide; and (d) the freeze thaw stability polymer, for example, HASE polymer, of the present invention.

"Primary hand soap formulation" refers to the collective ingredients of the primary hand soap composition of the invention exclusive of the surfactant component; optionally including a biocide. The primary soap formulation may be referred to on either a wet or dry basis. "Primary surfactant" means a surfactant included in the primary hand soap composition. The primary hand soap surfactants may be anionic surfactants, cationic surfactants, nonionic surfactants and so forth. The amount of primary surfactant(s) to be added to the composition of the present invention generally will not exceed more than 20-25% by weight.

The composition may also include other additives such as thickeners, emollients, chelating and sequestering agents, fragrances, coloring agents, opacifying agents, pearlizing agents, vitamins and the like. For example, the composition may include a polymer viscosifier or thickener such as hydroxyethyl cellulose to make the composition more aesthetically pleasing.

Shampoo

The compositions of the present invention containing freeze thaw stability polymer, for example, HASE polymer, may be employed as shampoo. When the invention is used in a shampoo, the shampoo will typically contain a detersive surfactant. These include anionic, cationic, nonionic surfactants, amphoteric surfactants, and zwitterionic surfactants. The shampoos typically contain from about 0% to about 20% of amphoteric surfactants, about 0% to about 20% of zwitterionic surfactants, and from about 0% to about 20% of anionic surfactants, a total surfactant level of from about 7% to about 30%.

Shampoos may also include a silicone compound added to the composition in an amount sufficient to impart improved combing and improved feel, such as softness, to the hair after shampooing. The silicone hair conditioning agent will be used in the shampoo compositions hereof at levels of from about 0.1% to about 10% by weight of the composition, preferably from about 0.5% to about 8%. The silicone compound is a nonvolatile silicone fluid, generally a nonfunctionalized siloxane having a viscosity of from about 5 to about 600,000 cs (centistoke), and preferably from about 350 to about 10,000 cs, at 25° C. The so-called "rigid silicones", as described in U.S. Pat. No. 4,902,499, herein incorporated by reference, having a viscosity above 600,000 cs at 20° C., e.g., 700,000 cs plus, and a weight average molecular weight of at least about 500,000, also are useful. The silicone compound is typically a polydimethylsiloxane, typically a linear polydimethylsiloxane terminated at each end with a trimethylsilyl group.

Shampoos may also include a silicone resin. In general, silicone resins have a sufficient level of trifunctional and tetrafunctional siloxane monomer units (and hence, a sufficient level of crosslinking) such that they dry down to a rigid, or hard, film. Silicone materials which have at least about 1.1 oxygen atoms per silicon atom will generally be silicone resins. The weight ratio of the nonvolatile silicone fluid component to the silicone resin component is from about 4:1 to about 400:1.

The shampoo of the present invention can contain a variety of non-essential optional components suitable for rendering such compositions more acceptable. Such conventional optional ingredients are well known to those skilled in the art, e.g., preservatives such as benzyl alcohol, methyl paraben, propyl paraben and imidazolidinyl urea; thickeners and viscosity modifiers such as, but not limited to, block polymers of ethylene oxide and propylene oxide, e.g. ANTAROX F-88 (Rhodia Inc.), sodium chloride, sodium sulfate, polyvinyl alcohol, and ethyl alcohol; pH adjusting agents such as citric acid, succinic acid, phosphoric acid, sodium hydroxide, sodium carbonate; perfumes; dyes; and sequestering agents such as disodium ethylenediamine tetra-acetate. Such agents generally are used individually at levels of from about 0.01% to about 10%, preferably from 0.5% to about 5.0% by weight of the composition. The shampoo may also include antidandruff agents such as pyrithione salts, preferably zinc pyrithione, as disclosed by PCT application number PCT/

US98/04139, filed Mar. 4, 1998 and published as WO 98/41505, incorporated herein by reference in its entirety.

Hair Removal Personal Care Products

The compositions of the present invention containing freeze thaw stability polymer, for example, HASE polymer, may be employed as foam foaming shaving gels and shaving creams. Typical foaming shaving gels are disclosed by U.S. Pat. No. 5,902,778 to Hartmann, et al; U.S. Pat. No. 5,858,343 to Szymczak; and U.S. Pat. No. 5,853,710 to Dehan, et al, all of which are incorporated herein by reference in their entirety. Typical foam shaving creams are disclosed by U.S. Pat. No. 5,686,024 to Dahanayake, et al; U.S. Pat. No. 5,415,860 to Beucherie, et al; U.S. Pat. No. 5,902,574 to Stoner, et al; and U.S. Pat. No. 5,104,643 to Grollier, et al, all of which are incorporated herein by reference in their entirety.

The compositions of the present invention containing freeze thaw stability polymer, for example, HASE polymer, are also useful in a depilatory. An example of a depilatory is disclosed in U.S. Pat. No. 4,734,099 to Cyprien incorporated herein by reference in its entirety.

Makeup Remover

The present invention may also be a makeup remover. Typical makeup removers are described by U.S. Pat. No. 5,607,680 incorporated herein by reference in its entirety. More particularly, according to the present invention, the subject compositions permit the skin and/or the eyes to be cleansed, and/or makeup to be removed efficaciously therefrom, without any attendant irritation or any discomfort whatever to the user.

Such compositions of this invention present the advantage of effecting removal of makeup in the absence of an obligatory rinsing step; this is especially advantageous in the event of application to a skin having certain skin disorders or conditions, or in the case of application to the skin under conditions not conducive to rinsing with water, such as when traveling.

An advantage presented by the compositions according to the invention is that they are well suited for the removal of any type of makeup product, including waterproof makeup products for the eyes or makeup products having fat-rich textures, such as foundations, powders and lipsticks that are particularly suited for making-up actors.

Another notable advantage presented by the compositions according to the invention is the fact that said compositions may be employed in hot countries where the use of excessively fat-rich makeup removers gives the sensation of weight or heaviness on the skin which is often difficult to bear.

This type of formulation is advantageously formulated into the subject compositions in an amount ranging from 0.5% to 5% by weight, and preferably in an amount ranging from 1% to 2% by weight, relative to the total weight of the composition.

The diesters advantageously used for the preparation of the makeup remover compositions according to the invention are those obtained by reacting a saturated or unsaturated fatty acid having from 16 to 22 carbon atoms with a polyethylene glycol in which the number of the oxyethylene recurring structural units ranges from 150 to 175.

Even more preferably, the diesters formulated into the makeup remover compositions are selected from among polyethylene glycol distearates, polyethylene glycol dipalmitates, polyethylene glycol dioleates and polyethylene glycol dibehenates.

The diester of the makeup remover compositions is advantageously present in an amount generally ranging from 1% to 5% by weight, and preferably in an amount ranging from 1% to 2% by weight, relative to the total weight of the composition.

In addition, the compositions according to the invention comprise at least one fat constituting the fatty phase, preferably selected from among fatty alcohols and oils having a melting point above 30° C.

Even more preferably, fatty alcohols are employed selected from among cetyl alcohol, stearyl alcohol and a mixture thereof. Among the oils having a melting point above 30° C., shea butter, illipe butter and cocoa butter are particularly representative.

In another especially preferred embodiment of the present invention, the aqueous phase comprising the compositions according to the invention represents at least 90% by weight, preferably at least 95% by weight and, even more preferably, at least 97% by weight of the total weight of the composition.

The subject composition can optionally comprise, in addition, at least one perfume, and at least one preservative, in an amount ranging from 0.1% to 1% by weight relative to the total weight of the composition.

The compositions according to this invention may be formulated as an emulsion (water-in-oil, oil-in-water), a dispersion, a gel, a cream, a lotion or a foam, or any other form typically employed in the cosmetics art.

The present invention also features a technique for removing makeup from the skin, which comprises applying a composition as described above to skin and/or to eyes which have been made up. As indicated above, the application of this composition to the skin does not result in the generation of foam.

This technique optionally includes a rinsing step, which is not mandatory.

Fracturing Fluids

The compositions of the present invention may each be used in the fracturing fluid in an amount of from, for example, 0.01 to 1% by weight of the fluid.

Crosslinking Agent

A crosslinking agent may be used with the fracturing fluids. The crosslinking agents used include Group 4 transition metal compound crosslinking agents. The crosslinking agent may include zirconium, titanium and hafnium crosslinking agents, and combinations of these, and may include organometallic compounds. In particular, organo-zirconium and titanium crosslinking agents are useful. Examples of suitable zirconium crosslinking agents include zirconium triethanolamine, L-glutamic acid-triethanolamine-zirconium, zirconium diethanolamine, zirconium tripropanolamine, and zirconium lactate complexes, and/or the related salts, and/or their mixtures. Examples of titanium crosslinking agents include titanium triethanolamine, dihydroxybis(ammonium lactato)titanium, and titanium acetylacetonate. The crosslinking agent may be included in the fluid in an amount of from about 0.01% to about 1.5% by weight of the fluid, more particularly, from about 0.02% to about 0.3% by weight of the fluid.

Buffering Agent

A hydroxyl ion releasing agent or buffering agent may be employed to adjust the pH or buffer the fluid, i.e., moderate amounts of either a strong base or acid may be added without causing any large change in pH value of the fluid. These may useful in changing the rate of crosslinking. Alkaline amine or polyamine compounds that are useful to raise the pH to the desirable level are outlined in U.S. Pat. No. 4,579,670, and include tetramethylenediamine, triethylenetetramine, tetraethylenepentamine (TEPA), diethylenetriamine, triethylenediamine, triethylenepentamine, ethylenediamen and similar compounds. The alkali metal hydroxides, e.g., sodium hydroxide, and carbonates can also be used. Other acceptable materials are $Ca(OH)_2$, $Mg(OH)_2$, $Bi(OH)_3$, $Co(OH)_2$, $Pb(OH)_2$, $Ni(OH)_2$, $Ba(OH)_2$ and $Sr(OH)_2$. At temperatures above about 175° F. (79° C.), potassium fluoride (KF) may be used to prevent the precipitation of MgO when $Mg(OH)_2$ is used as a base, i.e., hydroxyl ion releasing agent.

In various embodiments, the buffering agent is a combination of a weak acid and a salt of the weak acid; an acid salt with a normal salt; or two acid salts. Examples of suitable buffering agents are $NaH_2PO_4$—$Na_2PO_4$; sodium carbonate-sodium bicarbonate; and sodium bicarbonate, or other like agents. By employing a buffering agent instead of merely a hydroxyl ion producing material, a fluid is provided which is more stable to a wide range of pH values found in local water supplies and to the influence of acidic materials located in formations and the like.

Gas Component

The fracturing fluids may contain a gas component, as discussed above. The gas component may be provided from any suitable gas that forms an energized fluid or foam when introduced into the aqueous medium. See, for example, U.S. Pat. No. 3,937,283 (Blauer, et al.), hereinafter incorporated by reference. The gas component may comprise a gas selected from nitrogen, air, argon, carbon dioxide, and any mixtures thereof. Particularly useful are the gas components of nitrogen or carbon dioxide, in any quality readily available. The gas component may assist in the fracturing, and also the capacity of the fluid to carry solids, such as proppants. The presence of the gas also enhances the flowback of the fluid to facilitate cleanup. The fluid may contain from about 10% to about 90% volume gas component based upon total fluid volume percent, more particularly from about 20% to about 80% volume gas component based upon total fluid volume percent, and more particularly from about 30% to about 70% volume gas component based upon total fluid volume percent.

Breaker

Fracturing fluids based on the invention may also comprise a breaker. The purpose of this component is to "break" or diminish the viscosity of the fluid so that this fluid is more easily recovered from the formation during cleanup. With regard to breaking down viscosity, oxidizers, enzymes, or acids may be used. Breakers reduce the polymer's molecular weight by the action of an acid, an oxidizer, an enzyme, or some combination of these on the polymer itself. The breakers may include persulfates such as ammonium persulfate, sodium persulfate, and potassium persulfate, bromates such as sodium bromate and potassium bromate, periodates, metal peroxides such as calcium peroxide, chlorites, and the like, and the combinations of these breakers, live or encapsulated.

Proppant

Embodiments of the invention used as fracturing fluids may also include proppant particles that are substantially insoluble in the fluids of the formation. Proppant particles carried by the treatment fluid remain in the fracture created, thus propping open the fracture when the fracturing pressure is released and the well is put into production. Suitable proppant materials include, but are not limited to, sand, walnut shells, sintered bauxite, glass beads, ceramic materials, naturally occurring materials, or similar materials. Mixtures of proppants can be used as well. If sand is used, it will typically be from about 20 mesh (0.841 mm) to about 100 mesh (0.0059 mm) in size. With synthetic proppants, mesh sizes of about 8 (0.937 mm) or greater may be used. Naturally occurring materials may be underived and/or unprocessed naturally occurring materials, as well as materials based on naturally occurring materials that have been processed and/or derived. Suitable examples of naturally occurring particulate materials for use as proppants include, but are not necessarily limited to: ground or crushed shells of nuts such as walnut, coconut, pecan, almond, ivory nut, brazil nut, etc.; ground or crushed seed shells (including fruit pits) of seeds of fruits such as plum, olive, peach, cherry, apricot, etc.; ground or crushed seed shells of other plants such as maize (e.g., corn cobs or corn kernels), etc.; processed wood materials such as those derived from woods such as oak, hickory, walnut, poplar, mahogany, etc. including such woods that have been processed by grinding, chipping, or other form of particalization, processing, etc. Further information on nuts and composition thereof may be found in Encyclopedia of Chemical Technology, Edited by Raymond E. Kirk and Donald F. Othmer, Third Edition, John Wiley & Sons, Volume 16, pages 248-273 (entitled "Nuts"), Copyright 1981, which is incorporated herein by reference.

The concentration of proppant in the fluid can be any concentration known in the art, and will preferably be in the range of from about 0.03 to about 3 kilograms of proppant added per liter of liquid phase. Also, any of the proppant particles can further be coated with a resin to potentially improve the strength, clustering ability, and flow back properties of the proppant.

Aqueous Media

The aqueous medium of the fracturing fluids of the present invention may be water or brine. In those embodiments of the invention where the aqueous medium is a brine, the brine is water comprising an inorganic salt or organic salt. Inorganic salts may include alkali metal halides, such as potassium chloride. The carrier brine phase may also comprise an organic salt, such as sodium or potassium formate. Inorganic divalent salts include calcium halides, such as calcium chloride or calcium bromide. Sodium bromide, potassium bromide, or cesium bromide may also be used. The salt may be chosen for compatibility reasons, i.e., where the reservoir drilling fluid used a particular brine phase and the completion/clean up fluid brine phase is chosen to have the same brine phase. Typical brines have an electrolyte concentraton of 1 to 50 wt. % based on total weight of the brine on an aqueous basis, for example 1 to 10 or 20 wt. %.

Fiber Component

A fiber component may be included in the fracturing fluids of the invention to achieve a variety of properties including improving particle suspension, and particle transport capabilities, and gas phase stability. Fibers used may be hydrophilic or hydrophobic in nature, but hydrophilic fibers may be useful for some applications. Fibers can be any fibrous material, such as, but not necessarily limited to, natural organic fibers, comminuted plant materials, synthetic polymer fibers (by non-limiting example polyester, polyaramide, polyamide, novoloid or a novoloid-type polymer), fibrillated synthetic organic fibers, ceramic fibers, inorganic fibers, metal fibers, metal filaments, carbon fibers, glass fibers, ceramic fibers, natural polymer fibers, and any mixtures thereof. Particularly useful fibers are polyester fibers coated to be highly hydrophilic, such as, but not limited to, DACRON polyethylene terephthalate (PET) fibers available from Invista Corp. Wichita, Kans., USA, 67220. Other examples of useful fibers include, but are not limited to, polylactic acid polyester fibers, polyglycolic acid polyester fibers, polyvinyl alcohol fibers, and the like. When used in fluids of the invention, the fiber component may be included at concentrations from about 1 to about 15 grams per liter of the liquid phase of the fluid, in certain applications the concentration of fibers may be from about 2 to about 12 grams per liter of liquid, and in others from about 2 to about 10 grams per liter of liquid.

Other Optional Ingredients

Fluid embodiments of fracturing fluids of the invention may further contain other additives and chemicals that are known to be commonly used in oilfield applications by those skilled in the art. These include, but are not necessarily limited to, materials such as surfactants in addition to those mentioned herein, clay stabilizers such as tetramethyl ammonium chloride and/or potassium chloride, breaker aids in addition to those mentioned herein, oxygen scavengers, alcohols, scale inhibitors, corrosion inhibitors, fluid-loss additives, bactericides, and the like. Also, they may include a co-surfactant to optimize viscosity or to minimize the formation of stable emulsions that contain components of crude oil or a polysaccharide or chemically modified polysaccharide, polymers such as cellulose, derivatized cellulose, guar gum, derivatized guar gum, xanthan gum, or synthetic polymers such as polyacrylamides and polyacrylamide copolymers, oxidizers such as ammonium persulfate and sodium bromate, and biocides such as 2,2-dibromo-3-nitrilopropionamine. A derivitized (or modified) polysaccharide is typically a polysaccharide to which a functional group is added or grafted onto the polysaccharide. For example, a hydrophobically derivitized (or hydrophobically modified) polysaccharide is one to which a hydrophobic chain is added onto the polysaccharide, for example a hydrophobic chain could be C3-4 linear or branched alkyl chain.

Aqueous fluid embodiments of the invention may also comprise an organoamino compound. Examples of suitable organoamino compounds include, but are not necessarily limited to, tetraethylenepentamine (TEPA), triethylenetetramine, pentaethylenehexamine, triethanolamine, and the like, or any mixtures thereof. When organoamino compounds are used in fluids of the invention, they are incorporated at an amount from about 0.01 wt % to about 2.0 wt % based on total liquid phase weight. The organoamino compound may be incorporated in an amount from about 0.05 wt % to about 1.0 wt % based on total weight of the fluid. A particularly useful organoamino compound is tetraethylenepentamine (TEPA).

Hydraulic Fracturing Techniques

The fluids of the invention may be used for hydraulically fracturing a subterranean formation. Techniques for hydraulically fracturing a subterranean formation are known to persons of ordinary skill in the art, and involve pumping (injecting) the fracturing fluid into the borehole and out into the surrounding formation. The fluid pressure is above the minimum in situ rock stress, thus creating or extending fractures in the formation. See Stimulation Engineering Handbook, John W. Ely, Pennwell Publishing Co., Tulsa, Okla. (1994), U.S. Pat. No. 5,551,516 (Normal et al.), "Oilfield Applications", Encyclopedia of Polymer Science and Engineering, vol. 10, pp. 328-366 (John Wiley & Sons, Inc. New York, N.Y., 1987) and references cited therein, the disclosures of which are incorporated herein by reference thereto. While the fractures are open at least a portion of the proppant is deposited in the fractures. Then the pressure in the subterranean formation is relieved causing the fractures to close but remain "propped open" by the proppant remaining in the fractures.

In the fracturing treatment, fluids of the present invention may be used in the pad treatment, the proppant stages, or both. The components of the liquid phase may be mixed on the surface. Alternatively, the fluid may be prepared on the surface and pumped down tubing while any gas component could be pumped down the annulus to mix down hole, or vice versa.

The fluids of the invention can have particular application for use in high temperature environments. In particular, the fluids may be used in treatments where temperatures of 120° C. to 230° C. or higher are encountered. The fluids may have particular application for use in environments of from 300° F. (148.9° C.), 325° F. (162.8° C.), 350° F. (176.7° C.) to 375° F. (190° C.), 400° F. (204.4° C.), 425° F. (218.3° C.) or 450° F. (232.2° C.).

In hydraulic fracturing the fracturing fluid is pumped into the targeted formation at a rate in excess of what can be dissipated through the natural permeability of the formation rock. The fracturing fluids result in a pressure build up until such pressure exceeds the strength of the formation rock. When this occurs, the formation rock fails and a so-called "fracture" is initiated. With continued pumping, the fracture grows in length, width and height.

At a predetermined time in the pumping process, solid particulate is typically added to the fluid that is being pumped. This particulate is carried down the well, out of the wellbore and deposited in the created fracture. It is the purpose of this specially designed particulate to keep the fracture from "healing" to its initial position (after pumping has ceased). The particulate is said to be propping open the fracture and is therefore designated as "proppant". The fracture, which is generated by the application of this stimulation technique, creates a conductive path to the wellbore for the hydrocarbon.

Typical proppant is selected from the group consisting of gravel, quartz sand grains, sintered bauxite, glass and ceramic beads, walnut shell fragments, or aluminum pellets. The fracturing fluid may also include a thermal stabilizer, for example sodium thiosulfate, methanol, ethylene glycol, isopropanol, thiourea, and/or sodium thiosulfite. Resin coated proppants are also employed in the art.

The fracturing fluid may also include KCl as a clay stabilizer.

Enhanced Oil Recovery

The present invention may be employed with other techniques to further improve hydrocarbon recovery from subterranean formations. Initially, oil is produced from the fractured formation by pressure depletion (primary recovery). In this method, the differential pressure between the formation and a production well or wells forces the oil contained within the formation toward a production well where it can be recovered. Traditionally secondary recovery processes through injection of water or gas are used to displace additional oil toward producing wells. Typically, up to about 35 percent of the oil which is initially contained in a formation can be recovered in average through primary and secondary recovery. This leaves a large quantity of oil within the formation. Additionally, some formations contain oil which is too viscous to be efficiently recovered from the formation using primary and secondary processes.

Also, producing oil and gas wells have long been treated to stimulate production thereof utilizing a method termed "acidizing" in which an emulsion of an aqueous mineral acid either alone or in combination with various surfactants, corrosion inhibiting agents, and hydrocarbon oils is added to a producer well. Presumably, such treatments tend to remove deposits from the area of the subterranean oil or gas formation immediately adjacent to the production well bore, thus increasing the permeability of the formation and allowing residual oil or gas to be recovered through the well bore. Another object of such "acidizing" treatment of oil or gas producer wells is the removal of water from the interstices of the formation by the use of a composition which materially lowers the interfacial forces between the water and the oil or gas. Various surface-active agents have been recommended for this use.

Because of the need to recover a larger percentage of the oil from a formation, methods have been developed to recover oil which could not be recovered using only pressure depletion techniques. These methods are typically referred to as "enhanced oil recovery techniques" (EOR). The 35% global average recovery factor for conventional oil fields could be raised up to 50% through enhanced oil recovery.

Thus, the present invention is also directed to an EOR method for recovering crude oil from a subterranean formation, comprising introducing to the formation an aqueous medium comprising water or brine and the composition of the present invention described above.

The method of the invention is particularly useful in the stimulation of oil and gas wells which have failed to respond to acidizing treatment of the producing well including the use of various acids with various surfactants. The present invention may assist in maintaining stable viscosity at high temperatures downhole.

Methods of Use for Enhanced Oil Recovery

The aqueous medium utilized to form the solution of the invention can be soft water, brackish water, or brine. The aqueous fluid of the present invention comprising the stability polymer is introduced into the crude oil-bearing formation, typically by injecting the fluid having generally the viscosity of the oil-bearing formation of the oil well to be treated into the formation.

The stability polymer selected from at least one member of the group consisting of:
- a copolymer as described above having a weight average molecular weight of greater than or equal to about 30,000 grams per mole,
- a blend as described above of a first polymer and a second polymer,
- a crosslinked alkali swellable acrylate copolymer as described above, and
- at least one polymerizable reactive alkoxylated acrylate monomer as described above.

Optionally, after injection of the aqueous fluid comprising the present invention and, various hydrocarbon solvents may be employed to displace the aqueous solution out into the reservoir. Such hydrocarbon solvents as the low molecular weight, generally liquid hydrocarbons boiling below the gasoline range, such as the lower alkanes including butane, propane, pentane, hexane and heptane, as well as natural gasoline, petroleum naphtha and kerosene or mixtures of these hydrocarbons, are useful. Both sweet and sour crude oil is useful as a hydrocarbon to displace the aqueous solution out into the subterranean reservoir of oil or gas.

Optionally, injection of a preflush fluid may be utilized prior to injection of the aqueous fluid of the present invention. The preflush may consist of a hydrocarbon fluid, a brine solution, or simply water.

Also, injection of the aqueous fluid comprising the present invention may optionally be followed by an injection of a surfactant, a mobility control fluid or a polymeric flush, which is typically a polymer-thickened aqueous solution, into the formation to further enhance oil recovery. (If desired the stability polymer of the present invention can be in this injection of a surfactant, a mobility control fluid or a polymeric flush and this embodiment of the present invention is discussed below under the heading Chemical Flooding). The polymeric solution is utilized to drive or push the now oil bearing surfactant flood out of the reservoir, thereby "sweeping" crude oil out of the reservoir. Further, the polymeric solution has a very high viscosity which helps to prevent what is referred to in the industry as channeling or "fingering", thus improving sweep efficiency.

This polymeric flush or mobility control fluid may once again be followed by a water flush which may be brine or saline or softened water, or fresh water.

Oil is recovered at a production well spaced apart from the injection well as the drive fluid pushes the mobility buffer slug which sweeps the oil out of the pores in the formation and to the production well. Once the water/oil emulsion reaches the surface, it is put into holding tanks where it is subsequently demulsified, thereby allowing the oil to separate from the water through the natural forces of gravity.

For example, a hydrocarbon recovery composition including the present invention may be added to a portion of hydrocarbon containing formation that may have an average temperature of less than 80° C. To facilitate delivery of an amount of the hydrocarbon recovery composition to the hydrocarbon containing formation, the hydrocarbon composition may be combined with water or brine to produce an injectable fluid. Typically about 0.01 to about 5 wt % of the stability polymer, based on the total weight of injectable fluid, may be injected into the hydrocarbon containing formation through an injection well.

In certain embodiments, the concentration of the hydrocarbon recovery composition injected through the injection well may be about 0.05% to about 3 wt. %, based on the total weight of injectable fluid. In some embodiments, the concentration of the hydrocarbon recovery composition may be about 0.1% to about 1 wt. % based on the total weight of injectable fluid.

In some embodiments, a hydrocarbon recovery composition may be added to a portion of a hydrocarbon containing formation.

Chemical Flooding

As mentioned above, the stability polymer of the present invention can be used in chemical flooding. Chemical flooding is a promising enhanced oil recovery method which generally covers the use of polymer and/or surfactant slugs.

In polymer flooding, a polymer solution is injected to displace oil toward producing wells. The polymer solution is designed to develop a favorable mobility ratio between the injected polymer solution and the oil/water bank being displaced ahead of the polymer. However, the use of polymer is not always satisfactory as many polymer solutions are sensitive to brine type and concentration which can affect the apparent viscosity of the solution. In surfactant flooding, an aqueous solution containing surfactant is injected into the oil rich formation. Residual oil drops are deformed as a result of low Interfacial Tension provided by surfactant solution and drops are displaced through the pore throats and displaced oil is the recovered. See U.S. Pat. No. 7,789,160 to Hough et al. incorporated herein by reference in its entirety.

The present compositions advantageously are compatible with anionic surfactants typically used to decrease interfacial tension to also assist in enhancing oil recovery from subterranean formations.

The present invention improves enhanced oil recovery. For example, the present invention is also directed to a method for recovering crude oil from a subterranean formation, comprising introducing to the formation an aqueous medium comprising water or brine and the composition of the present invention including a combination of polyanionic polymer and polycationic polymer described above.

There are two primary components to EOR: improving displacement efficiency and improving macroscopic sweep efficiency. The present invention enhances oil recovery by maintaining stable viscosity at high temperatures.

The present compositions advantageously are compatible with anionic surfactants typically used to decrease interfacial tension to also assist in enhancing oil recovery from subterranean formations.

The aqueous medium of the composition may be soft water, brackish water or brine. Typically the aqueous medium in compositions used to treat subterranean formations comprises brine.

Typically a method for enhancing oil recovery includes the step of providing a subsurface reservoir containing hydrocarbons therewithin. A wellbore is provided in fluid communication with the subsurface reservoir. A surfactant-polymer solution is formed for injection into the reservoir. The surfactant-polymer solution is formed by mixing a composition with at least one surfactant, at least one polymer, and at least one co-solvent or co-surfactant such that the surfactant-polymer solution is clear and aqueous stable. The surfactant-polymer solution is injected through the wellbore into the reservoir. A chaser solution is formed for injection into the reservoir. The chaser solution has an additional predetermined quantity of the co-solvent or co-surfactant. The chaser solution is injected through the injection wellbore into the reservoir to increase the production of hydrocarbons from the reservoir while maintaining the clear and aqueous stability of the surfactant-polymer solution.

Other Ingredients

It should be also understood the compositions of the invention may contain components in addition to water, water soluble polymer, and surfactants. Such additional components are, for example, co-solvents, acids, bases, buffers, chelating agents for the control of multivalent cations, freezing point depressants, etc.

For example, a hydrocarbon recovery composition including water, water soluble polymer, and at least one member of the group of nonionic surfactants according to the present invention may be provided to the hydrocarbon containing formation alone or with other compounds for enhancing oil recovery. For example, these other compounds may be other nonionic additives (e.g., alcohols, ethoxylated alcohols and/or sugar based esters). Some embodiments have less than 0.3 weight percent of one or more anionic surfactants (e.g. sulfates, sulfonates, ethoxylated sulfates, and/or phosphates). In some embodiments the composition has less than 0.3 wt % each of anionic surfactant, amphoteric surfactant and zwitterionic surfactant. If desired, there may be an absence of anionic surfactant, an absence of amphoteric surfactant, and an absence of zwitterionic surfactant.

Alcohol

Alcohol can be used as mutual solvent to reduce water saturation. The interfacial tension between oil and ethanol is much lower than between oil and brine.

Capillary forces of retention for the alcohol are much reduced compared to those for brine.

It has been reported that isopropyl or butyl alcohol plus methyl alcohol could be used in miscible displacement to increase oil recovery of naphtha and mineral oil.

Others have investigated enhanced oil recovery by alcohol flooding. Their process design was strongly guided by the ternary phase of alcohol/oil/brine. They showed that oil recovery was highly dependent on the choice of alcohol/oil/brine combinations. Others have reported that injection of appropriate combinations of oil-soluble and water-soluble solvents such as alcohols and ketones could significantly enhance oil recovery.

In an embodiment, an aliphatic nonionic additive may be used in a hydrocarbon recovery composition. As used herein, the term "aliphatic" refers to a straight or branched chain of carbon and hydrogen atoms. In some embodiments, an aliphatic portion of an aliphatic nonionic additive may have an average carbon number from 10 to 24. In some embodiments, an aliphatic portion of an aliphatic nonionic additive may have an average carbon number from 12 to 18. In some embodiments, the aliphatic nonionic additive may include a branched aliphatic portion. A branched aliphatic portion of an aliphatic nonionic additive may have an average carbon number from 16 to 17. In some embodiments, a branched aliphatic group of an aliphatic nonionic additive may have less than about 0.5 percent aliphatic quaternary carbon atoms. In an embodiment, an average number of branches per aliphatic nonionic additive ranges from about 0.1 to about 2.5. In other embodiments, an average number of branches per aliphatic nonionic additive ranges from about 0.7 to about 2.5.

Methyl branches may represent between about 20 percent to about 99 percent of the total number of branches present in the branched nonionic additive. In some embodiments, methyl branches may represent greater than about 50 percent of the total number of branches in a branched nonionic additive. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

In an embodiment, an aliphatic nonionic additive may be a long chain aliphatic alcohol. The term "long chain," as used herein, refers to a carbon chain having an average carbon number from 10 to 30. A long chain aliphatic alcohol (e.g., a long chain primary alcohol) may be purchased commercially (e.g., NEODOL alcohols manufactured by Shell Chemical Co., Houston, Tex.). In certain embodiments, a long chain aliphatic alcohol may be prepared by a variety of generally known methods. A long chain aliphatic alcohol may have an average carbon number from 10 to 24. In some embodiments, a long chain aliphatic alcohol may have an average carbon number from 12 to 18. In other embodiments, a long chain aliphatic alcohol may have an average carbon number from 16 to 17.

In an embodiment, a portion of the long chain aliphatic alcohol may be branched. In some embodiments, branches of a branched aliphatic group of a long chain aliphatic alcohol may have less than about 0.5 percent aliphatic quaternary carbon atoms. In an embodiment, an average number of branches per long chain aliphatic alcohol ranges from about 0.1 to about 2.5. In other embodiments, an average number of branches per alcohol ranges from about 0.7 to about 2.5.

Methyl branches may represent between about 20 percent to about 99 percent of the total number of branches present in the branched long chain aliphatic alcohol. In some embodiments, methyl branches may represent greater than about 50 percent of the total number of branches in a branched long chain aliphatic alcohol. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

Aliphatic Anionic Surfactants

In an embodiment, an aliphatic anionic surfactant may be used in a hydrocarbon recovery composition. In certain embodiments, an aliphatic portion of an aliphatic anionic surfactant may have an average carbon number from 10 to 24. In some embodiments, an aliphatic portion of an aliphatic anionic surfactant may have an average carbon number from 12 to 18. In other embodiments, an aliphatic portion of an aliphatic anionic surfactant may have an average carbon number from 16 to 17. In some embodiments, the aliphatic anionic surfactant may include a branched aliphatic portion. In some embodiments, a branched aliphatic group of an aliphatic anionic surfactant may have less than about 0.5 percent aliphatic quaternary carbon atoms. In an embodiment, an average number of branches per aliphatic anionic surfactant ranges from about 0.1 to about 2.5. In other embodiments, an average number of branches per aliphatic anionic surfactant ranges from about 0.7 to about 2.5.

Methyl branches may represent between about 20 percent to about 99 percent of the total number of branches present in the branched anionic surfactant. In some embodiments, methyl branches may represent greater than about 50 percent of the total number of branches in a branched anionic surfactant. The number of ethyl branches in the alcohol may represent, in certain embodiments, less than about 30 percent of the total number of branches. In other embodiments, the number of ethyl branches, if present, may be between about 0.1 percent and about 2 percent of the total number of branches. Branches other than methyl or ethyl, if present, may be less than about 10 percent of the total number of branches. In some embodiments, less than about 0.5 percent of the total number of branches are neither ethyl nor methyl groups.

In an embodiment which further employs aliphatic anionic surfactant, a solution may provided which contains an effective amount of an aliphatic anionic surfactant selected from the group of compounds having the general formula: $R_1O(C_3H_6O)_m(C_2H_4O)_nYX$ wherein $R_1$ is a linear or branched alkyl radical, an alkenyl radical, or an alkyl or alkenyl substituted benzene radical, the non-aromatic portion of the radical containing from 6 to 24 carbon atoms; m has an average value of from 1 to 10; n has an average value of from 1 to 10; Y is a hydrophilic group; and X is a cation, preferably monovalent, for example N, K, $NH_4^+$. Y is a suitable hydrophilic group or substituted hydrophilic group such as, for example, the sulfate, sulfonate, phosphonate, phosphate or carboxylate radical. Preferably, $R_1$ is a branched alkyl radical having at least two branching groups and Y is a sulfonate or phosphate group.

Other Optional Additives for Enhanced Oil Recovery

The aqueous fluid of the present invention for injection into subterranean oil and/or gas formations may, optionally, further comprise clay stabilization or sand stabilization material. During oil recovery processes, sands and other materials may become entrained in the recovered oil. This may be mitigated by the addition of a clay stabilization or sand stabilization material. Suitable clay stabilization or sand stabilization materials include epoxy resins, polyfunctional cationic polymers, such as poly(N-acrylamidomethyltnmethyl ammonium chloride) or poly(vinylbenzyltrimethyl ammonium chloride).

Other optional ingredients that may be added to the aqueous fluid of the present invention include, but are not limited to polymers such as biopolysaccharides, cellulose ethers, acrylamide-derived polymers, corrosion inhibitors, oxygen scavengers, bactericides, and so forth, and any combination thereof.

The aqueous fluid of the present invention is introduced into the crude oil-bearing formation, typically by injecting the fluid into the formation. The aqueous fluid may be used in secondary or tertiary oil recovery processes, although the use of such fluids in other applications is not excluded.

Home Care of Industrial Care Compositions

In one embodiment, the present invention is directed to a home care or industrial cleaning composition, such as a liquid detergent, a laundry detergent, a hard surface cleanser, a dish wash liquid, or a toilet bowl cleaner, comprising water, one or more surfactants, and a polymer of the present invention. Suitable surfactants include those described above in regard to the personal care composition embodiments of the present invention. Such cleaning compositions may optionally further comprise one or more of water miscible organic solvents, such as alcohols and glycols, and/or one or more additives.

Suitable additives are known in the art and include, for example, organic builders, such as organophosphonates, inorganic builders, such as ammonium polyphosphates, alkali metal pyrophosphates, zeolites, silicates, alkali metal borates, and alkali metal carbonates, bleaching agents, such as perborates, percarbonates, and hypochlorates, sequestering agents and anti-scale agents, such as citric acid and ethylenediaminetetraacetic acid, inorganic acids, such as phosphoric acid and hydrochloric acid, organic acids, such as acetic acid, abrasives, such as silica or calcium carbonate, antibacterial agents or disinfectants, such as triclosan and cationic biocides, for example (N-alkyl)benzyldimethylammonium chlorides, fungicides, enzymes, opacifing agents, pH modifiers, dyes, fragrances, and preservatives.

In an embodiment the home care or industrial cleaner benefit agent is selected from the group consisting of soil release agents, binders, builders, fabric softeners, bleach and fragrances.

In an embodiment the home care or industrial cleaning composition for cleaning fabrics or hard surfaces comprising, the composition of the present invention and a surfactant and a home care or industrial cleaner benefit agent, for example soil release agents, binders, builders, fabric softeners, bleach and fragrances.

In an embodiment the composition is a detergent composition and comprises: the polymer, at least one detersive surfactant, and a builder.

The invention also encompasses a method for cleaning a substrate selected from the group consisting of a hard surface and a fabric, comprising applying the composition of the present invention to the substrate.

EXAMPLES

Example 1

Effect upon Freeze-Thaw Stability of Varying the Concentration of a Surfactant Composition Containing Sodium Trideceth Sulfate in Structured Surfactant Liquid formulations Surfactant Blend 1, an aqueous blend comprising sodium trideceth sulfate, cocamide MEA and sodium lauroamphoacetate was employed.

The formulations of Surfactant Blend 1 were made using the following procedure:

The initial blend contains 46.6 wt. % active surfactants in water. First, it was diluted with water to get the concentration needed;

Then the pH has to be adjusted to 5-5.5 by addition of a 50% Citric Acid solution. This is the batch from which all the formulations will be made;

A series of ten formulations was made by adding increments of 0.5% NaCl from 0.5% to 5% w/w of NaCl to the batch;

After the addition of NaCl, the formulation was mixed for 45 minutes to make sure the NaCl is dissolved. All the formulations made in this study had been mixed for 45 minutes after the addition of NaCl for consistency.

The viscosity of each sample was measured using a Brookfield viscometer with a RV4 spindle at a speed of 100 rpm for 5 and 10 wt. % Active Surfactant Blend 1; with a RV4 spindle at a speed of 50 rpm for 12.5 and 15% Active Surfactant Blend 1; and with a RV4 spindle at a variety of speeds for 20 and 25% Active Surfactant Blend 1. Measured viscosities are listed in TABLE 1A, 1B and 1C for 15, 20 and 25% Active Surfactant Blend 1.

To study the effect of the concentration of Active Surfactant Blend 1 upon freeze-thaw stability, different levels of active have been analyzed: 5% wt., 10 wt. %, 12.5 wt. %, 15 wt. %, 20 wt. % and 25 wt. % active surfactants based on total composition weight. Only the results obtained for the 12.5 wt. through 25 wt. % of active surfactants were recorded, because the MLV (multilamellar vesicles) phase does not exist below a critical concentration of about 10 wt. % surfactant.

TABLE 1 lists the physical description of the Active Surfactant Blend 1 and NaCl formulations.

TABLE 1

Physical Description of Active Surfactant Blend 1 + NaCl Formulations (% is wt. % total composition)

| % Active Surfactant Blend 1 | Before Freeze-Thaw Cycle | After 3 Freeze-Thaw Cycles |
|---|---|---|
| 5% | Unstable | Unstable. All the formulations were phases separated. |
| 10% | Opaque. Appeared structured | 0.5% to 3% NaCl: Unstable, Phases separation. 3.5% to 5% NaCl: Remained stable. |
| 12.5% | Opaque. Appeared structured. | 0.5% to 3% NaCl: Unstable, Phases separation. 3.5% to 5% NaCl: Remained stable. |
| 15% | Opaque. Appeared structured. | 0.5% to 2% NaCl: Unstable, Phases separation. 2.5% to 5%: Remained stable. |
| 20% | Opaque. Appeared structured. | 0.5% to 1.5% NaCl: Unstable, Phases separation. 2% to 5% NaCl: Remained stable. |
| 25% | Opaque. Appeared structured. | 0.5% NaCl: 2 phases. 1% to 4.5% NaCl: Remained structured. 5% NaCl: Phase separated. |

Measured viscosities are listed in TABLE 1A, 1B and 1C for 15, and 25% Active Surfactant Blend 1.

TABLE 1A

15% Active Surfactant Blend 1 + NaCl Viscosity (Brookfield Viscometer Spindle RV4, Speed 50 RPM)

| Description (% NaCl w/w) | Before Freeze-Thaw Cycle Viscosity (cP) | After 3 freeze-Thaw Cycles Viscosity (cP) |
|---|---|---|
| 0.5 | Out of range | — |
| 1 | Out of range | — |
| 1.5 | Out of range | — |
| 2 | 444 | — |
| 2.5 | 424 | 400 |
| 3 | 476 | 452 |
| 3.5 | 496 | 492 |
| 4 | Out of range | Out of range |
| 4.5 | Out of range | Out of range |
| 5 | Out of range | Out of range |

Note: The viscosity values out of the range for the spindle and speed combination chosen were too low. The appearance of the formulations before freeze-thaw cycle had not been recorded.

TABLE 1B

Active Surfactant Blend 1: 20% Active Surfactants + NaCl Appearance and Viscosity; Brookfield Viscometer RV4 Spindle

| Description (% NaCl w/w) | Before Freeze-Thaw Cycle Viscosity (cP) | Spindle Speed (RPM) | After 3 Freeze Thaw Cycles Viscosity (cP) | Speed (RPM) |
|---|---|---|---|---|
| 0.5 | Out of range | 50 | — | — |
| 1 | 412 | 50 | — | — |
| 1.5 | 554 | 50 | — | — |
| 2 | 832 | 50 | Out of range | 10 |
| 2.5 | 1188 | 50 | 2540 | 10 |
| 3 | 2220 | 10 | 3180 | 10 |
| 3.5 | Out of range | 50 | 3200 | 10 |
| 4 | Out of range | 100 | 3000 | 10 |
| 4.5 | Out of range | 100 | Out of range | 10 |
| 5 | Out of range | 100 | Out of range | 20 |

Note: The viscosity values out of the range for the spindle and speed combination chosen were too low.

TABLE 1C

25% Active Surfactant Blend 1 + NaCl Viscosity (Brookfield Viscometer Spindle RV4, Speed 50 RPM)

| Description (% NaCl w/w) | Before Freeze-Thaw Cycle Viscosity (cP) | After 3 freeze-Thaw Cycles Viscosity (cP) |
|---|---|---|
| 0.5 | 588 | — |
| 1 | 970 | 662 |
| 1.5 | 1834 | 1300 |
| 2 | 2740 | 2244 |
| 2.5 | 2804 | 2536 |
| 3 | 3024 | 2800 |
| 3.5 | 2722 | 2734 |
| 4 | 2448 | 2882 |
| 4.5 | 1672 | 3508 |
| 5 | 784 | — |

The electrolyte appeared to help stabilize the structured surfactants liquids formulations.

Example 2

Comparison of the Effects of Yield Providing and Non-Yield Providing Polymers on Freeze-Thaw Stability The following compares the effects of yield providing and non-yield providing polymers on Freeze-Thaw stability. Yield providing polymers increase the viscosity and provide yield to the formulation. Non-yield providing polymers also have a thickening effect but they do not provide yield.

The synthetic polymers used were the following:
RHODIA HASE Polymer A and RHODIA HASE Polymer B;
HASE polymers (from Rohm and Haas): ACULYN 22 and ACULYN 28 linear HASE polymer emulsions;
ASE polymer (From LUBRIZOL): CARBOPOL SF-1.
RHODIA HASE Polymer A and RHODIA HASE Polymer B were composed of two different types of specialty hydrophobic macro monomers, which are Macro Monomer I and Macro Monomer II. RHODIA HASE Polymer A was composed of 4% w/w of Macro Monomer 1 and 6% w/w of Macro Monomer II. RHODIA HASE Polymer B was composed of 10% w/w of each of these polymers. The only parameter that differentiates these two polymers is the amount of hydrophobic macro monomers.

Macro Monomer I was a monomer made from NOPOL alcohol ("NOPOL polyether monomer"). The general family of these monomers is represented in Formula A.XXX (which repeats above-presented Formula A.XIII):

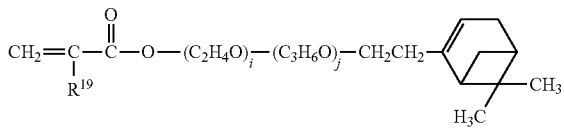

A.XXX wherein i, j, and $R^{19}$ are each as described above. Typically i and j are 1 to 200, for example 5 to 30. More typically, i is an integer of from 10 to 40, and even more typically from 15 to about 30, and j is an integer of from 1 to 20, and even more typically from about 2 to about 10.

Macro Monomer II was made from a mixture of C22, C16 and C18 linear alkyl chains ("$(C_{16}$-$C_{22})$alkyl-polyether monomer"). It was a branched macro monomer.

The general family of this embodiment of Macro Monomer II is represented by structure A.XXXI (which repeats above-presented Formula XX):

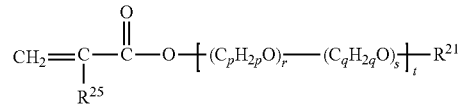

(A.XXXI)

wherein
$R^{21}$ is linear or branched $(C_5$-$C_{50})$alkyl, hydroxyalkyl, alkoxyalkyl, aryl, or aralkyl,
$R^{25}$ is methyl or ethyl, and
p, q, r, s, and t are each as described above. For example:
wherein:
p and q are independently integers of from 2 to 5, more typically 2 or 3,
each r is independently an integer of from 1 to about 80, more typically from 1 to about 50,
each s is independently an integer of from 0 to about 80, more typically from 0 to about 50,
t is an integer of from 1 to about 50, provided that the product obtained by multiplying the integer t times the sum of r+s is from 2 to about 100.

An idealized structural formula for RHODIA HASE Polymers A and B is shown by structural formula A.XXXII. As mentioned above, RHODIA HASE Polymer A was composed of 4% w/w of Macro Monomer 1 and 6% w/w of Macro Monomer II. RHODIA HASE Polymer B was composed of 10% w/w of each of these polymers. The only parameter that differentiates these two polymers is the amount of hydrophobic macro monomers.

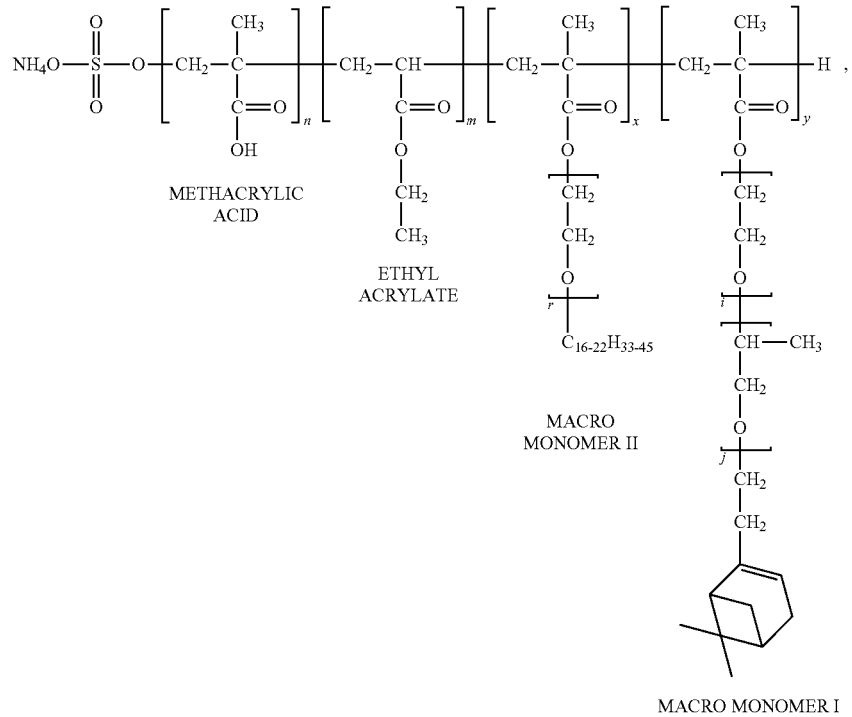

A.XXXII

RHODIA HASE Polymers A, B

In general for Formula A.XXXII for HASE Polymer A and B parameters n, m, x and y are sufficient to obtain the desired molecular weight; parameter r is an integer from 1 to about 80, more typically an integer from 1 to about 50; parameters i and j are independently from 1 to 200, typically 5 to 30. More typically, i is an integer of from 10 to 40, and even more typically from 15 to about 30, and j is an integer of from 1 to 20, and even more typically from about 2 to about 10.

The HASE Polymers A and B contained:

first monomeric units derived from a monomeric compound according to structure (A.XXX) above, wherein $R^{19}$=methyl, i=25, and j=5 ("NOPOL polyether monomer, Macro monomer I"), second monomeric units derived from a mixture of ($C_{16}$-$C_{22}$)alkyl-polyethoxylated methacrylates having an average of 25 ethylene oxide units per molecule, according to structure (A.XXXI), wherein $R^{25}$ is methyl, $R^{21}$ is a mixture of linear $C_{16}$ alkyl, linear $C_{18}$ alkyl, and linear $C_{22}$ alkyl groups, p=2, r=25, s=0, and t=1 ("($C_{16}$-$C_{22}$)alkyl-polyether monomer, Macro monomer II"), third monomeric units derived from methacrylic acid ("MAA"), and fourth monomeric units derived from ethyl acrylate ("EA").

Although not part of this Example, if desired a HASE Polymer X comprising Macro Monomer I but not Macro Monomer II could have been blended with a HASE Polymer Y comprising Macro Monomer II but not Macro Monomer I. An idealized structural formula of HASE Polymer X is shown by structural formula A.XXXIII, wherein y and z are independently from 1 to 200, typically 5 to 30. More typically, y is an integer of from 10 to 40, and even more typically from 15 to about 30, and z is an integer of from 1 to 20, and even more typically from about 2 to about 10. Parameters n, m and x are sufficient to achieve the desired molecular weight.

HASE Polymer Y would be the same as HASE Polymer X but substitute Macro Monomer II of formula A.XXXII for Macro Monomer I.

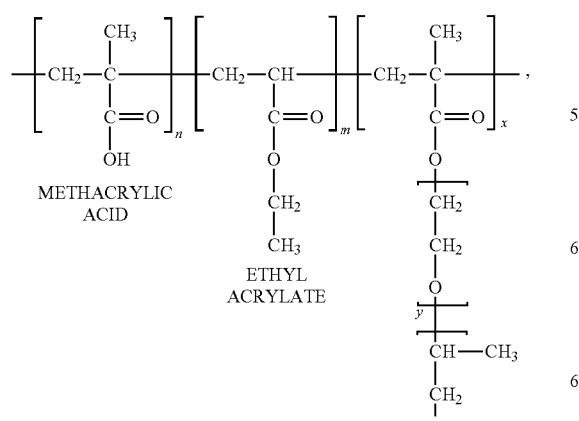

A.XXXIII

METHACRYLIC ACID

ETHYL ACRYLATE

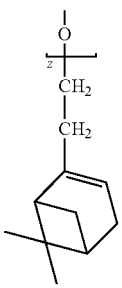

MACRO MONOMER I

RHODIA HASE Polymer X

HASE Polymers A and B were synthesized by emulsion polymerization using conventional radical polymerization. They contain methacrylic acids which contains carboxylic groups which make the polymer anionic.

Likewise, if HASE Polymer X or Y is added, it could be synthesized by emulsion polymerization using conventional radical polymerization.

ACULYN 22 is a linear anionic hydrophobically modified alkali-soluble acrylic polymer emulsion (HASE). The general structure of ACULYN 22 is shown on the Formula A.XXXIV, wherein Rx is an acyl chain from 1 to 18 carbons. It has a high aqueous thickening and stabilizing efficiency.

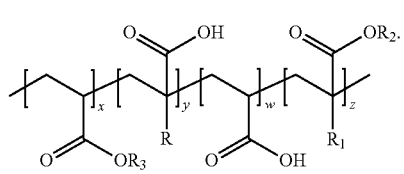

A.XXXIV

The general structure of the ACULYN 28 is shown on the Formula A.XXXV below, wherein Rx is an acyl chain from 1 to 22 carbons.

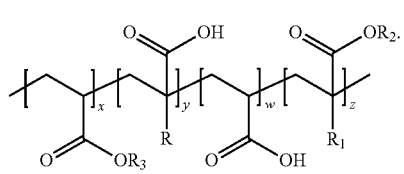

A.XXXV

CARBOPOL AQUA SF-1 polymer is an Alkali-Swellable Acrylic Emulsion polymer. As supplied, the majority of the polymer's carboxyl functionality is in the protonated form; the polymer molecules are coiled and bring relatively little suspension and viscosity to the liquid. Upon neutralization, the molecules ionize and expand due to the charge repulsion of the anionic carboxylate. Thus they provide suspending and thickening properties to the aqueous system in which they reside. This mechanism is known as "hydrodynamic thickening". In this theory, it is the physical packing of polymer molecules that is responsible for the development of suspending ability and viscosity. Thus this "space-filling" mechanism is distinctly different from the associative thickening mechanism attributed to HASE polymers.

The natural polymers used were the following:
RHODICARE T Xanthan Gum;
JAGUAR S Guar Gum;
JAGUAR HP105 Hydroxypropylguar.

The formulations with the synthetic polymers were made as follows:
The amount of water needed was added in the beaker;
1% of the polymer was added to the water and the agitation was started;
The amount of Surfactant Blend 1 needed to reach the desired concentration was then added;
The pH was adjusted to 5-5.5 by addition of a 50% Citric Acid solution;
The amount of NaCl needed to reach the desired concentration was added;
The formulation was then mixed for 45 min.

The RHODICARE T formulation was made following the general process detailed for the synthetic polymers.

The JAGUAR HP 105 Hydroxypropylguar formulation was made as follows: Jaguar HP 105 Hydroxypropylguar was dispersed in water; This blend was mixed for 20 min to ensure complete hydration of the polymer; The Surfactant Blend A was then added and the pH was adjusted to 5-5.5 using a 50% Citric Acid solution; The NaCl needed was added and the formulation was then mixed for 45 min.

JAGUAR S guar gum was dispersed by hand in the Surfactant Blend A before being added to the water while mixing (at an average speed of 200-250 RPM). The pH of the formulations was then adjusted, the NaCl was added and the formulation was mixed for 45 min.

The results of this example were obtained with formulations containing:
15% of Surfactant Blend 1;
1% of polymer;
2% of NaCl.

The results obtained are listed in TABLE 2. Certain formulations (with ACULYN 28 and JAGUAR S) have been done with 3 wt. % of NaCl because they were already unstable at room temperature with only 2 wt. % of NaCl. Viscosity shown in TABLE 2 was measured using a Brookfield RV4 spindle at a speed of 50 rpm except for the sample of 1% ACULYN 22+15% Surfactant Blend 1+2% NaCl. The sample of 1% ACULYN 22+15% Surfactant Blend 1+2% NaCl was measured using a Brookfield RV4 spindle at a speed of 30 rpm.

TABLE 2

| (wt. % total composition) | Before Freeze-Thaw Cycle | | After 3 Freeze-Thaw Cycles | |
|---|---|---|---|---|
| | Appearance | Viscosity (cP) | Appearance | Viscosity (cP) |
| 1% RHODICARE T + 15% Surfactant Blend 1 + 2% NaCl | structured | 1406 | Phase separated | Not measured |
| 1% JAGUAR HP 105 + 15% Surfactant Blend 1 + 2% NaCl | structured | 1438 | Phase separated | Not measured |
| 1% JAGUAR S + 15% Surfactant Blend 1 + 2% NaCl | Phase separated | — | — | — |
| 1% JAGUAR S + 15% Surfactant Blend 1 + 3% NaCl | Structured | 2362 | Structured | 3058 |
| 1% CARBOPOL SF-1 + 15% Surfactant Blend 1 + 2% NaCl | Structured | 3128 | structured | 2068 |

TABLE 2-continued

| (wt. % total composition) | Before Freeze-Thaw Cycle | | After 3 Freeze-Thaw Cycles | |
|---|---|---|---|---|
| | Appearance | Viscosity (cP) | Appearance | Viscosity (cP) |
| 1% ACULYN 22 + 15% Surfactant Blend 1 + 2% NaCl | Structured | 4736 | Structured | 4140 |
| 1% ACULYN 28 + 15% Surfactant Blend 1 + 2% NaCl | Phase separated | — | Phase separated | — |
| 1% ACULYN 28 + 15% Surfactant Blend 1 + 3% NaCl | Structured | 1610 | Structured | 1340 |
| 1% RHODIA HASE Polymer A + 15% Surfactant Blend 1 + 2% NaCl | Structured | 2898 | Structured | 2462 |
| 1% RHODIA HASE Polymer B + 15% Surfactant Blend 1 + 2% NaCl | Structured | 2102 | Structured | 1036 |

All the formulations containing a synthetic yield providing polymer remained stable whereas the formulation with RHODICARE T Xanthan Gum, which also provides yield, failed the freeze-thaw test.

The salt concentration in the ACULYN 28 formulation had to be increased for it to remain stable. The formulations with RHODICARE T Xanthan Gum and JAGUAR HP 105 did not remain stable with 2 wt. NaCl.

Example 3

Influence of the Variation of the Level of Salt, Used with the Same Percentage of Surfactant Blend 1 and RHODIA HASE Polymer A concentration of 2 wt. % NaCl was chosen for all the formulations. 2 wt. % NaCl was the salt level leading to the optimum viscosity for these three active levels of Surfactant Blend 1 (without the addition of polymer).

To test the effect of the addition of polymer compositions of 10 weight % Surfactant Blend 1 and 1 weight % Rhodia HASE Polymer A were made according the procedure described above but the levels of NaCl were varied.

As shown in the salt curve of FIG. 3, before freeze-thaw cycle, the optimum viscosity was reached for a concentration of NaCl between 1.5% and 2%. After freeze-thaw cycle, the 1.5% and 2% NaCl formulations were at the limit of their stability, i.e. they were just a little bit patchy, but they were not phases separated. From 2.5% to 5% NaCl, the formulations remained stable. Therefore 2.5% NaCl appeared to be a preferred salt level for these 10 weight % Surfactant Blend 1 formulations.

Example 4

Influence of the Variation of the Active Level of Surfactant Blend 1, Used with the Same Percentage of RHODIA HASE Polymer The formulations with the HASE Polymer A and RHODIA HASE Polymer B were made for three different active levels of Surfactant Blend 1: 10%, 12.5% and 15%. The results obtained for this study are recorded in the TABLE 3.

TABLE 3

Viscosity Results - RHODIA HASE polymers, viscosity measured using a Brrokfield viscometer with a RV4 Spindle at 50 rpm

|  |  | Before Freeze-Thaw Cycle | | After 3 Freeze-Thaw Cycles | |
|---|---|---|---|---|---|
|  |  | Appearance | Viscosity (cP) | Appearance | Viscosity (cP) |
| Surfactant Blend 1 10% Active + 2% NaCl | No polymer | Structured | Out of range | Phase separated | — |
|  | +1% RHODIA HASE Polymer A | Structured | 1564 | Structured | 1522 |
|  | +1% RHODIA HASE Polymer B | Structured | 1106 | Structured | 834 |
| Surfactant Blend 1 12.5% Active + 2% NaCl | No polymer | Structured | Out of range | Phase separated | — |
|  | +1% RHODIA HASE Polymer A | Structured | 2494 | Structured | 2442 |
|  | +1% RHODIA HASE Polymer B | Structured | 1542 | Structured | 1334 |
| Surfactant Blend 1 15% Active + 2% NaCl | No polymer | Structured | 444 | Phase separated | — |
|  | +1% RHODIA HASE Polymer A | Structured | 2898 | Structured | 2462 |
|  | +1% RHODIA HASE Polymer B | Structured | 2102 | Structured | 1036 |

Note:
The viscosity values out of the range for the spindle and speed combination chosen were too low.

TABLE 3 showed all the formulations containing 1% of RHODIA HASE polymer remained stable after three freeze-thaw cycles. In previous studies, it has been observed that formulations with a low active level (i.e., 10%, 12.5% and 15%) remained stable after three freeze-thaw cycles only if the concentration of NaCl was high (i.e., higher than 2% in the three cases).

This showed addition of a small quantity of HASE polymer brings freeze-thaw stability to the structured surfactants liquids formulations at a lower salt level.

Example 5

Influence of Different Concentrations of RHODIA HASE Polymer, Used with 10 Wt. % Active Surfactant Level of Surfactant Blend 1

As indicated by the above data addition of RHODIA HASE polymers improves the stability through freeze-thaw cycle of 10 wt. % active Surfactant Blend 1 formulations.

This example compares the effect on freeze-thaw stability of changing concentration from 1 wt. % concentration of RHODIA HASE polymer with 0.5 wt % concentration of RHODIA HASE polymer. The previous formulations were made with 1 wt. % RHODIA HASE polymer, so the present example compares compositions with 1 wt. % of HASE polymer to compositions with 0.5% of HASE polymer. According to the salt curve plotted in FIG. 3, it was decided to use 2.5 wt. % NaCl with 0.5 wt. % HASE polymer. In contrast, the 1% RHODIA HASE formulations were made using 2 wt. % NaCl.

The results were recorded in the TABLE 4.

TABLE 4

Effect of the percentage of RHODIA HASE polymer, viscosity measured using a Brookfield viscometer with a RV4 Spindle

|  | Before Freeze-Thaw Cycle | | After 3 Freeze-Thaw Cycles | |
|---|---|---|---|---|
|  | Appearance | Viscosity (cP) | Appearance | Viscosity (cP) |
| 1% RHODIA HASE Polymer A + 2% NaCl | Structured | 1564 at 50 rpm | Structured | 1522 at 50 rpm |
| 0.5% RHODIA HASE Polymer A + 2.5% NaCl | Structured | 469 at 100 rpm | Structured | 353 at 100 rpm |
| 1% RHODIA HASE Polymer B + 2% NaCl | Structured | 1106 at 50 rpm | Structured | 834 at 50 rpm |
| 0.5% RHODIA HASE Polymer B + 2.5% NaCl | Structured | 362 at 100 rpm | Structured | 260 at 100 rpm |

TABLE 4 shows all the formulations remained stable after three freeze-thaw cycles. However, the viscosity of the formulations containing only 0.5% of HASE polymer is very low.

Example 10

Sodium Lauryl Sulfate+Cocamide MIPA+Sodium Lauroamphoacetate Formulations (Surfactant Blend 2)

Surfactant Blend 2 includes Sodium Lauryl Sulfate+Cocamide MIPA+Sodium Lauroamphoacetate. It was not as stable as Surfactant Blend 1 through freeze-thaw cycle. Thus, the effect of adding HASE polymer to Surfactant Blend 2 was tested.

Surfactant Blend 2 (SLS+MIPA+L-32) was made by hand as follows:

The water was added to the beaker and the agitation is started;

The MIRANOL ULTRA L-32 was then added and the blend is mixed until it becomes uniform;

Once the batch was uniform, the Inter SLS was added. Then the blend was mixed and heated to 65° C.;

In the meantime, the MIPA was put in a separate beaker and pre-melted.

It will therefore take less time to dissolve when it will be added to the blend. It was important to make sure the temperature of the MIPA does not exceed the one of the blend. If the MIPA is hotter than the blend, it will solidify when added to the batch;

The MIPA was added and the blend was mixed until it dissolves completely;

The heat was turned off and mixed until uniform;

Once the batch was at 40° C. or below, glydant was added and the blend is mixed until uniform.

The quantities of the different components added are given in TABLE 5. These could be body wash, hand wash, or shampoo formulations. MIPA is cocamide monoisopropanolamine, SLS is sodium lauryl sulfate, MIRANOL Ultra L-32 is sodium lauroamphoacetate. Glydant is a formaldehyde based preservative.

TABLE 5

Composition of the blend

| Ingredient | Target % Active in Blend | Wt (g) | Actual (g) |
|---|---|---|---|
| sodium lauryl amphoacetate | 8.52% | 412.5 | 413.36 |
| Cocamide MIPA | 5.35% | 84.525 | 84.84 |
| SLS | 19.00% | 925.35 | 936.50 |
| Glydant | — | 4.5 | 4.52 |
| Water | — | 73.125 | 73.13 |
| Total | 32.87% | 1500.00 | |

This blend was diluted to reach a concentration of 15 wt. % of active, and six formulations were made:
Three formulations containing 1% of RHODIA HASE Polymer A and respectively 0%, 2% and 3% of NaCl;
Three formulations containing 1% of RHODIA HASE Polymer B and respectively 0%, 2% and 3% of NaCl.
The results obtained are recorded in TABLES 6A and 6B.

TABLE 6A

Appearance and Viscosity of (SLS + Cocamide MIPA + MIRANOL ULTRA L-32) Formulations

| | | Before Freeze-Thaw Cycle | | After 3 Freeze-Thaw Cycles | |
|---|---|---|---|---|---|
| | | Appearance | Viscosity (cP) | Appearance | Viscosity (cP) |
| 1% RHODIA HASE Polymer A | +0% NaCl | Homogeneous* | 12330 (RV4 Spindle at 10 rpm) | Homogeneous* | 11700 (RV4 Spindle at 10 rpm) |
| | +2% NaCl | Structured | 10880 (RV4 Spindle at 10 rpm) | Structured | 9810 (RV4 Spindle at 10 rpm) |
| | +3% NaCl | Structured | 13380 (RV4 Spindle at 10 rpm) | Structured | 14570 (RV4 Spindle at 10 rpm) |
| 1% RHODIA HASE Polymer B | +0% NaCl | Homogeneous* | 2306 (RV4 Spindle at 50 rpm) | Homogeneous* | 2382 (RV4 Spindle at 50 rpm) |
| | +2% NaCl | Homogeneous* | 848 (RV4 Spindle at 50 rpm) | Homogeneous* | 840 (RV4 Spindle at 50 rpm) |
| | +3% NaCl | Phase separated | — | Phase separated | — |

*There is no phase separation but the formulation does not look structured. It looks different from the previously made structured samples.

TABLE 6B

Appearance and Viscosity of (SLS + Cocamide MIPA + MIRANOL ULTRA L-32) Formulations

| | | Before Freeze-Thaw Cycle | | After 3 Freeze-Thaw Cycles | |
|---|---|---|---|---|---|
| | | Appearance | Viscosity (cP) | Appearance | Viscosity (cP) |
| 0.5% RHODIA HASE Polymer A | +2% NaCl | Structured | 311 (RV3 Spindle at 100 rpm) | Structured | 279 (RV3 Spindle at 100 rpm) |
| 0.5% RHODIA HASE Polymer C | +2% NaCl | Structured | 202 (RV3 Spindle at 100 rpm) | Structured | 192 (RV3 Spindle at 100 rpm) |
| 1% RHODIA HASE Polymer C | +2% NaCl | Structured | 4565 (RV3 Spindle at 20 rpm) | Phase separated | 4535 (RV3 Spindle at 20 rpm) |
| 1% RHODIA HASE Polymer D | +2% NaCl | Structured | 10850 (RV3 Spindle at 10 rpm) | Structured | 10200 (RV3 Spindle at 10 rpm) |

RHODIA HASE Polymer A was composed of 4% w/w of Macro Monomer I and 6% w/w of Macro Monomer II.

RHODIA HASE Polymer B was composed of 10% w/w of each of these polymers.

RHODIA HASE Polymers C and D contain the following w/w ratio of hydrophobic Macro Monomers I and II: RHODIA HASE Polymer D: 4/6, same as RHODIA HASE Polymer A; RHODIA HASE Polymer C: 8/6.

TABLE 6 shows only one formulation which did not remain stable at all. It is the last formulation, containing 1% of RHODIA HASE Polymer B and 3% NaCl. For the other formulations, there was not any major difference in aspect and viscosity after three freeze-thaw cycles. Nevertheless, none of the salt-free formulations were structured. TABLE 6 shows RHODIA HASE Polymer A gave the most promising results. RHODIA HASE Polymer D also gave promising freeze-thaw stability to the formulation.

As a comparison TABLE 7 shows compositions with Sodium lauryl sulfate (SLS), cocamide MIPA and MIRANOL Ultra L-32 (sodium lauroamphoacetate) but without the RHODIA HASE Polymer.

TABLE 7 (SLS+Cocamide MIPA+MIRANOL ULTRA L-32): Salt Curve 15% Active Appearance and Viscosity Measured with a Brookfield Viscometer with an RV3 Spindle at 100 rpm.

TABLE 7

| Description | Before Freeze-Thaw Cycle | | After 3 freeze-Thaw Cycles | |
|---|---|---|---|---|
| (% NaCl w/w) | Appearance | Viscosity (cP) | Appearance | Viscosity (cP) |
| 0.5 | Homogeneous | 366 | Homogeneous | 363 |
| 1 | Homogeneous | 391 | Phase separation | 240 |
| 1.5 | Structured | 448 | Phase separation | 258 |
| 2 | Structured | 407 | Phase separation | — |
| 2.5 | Structured | 447 | Phase separation | — |
| 3 | Structured | 220 | Phase separation | — |
| 3.5 | Structured | Out of range | Phase separation | — |
| 4 | Structured | Out of range | Phase separation | — |
| 4.5 | Phase separation | Out of range | Phase separation | — |
| 5 | Phase separation | — | Phase separation | — |

Note:
The viscosity values out of the range for the spindle and speed combination chosen were too low.

Example A

HASE Polymer Synthesis

The following example illustrates the preparation and properties of the fluids and should not be construed to limit the scope of the invention, unless otherwise expressly indicated in the appended claims. All percentages, concentrations, ratios, parts, etc. are by weight unless otherwise noted or apparent from the context of their use.

As described above typical families of RHODIA HASE polymers include those of RHODIA HASE Polymers A, B, C and D composed of two different types of specialty hydrophobic macro monomers, which are Macro Monomer I and Macro Monomer II. An idealized structural formula for RHODIA HASE Polymers A, B, C and D is shown by above-mentioned structural formula A.XXXII.

Also described above were HASE Polymer X comprising Macro Monomer I but not Macro Monomer II and HASE Polymer Y comprising Macro Monomer II but not Macro Monomer I. An idealized structural formula of HASE Polymer X is shown by above-mentioned structural formula A.XXXIII.

Additional RHODIA HASE polymers containing Macro Monomers I and II were synthesized. The ingredients used to make these HASE Polymers are summarized in TABLE 8.

To make these additional RHODIA HASE polymers containing Macro Monomers I and II the NOPOL polyether monomer was introduced in the form of an aqueous emulsion ("NOPOL polyether monomer emulsion") that contained, based on 100 pbw of the emulsion, about 50 pbw of the NOPOL polyether monomer and about 25 pbw MAA. The $(C_{16}-C_{22})$alkyl-polyether monomer was introduced in the form of an aqueous emulsion ("$(C_{16}-C_{22})$alkyl-polyether emulsion") that contained, based on 100 pbw of the emulsion, about 50 pbw of the $(C_{16}-C_{22})$alkyl-polyether monomer and about 25 pbw MAA. TABLE 8 shows samples S1, S2 and S3 of compositions for making HASE Polymer comprising Macro Monomer I and Macro Monomer II.

TABLE 8

| | Charges (grams) | | |
|---|---|---|---|
| | Sample S1 | Sample S2 | Sample S3 |
| Kettle charge | | | |
| Water | 323.9 | 322.8 | 382.8 |
| RHODAPEX AB20 (sulfated alcohol ethoxylate, 29% solids content) | 2.07 | 5.17 | 2.07 |
| Monomer emulsion | | | |
| Water | 300.0 | 300.0 | 300.0 |
| RHODAPEX AB20 (sulfated alcohol ethoxylate, 29% solids content) | 20.7 | 51.7 | 20.7 |
| Ethyl Acrylate (EA) | 159.0 | 159.0 | 144.0 |
| Methacrylic acid (MAA) | 111.0 | 111.0 | 96.0 |
| NOPOL polyether monomer emulsion | 24.0 | 24.0 | 60.0 |
| $(C_{16}-C_{22})$ alkyl-polyether monomer emulsion | 36.0 | 36.0 | 60.0 |
| Initiator solution | | | |
| Ammonium persulfate | 0.84 | 0.84 | 0.42 |
| Water | 79.7 | 79.7 | 39.8 |
| Chaser solution | | | |
| Part 1: t-butylperoxybenzoate | 0.60 | 0.60 | 0.60 |
| Part 2: | | | |
| Water | 19.7 | 19.7 | 19.7 |
| Erythorbic acid | 0.30 | 0.30 | 0.30 |
| Total | 1077.8 | 1110.8 | 1126.4 |

The relative amounts of the monomeric units in the each of the respective polymers of Samples 51, S2 and S3 are given in TABLE 9A, as weight percent of total monomers charged and as mole percent of total monomers charged. The average particle size, as determined by light scattering, of each of the latex polymers of Synthesis Samples 51, S2, and S3 are also given in TABLE 9A.

TABLE 9A

| | Sample S1 | Sample S2 | Sample S3 |
|---|---|---|---|
| NOPOL polyether monomer | | | |
| wt % | 3.8 | 3.8 | 9.1 |
| mole % | 0.3 | 0.3 | 0.7 |
| $(C_{16}-C_{22})$ alkyl-polyether monomer | | | |
| wt % | 5.7 | 5.7 | 9.1 |
| mole % | 0.4 | 0.4 | 0.7 |
| MAA | | | |
| wt % | 40.00 | 40.00 | 38.2 |
| mole % | 47.6 | 47.6 | 49.8 |
| EA | | | |
| wt % | 50.5 | 50.5 | 43.6 |
| mole % | 51.7 | 51.7 | 48.9 |
| Average particle size (nm) | 103 | 71 | 94 |

Further additional samples of HASE polymers synthesized are as listed in TABLES 9B and 9C. Samples S4-S17 contain NOPOL polyether (Macro Monomer I) and $(C_{16}-C_{22})$ alkyl polyether (Macro Monomer II). Samples C1-C4 contain NOPOL polyether or $(C_{16}-C_{22})$ alkyl polyether. Some examples include polyethyleneglycol 400 dimethacrylate (PEG400DMA Li) or ethylene glycol dimethacrylate (EGDMA).

TABLE 9B

Samples with NOPOL polyether and (C16-C22) alkyl polyether

| Monomer | S4 | S5 | S6 | S7 | S8 | S9 | S10 | S11 | S12 |
|---|---|---|---|---|---|---|---|---|---|
| NOPOL polyether | 4.76 | 6.60 | 3.81 | 3.77 | 3.74 | 1.94 | 3.85 | 5.71 | 5.61 |
| ($C_{16}$-$C_{22}$) alkyl polyether | 4.76 | 4.72 | 5.71 | 7.55 | 9.35 | 3.88 | 3.85 | 3.81 | 7.48 |
| MAA | 40.00 | 39.79 | 40.00 | 39.79 | 39.58 | 40.43 | 40.21 | 40.00 | 39.58 |
| EA | 50.48 | 48.89 | 50.48 | 48.89 | 47.33 | 53.74 | 52.09 | 50.48 | 47.33 |
| EGDMA | — | — | — | — | — | — | — | — | — |
| PEG400DMA Li | — | — | — | — | — | — | — | — | — |

TABLE 9C

| | Samples with NOPOL polyether and ($C_{16}$-$C_{22}$) alkyl polyether | | | | | Samples with NOPOL polyether or ($C_{16}$-$C_{22}$) alkyl polyether | | | |
|---|---|---|---|---|---|---|---|---|---|
| Monomer | S13 | S14 | S15 | S16 | S17 | C1 | C2 | C3 | C4 |
| NOPOL polyether | 7.51 | 9.30 | 3.87 | 3.80 | 5.75 | 4.88 | 0 | 9.52 | 0.00 |
| ($C_{16}$-$C_{22}$) alkyl polyether | 4.69 | 4.65 | 1.94 | 5.71 | 1.92 | 0 | 4.88 | 0.00 | 9.52 |
| MAA | 39.69 | 39.48 | 40.31 | 39.94 | 40.10 | 41.46 | 41.46 | 40.00 | 40.00 |
| EA | 48.11 | 46.56 | 53.58 | 50.40 | 51.94 | 53.66 | 53.66 | 50.48 | 50.48 |
| EGDMA | — | — | 0.31 | — | — | — | — | — | — |
| PEG400DMA Li | — | — | — | 0.15 | 0.29 | — | — | — | — |

The spirit and scope of the present invention is not limited by the above-description, but is defined by the claims appended hereto.

What is claimed is:

1. A freeze thaw stable composition, comprising:

a continuous phase comprising:

a freeze thaw stability copolymer having a weight average molecular weight of greater than or equal to 30,000 grams per mole, water, and a surfactant, wherein the copolymer has the formula A.XXXII:

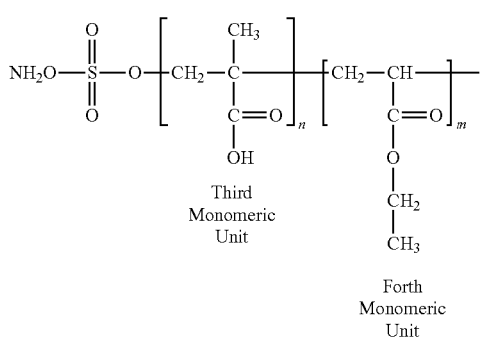
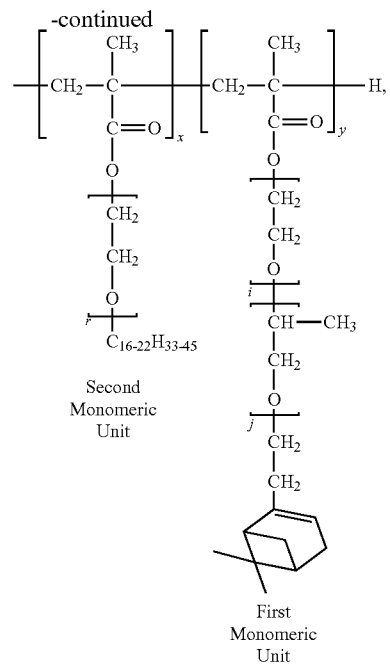

A.XXXII wherein n, m, x, and y are sufficient to obtain the molecular weight of greater than or equal to 30,000 grams per mole; r is an integer from 10 to 40; i is an integer of from 15 to 30, and j is an integer of from 2 to 10, wherein the $C_{16\text{-}22}$ group of formula A.XXXII is linear, wherein at least a portion of the composition is a structured surfactant phase having an ordered structure;

wherein based on 100 parts by weight of the composition:
(a) about 2 to 14.8 parts by weight of total composition is at least one anionic surfactant, and
(b) 0.2 to about 10 parts by weight of the composition is at least one surfactant selected from the group consisting of amphoteric surfactants, zwitterionic surfactants, nonionic surfactants, and cationic surfactants, (c) electrolyte in an amount effective to, in combination with components (a) and (b) to provide the structured surfactant phase having the ordered structure comprising the multi-lamellar vesicle surfactant phase having an opaque visual appearance and exhibiting a yield strength of greater than 0 Pascals, wherein the electrolyte comprises NaCl;

wherein the composition has
- 10-15 wt. % total amount of surfactants (a) and (b),
- 2-3 wt. % NaCl, and
- 0.5-1 wt. % said copolymer;

wherein the composition has less than a 40% loss in initial viscosity after 3 freeze thaw cycles, the initial viscosity being at least 100 cp; the freeze thaw cycle comprising the steps of maintaining the composition for 12 hours at 25° C. and then 12 hours at −10° C. to result in a composition having a stable freeze thaw viscosity; the initial viscosity and the freeze thaw viscosity measured at a same RPM in the range of 50-100 rpm by a Brookfield viscometer using a RV4 spindle;

wherein the weight ratio of the first monomeric unit to the second monomeric unit is 4:6, wherein the copolymer has
- 1-10 parts by weight said first monomeric unit,
- 1-10 parts by weight said second monomeric unit,
- 20-60 parts by weight said third monomeric unit,
- 25-70 parts by weight said fourth monomeric unit.

2. The composition of claim 1, comprising an additive suspendable at 25° C., which is insoluble in the aqueous phase of the composition at −10° C., and not suspendable after exposure to the temperature of −10° C. upon returning to 25° C. in a comparative composition the same as said freeze thaw stable composition but for an absence of the freeze thaw stability polymer, wherein the water insoluble additive is selected from the group consisting of:
- personal care benefit agents selected from the group consisting of oil, mica, exfoliation beads, emollients, moisturizers, pearlizing agent, a silicone hair conditioning agent, an antidandruff ingredient, a glycol emulsifier;
- hydraulic fracturing proppant; and
- home care additives selected from the group consisting of soil release agents, binders and fragrances.

3. The composition of claim 1, further comprising an additive selected from at least one member of the group consisting of:
1) a water insoluble component suspendable at 25° C., which is insoluble in the aqueous phase of the composition at −10° C., and not suspendable after exposure to the temperature of −10° C. upon returning to 25° C. in a comparative composition the same as said freeze thaw stable composition but for an absence of the freeze thaw stability polymer,
2) a water soluble component suspendable or soluble in the aqueous phase of the composition at 25° C., which is insoluble in the aqueous phase at −10° C., and not suspendable or soluble after exposure to the temperature of −10° C. upon returning to 25° C. in a comparative composition the same as said freeze thaw stable composition but for an absence of the freeze thaw stability polymer,
3) at least a portion of the surfactant suspendable or soluble in the aqueous phase at 25° C., which is not suspendable or soluble after exposure to the temperature of −10° C. upon returning to 25° C. in a comparative composition the same as said freeze thaw stable composition but for an absence of the freeze thaw stability polymer, and
4) a water insoluble component suspendable in the continuous phase of the composition which does not phase separate or settle after three freeze thaw cycles, whereas in the absence of the freeze thaw stability polymer the water insoluble component is not suspendable in the continuous phase after three freeze thaw cycles;

each freeze thaw cycle comprising exposing the composition to 12 hours at 25° C. and 12 hours at −10° C.

4. The composition of claim 1, wherein the composition is for cleaning hair or skin and comprises:
- the copolymer,
- at least one detersive surfactant, and
- at least one member of the group consisting of oil, mica, exfoliation beads, emollients, moisturizers, pearlizing agent, a silicone hair conditioning agent, an antidandruff ingredient, a glycol emulsifier provided that a 10% aqueous solution of said composition has a pH from about 4 to about 12.

5. The composition of claim 1, wherein the composition is a shampoo composition comprising at least one personal care benefit agent selected from the group consisting of one or more hair conditioning oils, one or more hair benefit agents other than a hair conditioning oil, or one or more hair conditioning oils, and one and more hair benefit agents other than a hair conditioning oil.

6. The composition of claim 1, comprising, based on 100 parts by weight of the composition, from about 0.1 parts by weight to about 20 parts by weight of a benefit agent selected from hair conditioning oils and mixtures thereof, and further comprising from about 0.01 parts by weight to about 5 parts by weight of a benefit agent selected from hair benefit agents other than hair conditioning oils and mixtures thereof.

7. The composition of claim 1, wherein the surfactant of the composition consists of at least 90 wt. % linear anionic surfactants and at most 10 wt. % branched surfactants.

8. The composition of claim 1, further comprising at least one polysaccharide selected from the group consisting of cationic polysaccharides, non-ionic polysaccharides, amphoteric polysaccharides, zwitterionic polysaccharides, C3-24 linear or branched alkyl chain substituted polysaccharides, and anionic polysaccharides.

9. The composition of claim 1, being a freeze thaw stable cosmetic composition for removing makeup from the skin and/or eyes, and/or for the cleansing thereof, comprising:
- a cosmetically acceptable vehicle or carrier comprising a continuous phase comprising a fatty phase and a water-containing aqueous phase.

10. The makeup remover/skin cleanser cosmetic composition of claim 9, wherein the cosmetically acceptable vehicle comprises the fatty phase and the aqueous phase, and
- comprises from 1% to 5% by weight of (a) the polyethylene glycol diester selected from the group consisting of polyethylene glycol distearate, polyethylene glycol dipalmitate, polyethylene glycol dioleate and polyethylene glycol dibehenate and from 0.5% to 5% by weight of the freeze thaw stability polymer.

11. The composition of claim 1, comprising:
- said additive, wherein said additive comprises at least one personal care benefit agent, wherein the personal care benefit is at least one water insoluble additive selected from the group consisting of oil, mica, and exfoliation beads.

12. A method for improving freeze thaw stability, comprising forming the composition of claim 1.

13. A method for improving freeze thaw stability, comprising forming the composition of claim 11.

14. A method for personal care comprising at least one of cleaning skin or hair, conditioning skin or hair, styling hair, protecting skin from aging, sun or acne, and coloring skin or hair, comprising applying the composition of claim 1 to skin or hair of a user.

15. A fluid for injecting into a subterranean formation comprising: the composition of claim 1 in an amount of from about 0.01 percent to about 1 percent by weight of the fluid, wherein water and dissolved salts are in an amount of greater than 50 parts per thousand by weight of the fluid.

16. The treatment fluid of claim 15, further comprising proppant.

17. A method for treating a subterranean formation to hydraulically fracture the subterranean formation or enhance oil recovery from the subterranean formation, comprising injecting the fluid of claim 15 into the subterranean formation.

18. A home care or industrial cleaning composition for cleaning fabrics or hard surfaces comprising, the composition of claim 1 and a surfactant and a home care or industrial cleaner benefit agent.

19. A method for cleaning a substrate selected from the group consisting of a hard surface and a fabric, comprising applying the composition of claim 18 to the substrate.

20. The composition of claim 1, wherein the copolymer has
4-10 parts by weight said first monomeric unit,
6-10 parts by weight said second monomeric unit,
20-60 parts by weight said third monomeric unit,
25-70 parts by weight said fourth monomeric unit.

\* \* \* \* \*